(12) United States Patent
Hinzen et al.

(10) Patent No.: US 7,405,201 B2
(45) Date of Patent: Jul. 29, 2008

(54) ANTIBACTERIAL MACROCYCLES

(75) Inventors: Berthold Hinzen, Velbert (DE); Heike Brötz-Oesterhelt, Wuppertal (DE); Rainer Endermann, Wuppertal (DE); Kerstin Henninger, Wuppertal (DE); Holger Paulsen, Wuppertal (DE); Siegfried Raddatz, Köln (DE); Thomas Lampe, Düsseldorf (DE); Veronika Hellwig, Wuppertal (DE); Andreas Schumacher, Efringen-Kirchen (DE)

(73) Assignee: Bayer Healthcare AG, Leverkusen (DE)

(*) Notice: Subject to any disclaimer, the term of this patent is extended or adjusted under 35 U.S.C. 154(b) by 0 days.

(21) Appl. No.: 10/490,192

(22) PCT Filed: Sep. 6, 2002

(86) PCT No.: PCT/EP02/09968

§ 371 (c)(1),
(2), (4) Date: Dec. 6, 2004

(87) PCT Pub. No.: WO03/024996

PCT Pub. Date: Mar. 27, 2003

(65) Prior Publication Data

US 2005/0107288 A1    May 19, 2005

(30) Foreign Application Priority Data

Sep. 19, 2001 (DE) .................. 101 46 104

(51) Int. Cl.
*A61K 38/12* (2006.01)
*C07K 5/12* (2006.01)
*C07K 1/00* (2006.01)

(52) U.S. Cl. .......................... 514/11; 530/317

(58) Field of Classification Search .............. 530/317, 530/333; 514/9
See application file for complete search history.

(56) References Cited

U.S. PATENT DOCUMENTS 4,492,650 A    1/1985  Michel et al. ............ 260/112.5

FOREIGN PATENT DOCUMENTS

| EP | 0792886 | 3/1997 |
|----|---------|--------|
| JP | 5065297 | 3/1993 |
| JP | 5117298 | 5/1993 |
| WO | 0107467 | 1/2001 |

OTHER PUBLICATIONS

MP Gamcsik and JT Gerig, FEBS (1986) 196(1) pp. 71-74.*
C Minks, et al. Anal. Biochem. (2000) 284, pp. 29-34.*
CL Gentry, et al. Peptides (1999) 20, pp. 1229-1238.*
PJ Cachia, et a. Biochemistry (1983) 22, pp. 4145-4152.*
S.R. Vippagunta, et al. Adv. Drug Delivery Rev. (2001) 48, pp. 3-26.*
Schmidt, U. et a l., "Synthesis of Enopeptin B from *Streptomyces* sp. RK-1051", Angew. Chem. Int. Ed. Engl., 36(10): 1110-1112 (1997).
Koshino, H. et al., "The Structure of Enopeptins A and B, Novel Depsipeptide Antibiotics", Tetrahedron Letters, 32(52): 7707-7710 (1991).
Osada, H. et al., "Enopeptin A, a Novel Depsipeptide Antibiotic with Anti-Bacteriophage Activity", Journal of Antibiotics, 44(12): 1463-1466 (1991).

* cited by examiner

*Primary Examiner*—Andrew D. Kosar
(74) *Attorney, Agent, or Firm*—Edwards Angell Palmer & Dodge LLP; Barry Kramer; Ralph A. Loren

(57) ABSTRACT

The present invention relates to compounds of the general formula (I), processes for their preparation, pharmaceutical compositions comprising them, and their use in the treatment of diseases in humans or animals.

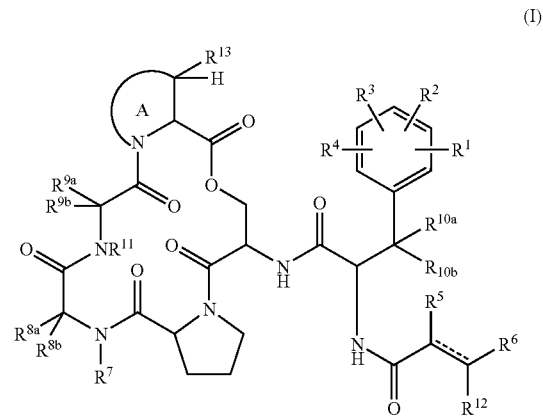

(I)

18 Claims, 3 Drawing Sheets

ANTIBACTERIAL MACROCYCLES

The present invention relates to compounds, processes for their preparation, pharmaceutical compositions comprising them, and their use in the treatment of diseases in humans or animals.

U.S. Pat. No. 4,492,650 describes the compounds

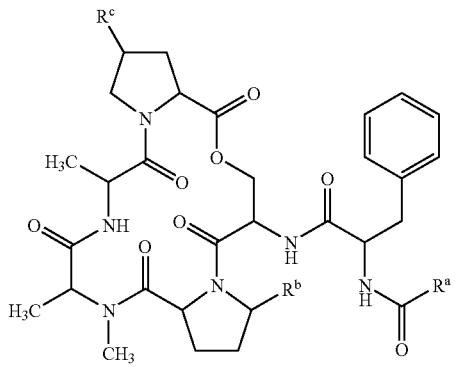

($R^c$ always hydrogen, $R^a$ is hepta-1,3,5-trienyl, $R^b$ is hydrogen or $R^a$ is hepta-1,3,5-trienyl, $R^b$ is methyl or $R^a$ is hepta-1,3-dienyl, $R^b$ is methyl or $R^a$ is penta-1,3-dienyl, $R^b$ is methyl or $R^a$ is penta-1,3-dienyl, $R^b$ is hydrogen or $R^a$ is penta-5-hydroxyl-1,3-dienyl, $R^b$ is methyl) as antibacterially active.

JP 05 065 297 describes enopeptin A ($R^a$ is octa-1,3,5,7-tetraenyl, $R^b$ is hydrogen, $R^c$ is methyl) as antibacterially active.

JP 05 177 298 describes depsipeptides A and B, in which $R^a$ is a radical

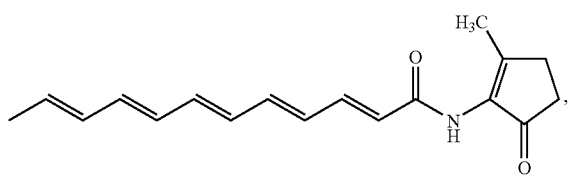

$R^b$ is hydrogen, $R^c$ is hydrogen or methyl as antibacterially active.

It is an object of the present invention to make available alternative compounds having comparable or improved antibacterial action for the treatment of bacterial diseases in humans and animals.

The present invention therefore relates to compounds of the general formula (I)

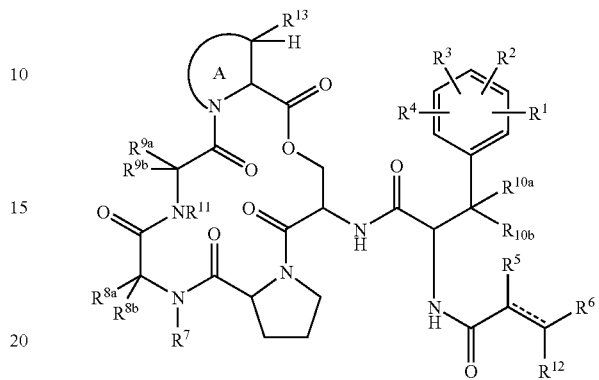

in which $R^1$ denotes halogen, alkyl, trifluoromethyl, trifluoromethoxy, nitro, amino, alkylamino, or dialkylamino, $R^2$ denotes hydrogen, halogen, alkyl, nitro, amino, alkylamino or dialkylamino, $R^3$ denotes hydrogen, halogen, alkyl, nitro, amino, alkylamino or dialkylamino, $R^4$ denotes hydrogen, halogen, alkyl, nitro, amino, alkylamino or dialkylamino, $R^5$ denotes hydrogen, $C_1$-C4-alkyl, fluorine or chlorine, $R^6$ denotes hydrogen, halogen or alkyl, $R^7$ denotes alkyl or (cycloalkyl)alkyl, $R^{8a}$ denotes alkyl, alkylene, cycloalkyl or (cycloalkyl)alkyl, where $R^{8a}$ optionally can be substituted by 1, 2 or 3 substituents, which independently of one another are selected from the group consisting of hydroxyl, alkoxy, a radical —$OR^{8a-1}$, carboxyl, alkoxycarbonyl, amino, alkylamino, dialkylamino, aminocarbonyl, alkylaminocarbonyl, dialkylaminocarbonyl, aminosulfonyl, alkylaminosulfonyl, dialkylaminosulfonyl, arylaminosulfonyl, heterocyclylaminosulfonyl, heteroarylaminosulfonyl, aminocarbonylamino, hydroxycarbonylamino, alkoxycarbonylamino, aminocarbonyloxy, in which $R^{8a-1}$ is a carbonyl-bonded amino acid radical, or $R^7$ and $R^{8a}$ together with the carbon atom to which $R^{8a}$ is bonded and the nitrogen atom to which $R^7$ is bonded, form a heterocyclyl ring, which optionally can be substituted by 1, 2 or 3 substituents, which independently of one another are selected from the group consisting of halogen, alkyl, trifluoromethyl, trifluoromethoxy, nitro, azido, amino, alkylamino, dialkylamino, hydroxyl, alkoxy, alkanoyloxy, $R^{8b}$ denotes hydrogen or alkyl, $R^{9a}$ denotes hydrogen, alkyl, hydroxyalkyl, carboxylalkyl or aminoalkyl, $R^{9b}$ denotes hydrogen or alkyl, $R^{10a}$ denotes hydrogen, alkyl or fluorine, $R^{10b}$ denotes hydrogen or fluorine, $R^{11}$ denotes hydrogen or alkyl, $R^{12}$ denotes alkyl, alkenyl, cycloalkyl, cycloalkenyl, (cycloalkyl)alkyl, (cycloalkenyl)alkyl, (cycloalkyl)alkenyl (cycloalkenyl)alkenyl, where $R^{12}$ optionally can be substituted by 1, 2 or 3 substituents, which independently of one another are selected from the group consisting of halogen, hydroxyl, alkoxy, fluoroalkoxy, aryloxy, alkanoyloxy, alkoxycarbonyl, aminocarbonyl, alkylaminocarbonyl, dialkylaminocarbonyl, aminosulfonyl, alkylaminosulfonyl, dialkylaminosulfonyl, arylaminosulfonyl, heteroarylaminosulfonyl, heterocyclylaminosulfonyl, aminocarbonylamino, alkoxycarbonylamino, or $R^6$ and $R^{12}$, together with the carbon atom to which they are bonded, form a cycloalkyl, which optionally can be substituted by 1 or 2 substituents, which independently of one another are selected from the group consisting of halogen, hydroxyl, alkoxy, $R^{13}$ denotes hydrogen or alkyl, A represents a heterocycle which optionally can be substituted by 1, 2 or 3 substituents, which independently of one another are selected from the group consisting of halogen, alkyl, trifluoromethyl, trifluoromethoxy, nitro, amino, alkylamino, dialkylamino, hydroxyl, alkoxy, alkanoyloxy, carboxyl, alkoxycarbonyl, azido, alkoxycarbonylamino,

----- represents a single or double bond, and their pharmaceutically tolerable salts, solvates and hydrates.

BRIEF DESCRIPTION OF THE DRAWINGS

The following detailed description, given by way of example, but not intended to limit the invention solely to the specific embodiments described, may best be understood in conjunction with the accompanying drawings, in which.

Figure 1:
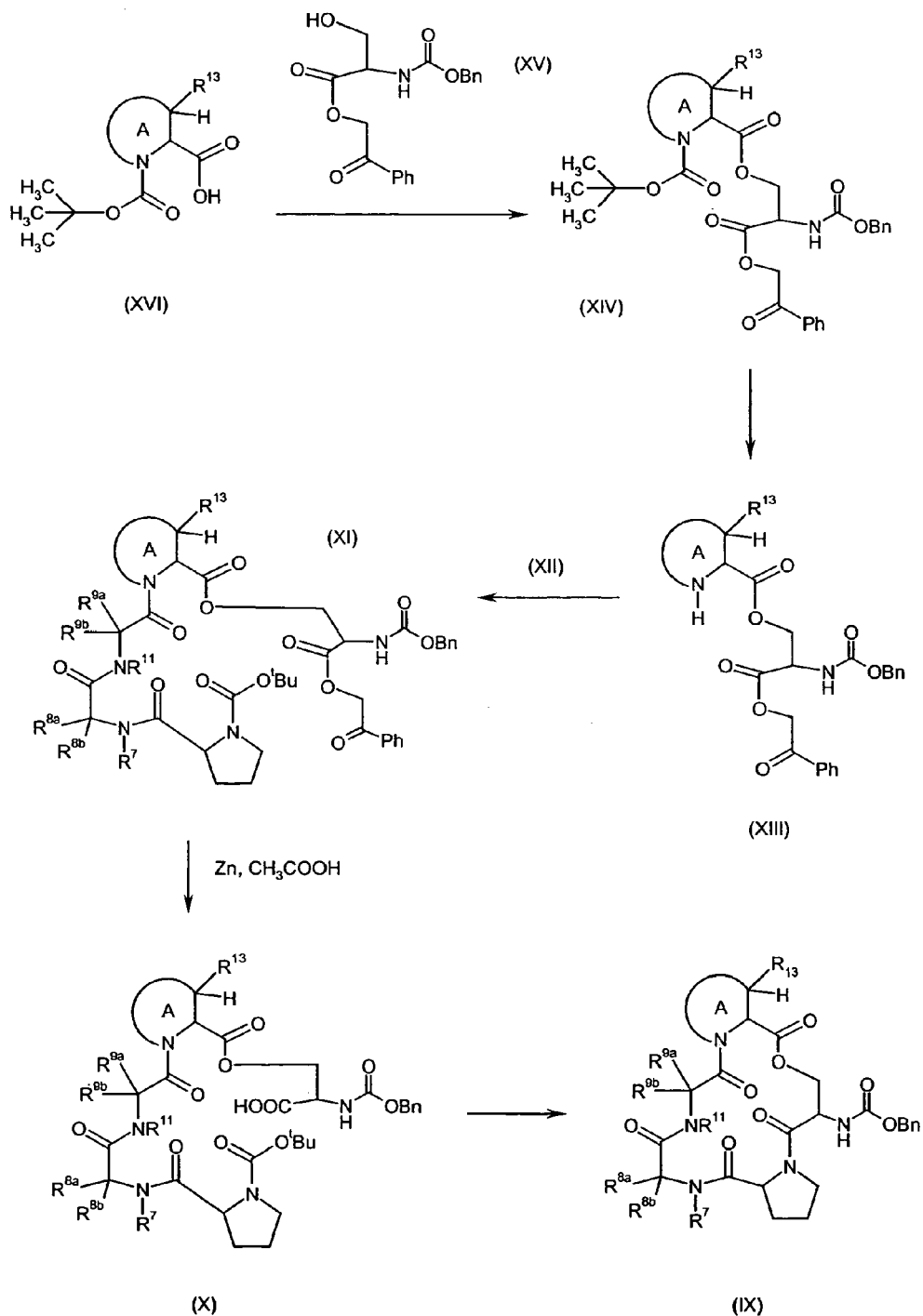
FIG. 1 depicts a reaction scheme in accordance with the invention which shows a synthetic scheme for Compound IX.
Figure 2:
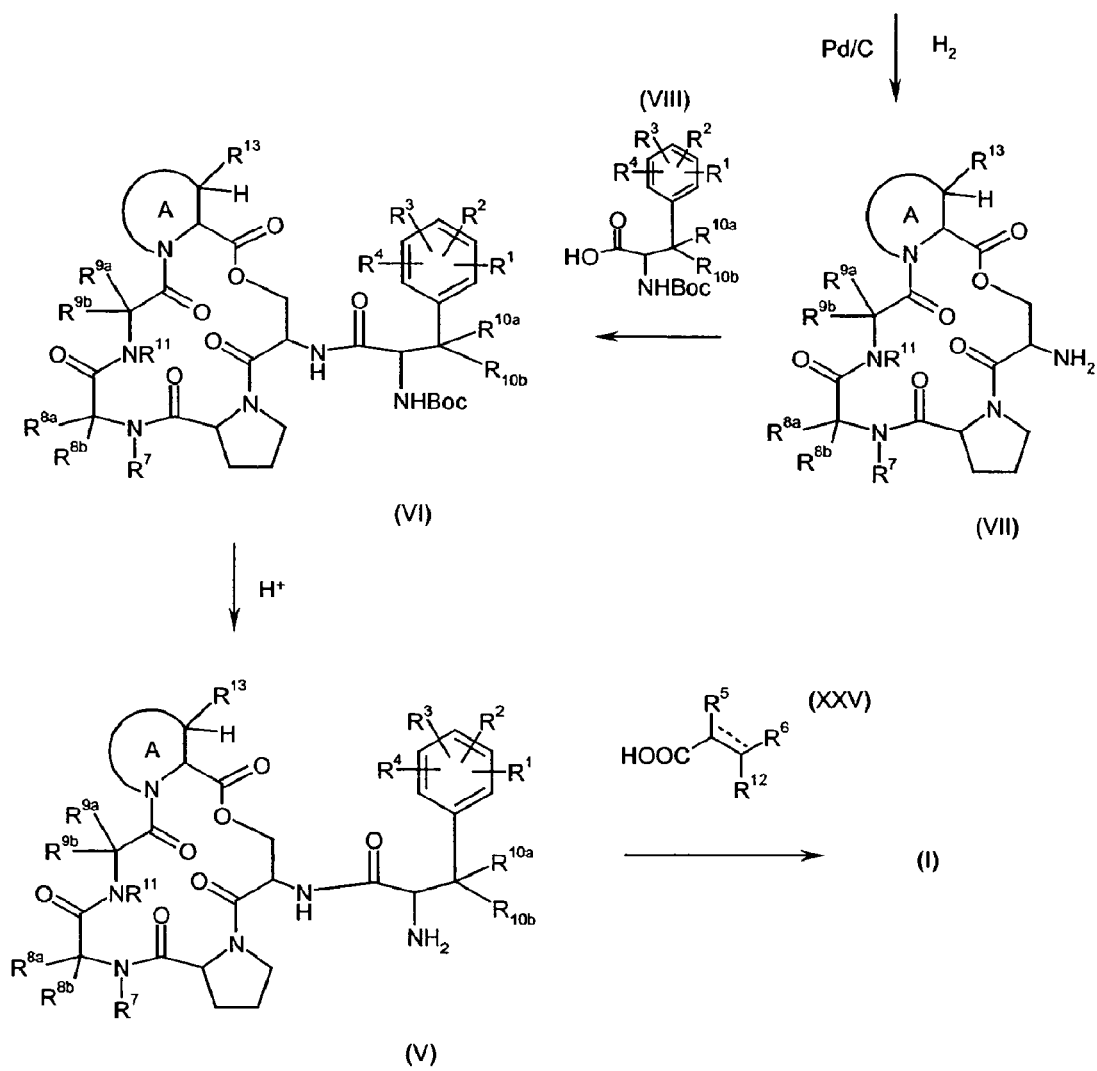
FIG. 2 depicts a reaction scheme in accordance with the invention which shows a synthetic scheme for Compound I.
Figure 3:
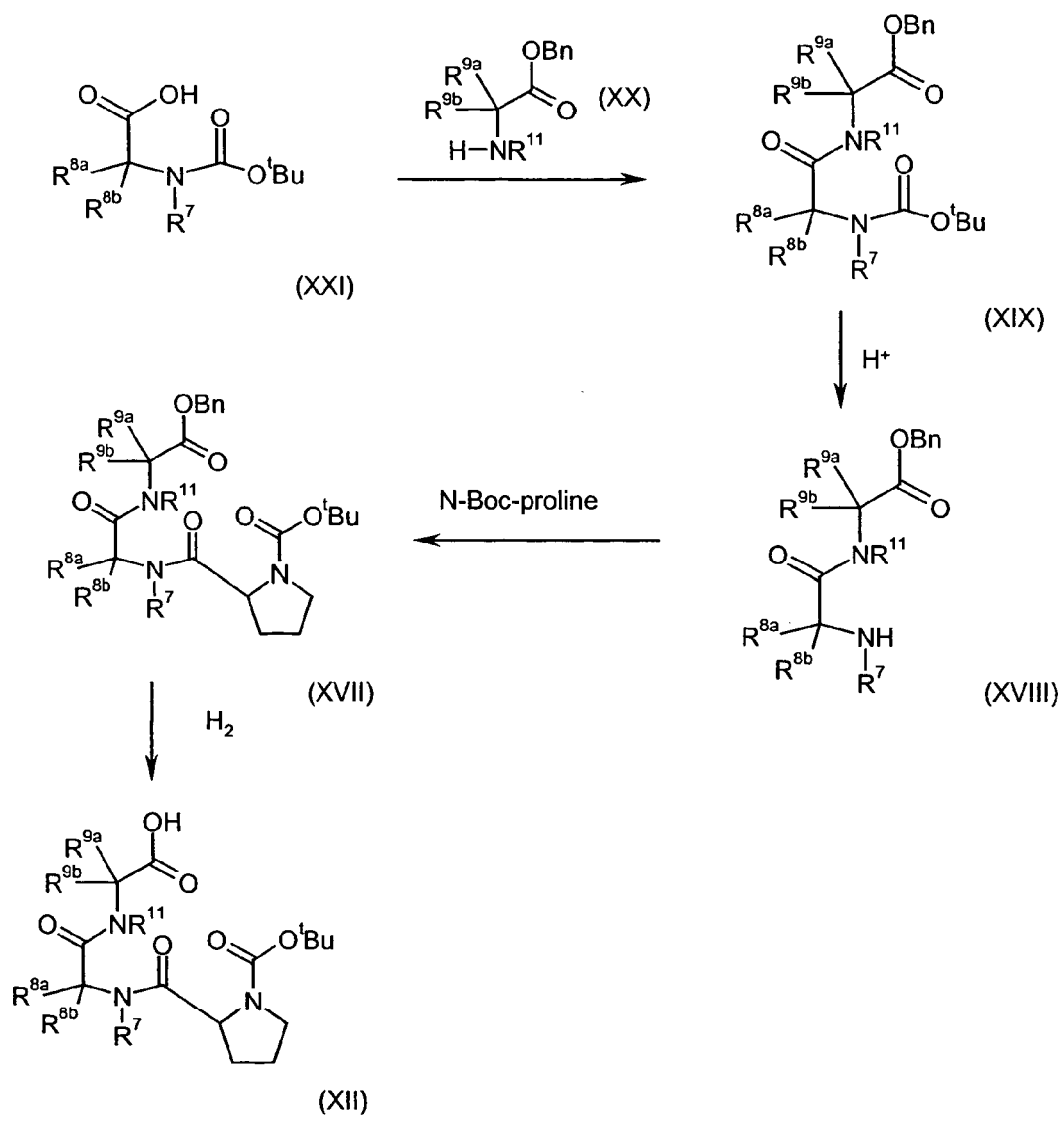
FIG. 3 depicts a reaction scheme in accordance with the invention which shows a synthetic scheme for Compound XII.

The compounds of the general formula (I) according to the invention can occur in various stereoisomeric forms, which either behave as image and mirror image (enantiomers), or which do not behave as image and mirror image (diastereomers). The invention relates both to the enantiomers and the diastereomers, and to their respective mixtures. Just like the diastereomers, the racemic forms can be separated into the stereoisomerically uniform constituents in a known manner.

The substances of the general formula (I) according to the invention can also be present as salts. In the context of the invention, pharmaceutically tolerable salts are preferred.

Pharmaceutically tolerable salts can be salts of the compounds according to the invention with inorganic or organic acids. Preferred salts are those with inorganic acids such as, for example, hydrochloric acid, hydrobromic acid, phosphoric acid or sulfuric acid, or salts with organic carboxylic or sulfonic acids such as, for example, acetic acid, propionic acid, maleic acid, fumaric acid, malic acid, citric acid, tartaric acid, lactic acid, benzoic acid, or methanesulfonic acid, benzene-sulfonic acid, toluenesulfonic acid or naphthalenedisulfonic acid.

Pharmaceutically tolerable salts can likewise be salts of the compounds according to the invention with bases, such as, for example, metal or ammonium salts. Preferred examples are alkali metal salts (e.g. sodium or potassium salts), alkaline earth metal salts (e.g. magnesium or calcium salts), and ammonium salts which are derived from ammonia or organic amines, such as, for example, ethylamine, di- or triethylamine, ethyldiisopropylamine, monoethanolamine, di- or triethanolamine, dicyclohexylamine, dimethylaminoethanol, dibenzylamine, N-methylmorpholine, dihydroabietylamine, methylpiperidine, arginine, lysine, ethylenediamine or 2-phenylethylamine.

The abovementioned general radical definitions or radical definitions stated in preferred ranges apply both to the final products of the formula (I) and correspondingly to the starting substances or intermediates in each case needed for the preparation.

The radical definitions specifically stated in the respective combinations or preferred combinations of radicals are arbitrarily also replaced by radical definitions of other combinations independently of the respectively stated combinations of the radicals.

Alkyl and the alkyl moieties in substituents such as alkoxy, mono- and dialkylamino, alkylsulfonyl comprise comprises linear and branched alkyl, e.g. $C_1$-$C_{24}$-, preferably $C_1$-$C_{12}$- and $C_7$-$C_{24}$-, in particular $C_1$-$C_6$- and $C_1$-$C_4$-alkyl.

$C_1$-$C_{24}$-Alkyl comprises methyl, ethyl, n- and i-propyl, n-, i-, sec- and tert-butyl, n-pentyl, isopentyl, neopentyl, hexyl, 2-ethylhexyl, n-octyl, decyl, dodecyl, palmityl, stearyl.

$C_1$-$C_{12}$-Alkyl comprises methyl, ethyl, n- and i-propyl, n-, i-, sec- and tert-butyl, n-pentyl, isopentyl, neopentyl, hexyl, 2-ethylhexyl, n-octyl decyl, dodecyl.

$C_1$-$C_6$-Alkyl comprises methyl, ethyl, n- and i-propyl, n-, i-, sec- and tert-butyl, n-pentyl, isopentyl, neopentyl, hexyl.

$C_1$-$C_4$-Alkyl comprises methyl, ethyl, n- and i-propyl, n-, i-, sec- and tert-butyl.

Cycloalkyl comprises polycyclic saturated hydrocarbon radicals having up to 14 C atoms, namely monocyclic $C_3$-$C_{12}$-, preferably $C_3$-$C_8$-alkyl, such as, for example, cyclopropyl, cyclobutyl, cyclopentyl, cyclohexyl, cycloheptyl, cyclooctyl, cyclononyl, and polycyclic alkyl, i.e. preferably bicyclic and tricyclic, optionally spirocyclic $C_7C_{14}$-alkyl, such as, for example, bicyclo[2.2.1]-hept-1-yl, bicyclo[2.2.1]-hept-2-yl, bicyclo[2.2.1]-hept-7-yl, bicyclo[2.2.2]-oct-2-yl, bicyclo[3.2.1]-oct-2-yl, bicyclo-[3.2.2]-non-2-yl and adamantyl.

Cycloalkenyl comprises polycyclic unsaturated, nonaromatic hydrocarbon radicals having up to 14 C atoms, namely monocyclic $C_3$-$C_{12}$-, preferably $C_3$-$C_8$-alkyl, such as, for example, cyclopentenyl, cyclohexenyl, cycloheptenyl, cyclooctenyl, cyclononenyl, and polycyclic alkyl, i.e. preferably bicyclic and tricyclic, optionally spirocyclic $C_7$-$C_{14}$-alkenyl.

(Cycloalkyl)alkyl represents an alkyl radical which is substituted by a cycloalkyl radical, cyclohexylmethyl may be mentioned by way of example. Correspondingly (Cycloalkenyl)alkyl denotes an alkyl radical which is substituted by a cycloalkenyl ring, e.g. 2-cyclohexenylmethyl.

Aryl in the context of the invention represents an aromatic radical having preferably 6 to 10 carbon atoms. Preferred aryl radicals are phenyl and naphthyl.

Alkoxy in the context of the invention preferably represents a straight-chain or branched alkoxy radical in particular having 1 to 6, 1 to 4 or 1 to 3 carbon atoms. A straight-chain or branched alkoxy radical having 1 to 3 carbon atoms is preferred.

The following may be mentioned by way of example and preferably: methoxy, ethoxy, n-propoxy, isopropoxy, t-butoxy, n-pentoxy and n-hexoxy.

Alkoxycarbonyl in the context of the invention preferably represents a straight-chain or branched alkoxy radical having 1 to 6 or 1 to 4 carbon atoms, which is linked via a carbonyl group. A straight-chain or branched alkoxycarbonyl radical having 1 to 4 carbon atoms is preferred. The following may be mentioned by way of example and preferably: methoxycarbonyl, ethoxycarbonyl, n-propoxycarbonyl, isopropoxycarbonyl and t-butoxycarbonyl.

Alkanoyloxy in the context of the invention preferably represents a straight-chain or branched alkyl radical having 1 to 6, 1 to 5 or 1 to 3 carbon atoms, which carries a doubly bonded oxygen atom in the 1-position and is linked in the 1-position by means of a further oxygen atom. A straight-chain or branched alkanoyloxy radical having 1 to 3 carbon atoms is preferred. The following may be mentioned by way of example and preferably: acetoxy, propionoxy, n-butyroxy, i-butyroxy, pivaloyloxy and n-hexanoyloxy.

Monoalkylamino in the context of the invention represents an amino group having a straight-chain or branched alkyl substituent, which preferably has 1 to 6, 1 to 4 or 1 to 2 carbon atoms. A straight-chain or branched monoalkylamino radical having 1 to 4 carbon atoms is preferred. The following may be mentioned by way of example and preferably: methylamino, ethylamino, n-propylamino, isopropylamino, t-butylamino, n-pentylamino and n-hexylamino.

Dialkylamino in the context of the invention represents an amino group having two identical or different straight-chain or branched alkyl substituents, which preferably in each case have 1 to 6, 1 to 4 or 1 to 2 carbon atoms. Straight-chain or branched dialkylamino radicals having in each case 1 to 4 carbon atoms are preferred. The following may be mentioned by way of example and preferably: N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Mono- or dialkylaminocarbonyl in the context of the invention represents an amino group, which is linked via a carbonyl group and which has a straight-chain or branched or two identical or different straight-chain or branched alkyl substituents having preferably in each case 1 to 4 or 1 to 2 carbon atoms. The following may be mentioned by way of example and preferably: methylaminocarbonyl, ethylaminocarbonyl, isopropylaminocarbonyl, t-butylaminocarbonyl, N,N-dimethylaminocarbonyl, N,N-diethylaminocarbonyl, N-ethyl-N-methylaminocarbonyl and N-t-butyl-N-methylaminocarbonyl.

Alkylcarbonylamino (acylamino) in the context of the invention represents an amino group having a straight-chain or branched alkanoyl substituent, which preferably has 1 to 6, 1 to 4 or 1 to 2 carbon atoms and is linked via the carbonyl group. A monoacylamino radical having 1 to 2 carbon atoms is preferred. The following may be mentioned by way of example and preferably: formamido, acetamido, propionamido, n-butyramido and pivaloylamino.

Heterocyclyl (heterocycle) represents a mono- or polycyclic, heterocyclic radical having 4 to 10 ring atoms and up to 3, preferably 1, heteroatom(s) or hetero group(s) from the series consisting of N, O, S, SO, $SO_2$. 4- to 8-membered heterocyclyl is preferred. Mono- or bicyclic heterocyclyl is preferred. Monocyclic heterocyclyl is particularly preferred. Preferred heteroatoms are N and O. The heterocyclyl radicals can be saturated or partially unsaturated. Saturated heterocyclyl radicals are preferred. The heterocyclyl radicals can be bonded via a carbon atom or a heteroatom. 5- to 7-membered, monocyclic saturated heterocyclyl radicals having up to two heteroatoms from the series consisting of O, N and S are particularly preferred. The following may be mentioned for example and preferably: oxetan-3-yl, pyrrolidin-2-yl, pyrrolidin-3-yl, pyrrolinyl, tetrahydrofuranyl, tetrahydrothienyl, pyranyl, piperidinyl, thiopyranyl, morpholinyl, perhydroazepinyl. A nitrogen heterocyclyl ring is in this case a heterocycle, which as heteroatoms only contains nitrogen atoms.

Heteroaryl represents an aromatic, mono- or bicyclic radical having 5 to 10 ring atoms and up to 5 heteroatoms from the series consisting of S, O and/or N. 5- to 6-membered heteroaryls having up to 4 heteroatoms are preferred. The heteroaryl radical can be bonded via a carbon atom or heteroatom. The following may be mentioned by way of example and preferably: thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Alkoxycarbonylamino in the context of the invention represents an amino group having a straight-chain or branched alkoxycarbonyl substituent, which preferably in the alkoxy radical has 1 to 6 or 1 to 4 carbon atoms and is linked via the carbonyl group. An alkoxycarbonylamino radical having 1 to 4 carbon atoms is preferred. The following may be mentioned by way of example and preferably: methoxycarbonylamino, ethoxycarbonylamino, n-propoxycarbonylamino and t-butoxycarbonylamino.

Aminosulfonyl represents an $—S(O)_2NH_2$ group. Accordingly, alkylaminosulfonyl, dialkylaminosulfonyl, arylaminosulfonyl, heterocyclylaminosulfonyl and heteroarylaminosulfonyl are substituted on the amino group by the corresponding radicals, i.e. alkyl, aryl etc.

Carbonyl-bonded amino acid radical represents an amino acid radical, which is bonded via the carbonyl group of the amino acid acid function. α-Amino acids in the L or in the D configuration are preferred here, in particular naturally occurring α-amino acids in the natural L configuration, e.g. glycine ($R^{8a-1}$ is aminomethylcarbonyl), L-alanine ($R^{8a-1}$ is (S)-(+)-2-aminopropylcarbonyl), L-proline ($R^{8a-1}$ is (S)-(−)-pyrrolidine-2-carbonyl), N,N-dimetylglycine ($R^{8a-1}$ is N,N-dimetylaminomethylcarbonyl).

Halogen in the context of the invention includes fluorine, chlorine, bromine and iodine. Fluorine or chlorine are preferred.

----- represents a single or double bond. This can be of cis- or trans-configuration, trans being preferred.

Preferred compounds in the context of the present invention are those of the general formula (I), in which $R^1$ denotes halogen, alkyl, or trifluoromethyl, $R^2$ denotes hydrogen, halogen or alkyl, $R^3$ denotes hydrogen, halogen or alkyl, $R^4$ denotes hydrogen, halogen or alkyl,
$R^5$ denotes hydrogen, methyl or fluorine,
$R^6$ denotes hydrogen or $C_1$-$C_4$-alkyl,
$R^7$ denotes alkyl,
$R^{8a}$ denotes alkyl, alkylene, cycloalkyl or (cycloalkyl)alkyl,
where $R^{8a}$ optionally can be substituted by 1 or 2 substituents, which independently of one another are selected from the group consisting of hydroxyl, alkoxy, a radical —$OR^{8a-1}$, alkoxycarbonyl, amino, alkylamino, dialkylamino, aminocarbonyl, alkylaminocarbonyl, dialkylaminocarbonyl, alkoxycarbonylamino,
in which $R^{8a-1}$ is a carbonyl-bonded amino acid radical,
or $R^7$ and $R^{8a}$, together with the carbon atom to which $R^{8a}$ is bonded and the nitrogen atom to which $R^7$ is bonded, form a heterocyclyl ring, which optionally can be substituted by 1 or 2 substituents, which independently of one another are selected from the group consisting of halogen, alkyl, amino, alkylamino, dialkylamino, hydroxyl, alkoxy, alkanoyloxy,
$R^{8b}$ denotes hydrogen,
$R^{9a}$ denotes hydrogen, methyl or hydroxymethyl,
$R^{9b}$ denotes hydrogen,
$R^{10a}$ denotes hydrogen,
$R^{10a}$ denotes hydrogen,
$R^{11}$ denotes hydrogen,
$R^{12}$ denotes alkyl, alkenyl, (cycloalkyl)alkyl, (cycloalkenyl)alkyl, (cycloalkyl)alkenyl, (cycloalkenyl)alkenyl,
where $R^{12}$ optionally can be substituted by 1 or 2 substituents, which independently of one another are selected from the group consisting of halogen, hydroxyl, alkoxy, or $R^6$ and $R^{12}$, together with the carbon atom to which they are bonded, form a cycloalkyl, which optionally can be substituted by 1 or 2 substituents, which independently of one another are selected from the group consisting of halogen, hydroxyl, alkoxy,
$R^{13}$ denotes hydrogen,
A represents a heterocycle which optionally can be substituted by 1 or 2 substituents, which independently of one another are selected from the group consisting of fluorine, alkyl, trifluoromethyl, alkoxycarbonylamino,

----- represents a single or double bond.

Preferred compounds in the context of the present invention are also those of the general formula (I), in which
$R^1$ denotes fluorine,
$R^2$ denotes hydrogen or fluorine,
$R^3$ denotes hydrogen,
$R^4$ denotes hydrogen,
$R^5$ denotes hydrogen or fluorine,
$R^6$ denotes hydrogen,
$R^7$ denotes methyl,
$R^{8a}$ denotes $C_1$-$C_4$-alkyl,
where $R^{8a}$ optionally can be substituted by 1 substituent selected from the group consisting of hydroxyl and a radical —$OR^{8a-1}$,
in which $R^{8a-1}$ is an aminomethylcarbonyl radical,
or $R^7$ and $R^{8a}$, together with the carbon atom to which $R^{8a}$ is bonded and the nitrogen atom to which $R^7$ is bonded, form a 5- to 6-membered nitrogen heterocyclyl ring, which can contain up to 2 nitrogen atoms and which optionally can be substituted by 1 substituent selected from the group consisting of alkyl, amino, alkylamino, dialkylamino, hydroxyl,
$R^{8b}$ denotes hydrogen,
$R^{9a}$ denotes hydrogen, alkyl or hydroxymethyl,
$R^{9b}$ denotes hydrogen,
$R^{10a}$ denotes hydrogen,
$R^{10b}$ denotes hydrogen,
$R^{11}$ denotes hydrogen,
$R^{12}$ denotes alkyl, alkenyl, cycloalkyl, cycloalkenyl, (cycloalkyl)alkyl, (cycloalkenyl)alkyl, (cycloalkyl)alkenyl (cycloalkenyl)alkenyl,
where $R^{12}$ optionally can be monosubstituted by hydroxyl, or $R^6$ and $R^{12}$, together with the carbon atom to which they are bonded, form a 5- to 6-membered cycloalkyl, which optionally can be monosubstituted by hydroxyl,
$R^{13}$ denotes hydrogen,
A represents a 5-membered heterocycle which contains 1 nitrogen atom and which optionally can be monosubstituted by a substituent selected from the group consisting of fluorine, alkyl,

----- represents a single or double bond.

Preferred compounds in the context of the present invention are those of the general formula (I), which have the general formula (II):

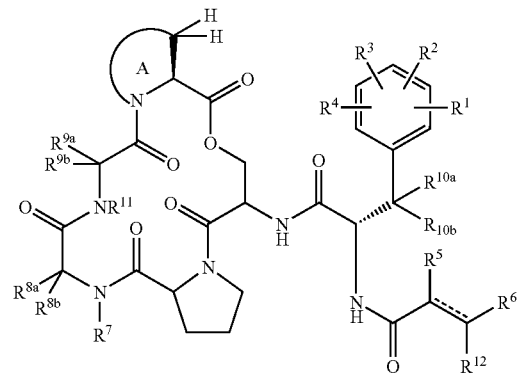

(II)

in which A,

----- and $R^1$ to $R^{12}$ are as defined above.

Furthermore, preferred compounds in the context of the present invention are those of the general formula (I), which have the general formula (III):

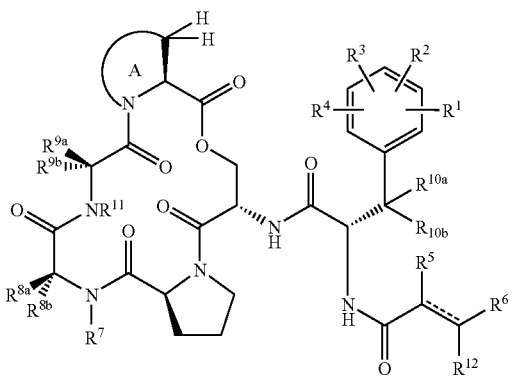

(III)

in which A,

----- and $R^1$ to $R^{12}$ are as defined above.

Furthermore, preferred compounds in the context of the present invention are those of the general formula (I), which have the general formula (IV):

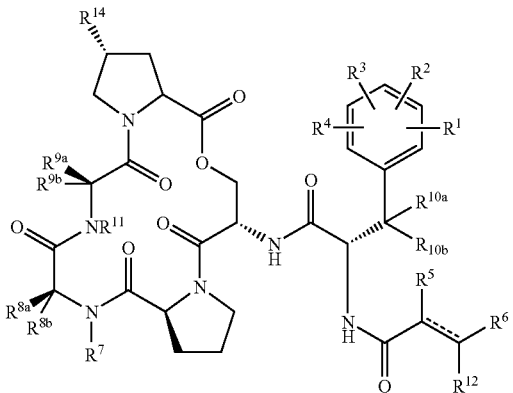

(IV)

in which A,

----- and $R^1$ to $R^{12}$ are as defined above, and $R^{14}$ is alkyl.

Furthermore, preferred compounds in the context of the present invention are those of the general formula (I),
in which $R^1$ denotes halogen and $R^2$, $R^3$ and $R^4$ are equal or identical and independently of one another are selected from the group consisting of hydrogen and halogen, particularly in which $R^1$ denotes fluorine and $R^2$, $R^3$ and $R^4$ are identical or different and independently of one another are selected from the group consisting of hydrogen and fluorine, in particular in which $R^1$ and $R^2$ are fluorine and in each case are meta to the benzylic methylene group, and $R^3$ and $R^4$ are hydrogen.

Furthermore, preferred compounds in the context of the present invention are those of the general formula (I), in which $R^5$ denotes hydrogen.

Furthermore, preferred compounds in the context of the present invention are those of the general formula (I), in which $R^6$ denotes hydrogen.

Furthermore, preferred compounds in the context of the present invention are those of the general formula (I), in which $R^7$ denotes methyl.

Furthermore, preferred compounds in the context of the present invention are those of the general formula (I), in which $R^{8a}$ denotes methyl, hydroxymethyl or $-OR^{8a-1}$, in which $R^{8a-1}$ denotes a carbonyl-bonded amino acid radical, in particular aminomethylcarbonyl or N-alkyl- or N,N-dialkylaminomethylcarbonyl and $R^{8b}$ denotes hydrogen.

Furthermore, preferred compounds in the context of the present invention are those of the general formula (I), in which $R^7$ and $R^{8a}$, together with the carbon atom to which $R^{8a}$ is bonded and the nitrogen atom to which $R^7$ is bonded, form a heterocyclyl ring, which optionally can be substituted by 1 or 2 substituents, which independently of one another are selected from the group consisting of halogen, alkyl and amino, in particular, in which $R^7$ and $R^{8a}$, together with the carbon atom to which $R^{8a}$ is bonded and the nitrogen atom to which $R^7$ is bonded, form a 5- to 6-membered heterocyclyl ring. Particularly preferred compounds are those in which $R^7$ and $R^{8a}$, together with the carbon atom to which $R^{8a}$ is bonded and the nitrogen atom to which $R^7$ is bonded, form a pyrrolidine ring, a morpholine ring or a piperidine ring.

Furthermore, preferred compounds in the context of the present invention are those of the general formula (I), in which $R^{9a}$ denotes alkyl, in particular methyl, and $R^{9b}$ denotes hydrogen.

Furthermore, preferred compounds in the context of the present invention are those of the general formula (I), in which $R^{10a}$ and $R^{10b}$ denote hydrogen.

Furthermore, preferred compounds in the context of the present invention are those of the general formula (I), in which $R^{11}$ denotes hydrogen.

Furthermore, preferred compounds in the context of the present invention are those of the general formula (I),
in which $R^{12}$ denotes $C_3$-$C_8$-alkyl, particularly in which $R^{12}$ denotes $C_3$-$C_5$-alkyl in the form of a chain, in particular $C_4$-alkyl in the form of a chain.

The following radicals $R^{12}$ are also preferred:

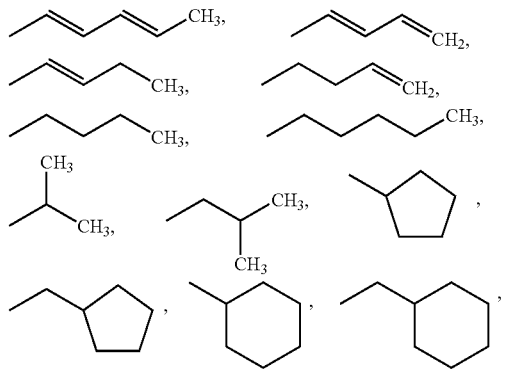

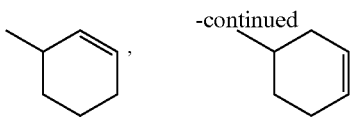

Furthermore, preferred compounds in the context of the present invention are those of the general formula (I), in which $R^{13}$ denotes hydrogen.

Furthermore, preferred compounds in the context of the present invention are those of the general formula (I), in which A represents a 5-membered heterocycle which contains 1 nitrogen atom and which optionally can be monosubstituted by a substituent selected from the group consisting of fluorine and alkyl.

Furthermore, preferred compounds in the context of the present invention are those of the general formula (I), in which $R^5$ and $R^6$ are hydrogen and

----- represents a trans double bond.

Furthermore, the following compounds are preferred in the context of the present invention:

(E)-hept-2-enoic acid [(S)-2-(3,5-difluorophenyl)-1-((3S,7S,13S,16S,19S)-13,16,17-trimethyl-2,6,12,15,18-pentaoxo-5-oxa-1,11,14,17-tetraaza-tricyclo[17.3.0.0$^{7,11}$]docos-3-ylcarbamoyl)-ethyl]-amide (E)-hept-2-enoic acid [(S)-2-(3,5-difluorophenyl)-1-((3S,9S,13S,15R,19S,22S)-15,19-dimethyl-2,8,12,18,21-pentaoxo-11-oxa-1,7,17,20-tetraaza-tetracyclo-[20.4.0.0$^{3,7}$.0$^{13,17}$]hexacos-9-ylcarbamoyl)-ethyl]-amide 3-cylcohexylpropanoic acid [(S)-2-(3,5-difluorophenyl)-1-((3S,9S,13S,15R,19S,22S)-15,19-dimethyl-2,8,12,18,21-pentaoxo-11-oxa-1,7,17,20-tetraaza-tetracyclo [20.4.0.0$^{3,7}$.0$^{13,17}$] hexacos-9-ylcarbamoyl)-ethyl]-amide 3-cyclohexyl-2-propenoic acid [(S)-2-(3,5-difluorophenyl)-1-((3S,9S,13S,15R,19S,22S)-15,19-dimethyl-2,8,12,18,21-pentaoxo-11-oxa-1,7,17,20-tetraaza-tetracyclo [20.4.0.0$^{3,7}$.0$^{13,17}$] hexacos-9-ylcarbamoyl)-ethyl]-amide The compounds of the present invention are distinguished by a broad spectrum of action against Gram-positive bacteria, where also multiresistant microorganisms can be covered, in particular staphylococci, pneumococci and enterococci including vancomycin- or methicillin-resistant strains.

The present invention furthermore relates to a process for the preparation of the compounds of the general formula (I), in which compounds of the general formula (V)

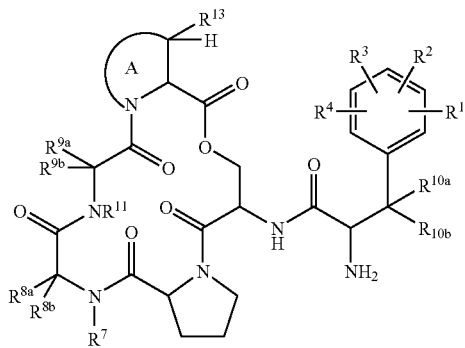

in which
$R^1$ to $R^4$, $R^7$ to $R^{11}$, $R^{13}$ and A have the meaning indicated above,
are reacted with compounds of the general formula (XXV)

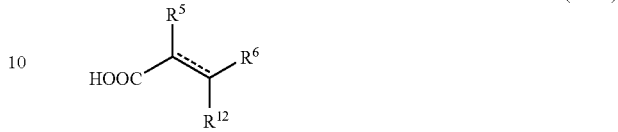

in which
$R^5$, $R^6$, $R^{12}$ and

----- have the meaning indicated above,
where these optionally can be present in activated form.

For the conversion of the compounds to activated form, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)-phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyl-uronium hexafluorophosphate (HATU), or 1-hydroxy-benztriazole (HOBt), or benzotriazol-1-yloxytris(dimethylamino)-phosphonium hexafluorophosphate (BOP), or mixtures of these with bases are suitable.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Suitable solvents in this context are inert organic solvents which do not change under the reaction conditions. These include halogenohydrocarbons such as dichlormethane or trichlormethane, hydrocarbon such as benzene, nitromethane, dioxane, dimethylformamide or acetonitrile. Likewise, it is possible to employ mixtures of the solvents. Dimethylformamide is particularly preferred.

The compounds of the general formula (XXV) are known or can be prepared from known carboxylic acids according to processes known from the literature.

The compounds of the general formula (V) are new and can be prepared by treating compounds of the general formula (VI)

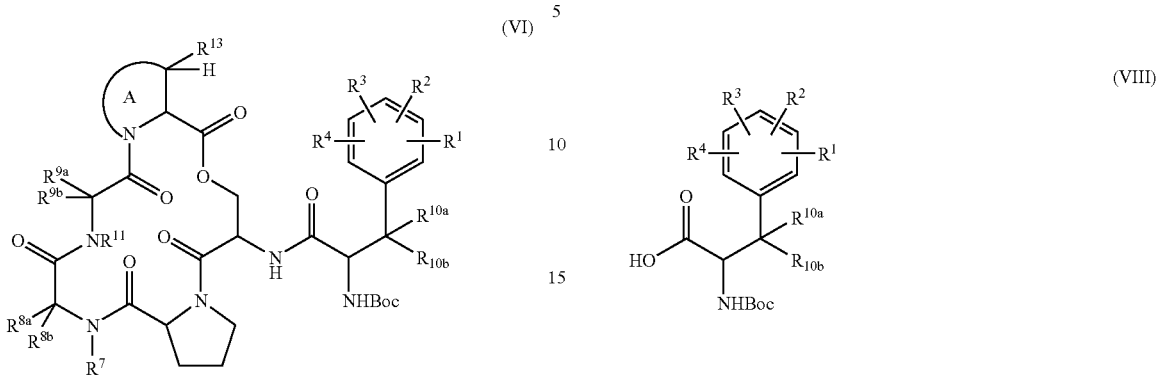

(VI)

in which
R$^1$ to R$^4$, R$^7$ to R$^{11}$, R$^{13}$ and A have the meaning indicated above,
with acid.

Suitable solvents in this context are inert organic solvents which do not change under the reaction conditions. These include halogenohydrocarbons such as dichlormethane or trichlormethane, hydrocarbon such as benzene, dioxane, nitromethane, dimethylformamide or acetonitrile. Likewise, it is possible to employ mixtures of the solvents. Dichloromethane is particularly preferred.

A suitable acid is in particular trifluoroacetic acid, particularly in aqueous solution, or hydrogen chloride in dioxane.

The compounds of the general formula (VI) are new and can be prepared by reacting compounds of the general formula (VII)

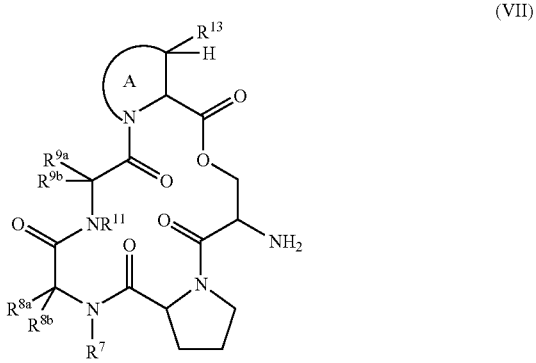

(VII)

in which
R$^7$ to R$^9$, R$^{11}$, R$^{13}$ and A have the meaning indicated above,
with compounds of the general formula (VIII)

(VIII)

in which
R$^1$ to R$^4$ and R$^{10}$ have the meaning indicated above in the presence of dehydrating reagents.

Suitable dehydrating reagents in this context are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyluronium hexafluorophosphate (HATU), or 1-hydroxybenztriazole (HOBt), or benzotriazol-1-yloxytris(dimethylamino)-phosphonium hexafluorophosphate (BOP), or mixtures of these, with bases. Preferably, the condensation is carried out using HATU.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine. Preferably, the condensation is carried out using diisopropylethylamine.

Suitable solvents in this context are inert organic solvents which do not change under the reaction conditions. These include halogenohydrocarbons such as dichlormethane or trichlormethane, hydrocarbon such as benzene, nitromethane, dioxane, dimethylformamide, acetonitrile or hexamethylphosphoramide. Likewise, it is possible to employ mixtures of the solvents. Dimethylformamide is particularly preferred.

The compounds of the general formula (VII) can also be present in the form of their salts, in particular of their hydrochlorides.

The compounds of the general formula (VIII) are known or can be prepared from known amino acids according to processes known from the literature.

The compounds of the general formula (XXV) are known or can be prepared from known carboxylic acids according to processes known from the literature.

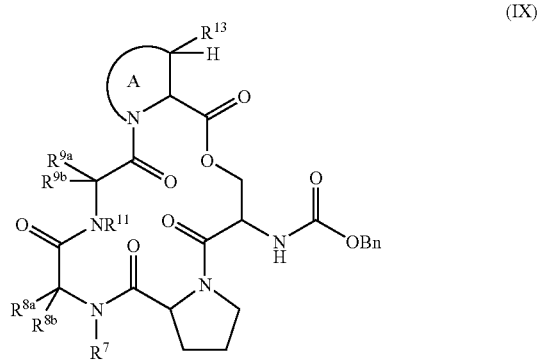

(IX)

in which
R$^7$ to R$^9$, R$^{11}$, R$^{13}$ and A have the meaning indicated above, optionally with addition of acid, e.g. using hydrogen chloride in methanol, are hydrogenated.

Suitable catalysts in this context are transition metals such as, for example, palladium, platinum or rhodium, preferably palladium, in an amount of from 0.01 to 1 equivalent based on the amount of the compound of the general formula (IX) employed, preferably 0.05 to 0.2 equivalents. Palladium, adsorbed on activated carbon, is very particularly preferred.

The compounds of the general formula (IX) are new and can be prepared by cyclizing compounds of the general formula (X)

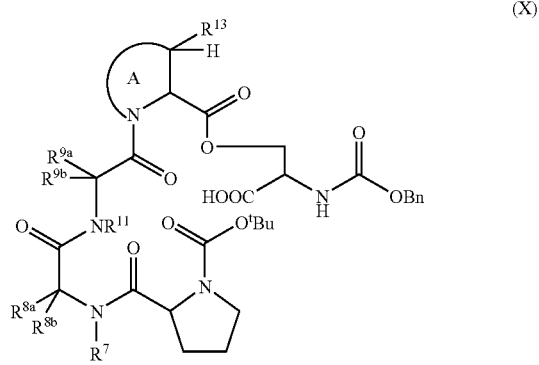

(X)

in which
R$^7$ to R$^{11}$, R$^{13}$ and A have the meaning indicated above.

For this purpose, the compounds of the general formula (X) are reacted successively with one another in a one-pot multi-stage reaction:
1. Formation of an active ester (e.g. using EDC and pentafluorophenol) and subsequent removal of the solvent.
2. Elimination of the Boc protective group by treatment with acid, e.g. with hydrogen chloride in dioxane, and subsequent removal of the solvent.
3. Cyclization in a two-phase mixture (water/organic solvent, e.g. dichlormethane/water or chloroform/water) by neutralization with aqueous sodium hydrogencarbonate solution (or other buffer systems) under dilution conditions.

Suitable dehydrating reagents in this context are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyluronium hexafluorophosphate (HATU), or 1-hydroxybenztriazole (HOBt), or benzotriazol-1-yloxytris(dimethylamino)-phosphonium hexafluoro-phosphate (BOP), or mixtures of these, with bases. Preferably, the condensation is carried out with EDC in the presence of pentafluorophenol.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Without being tied to this theory, the cyclization probably takes place by formation of the activated ester with the aid of the dehydrating reagent (1.), the formation of the ester hydrochloride with the aid of the acid (2.) and cyclization by slow release of the amine (3.).

The compounds of the general formula (X) are new and can be prepared by subjecting compounds of the general formula (XI)

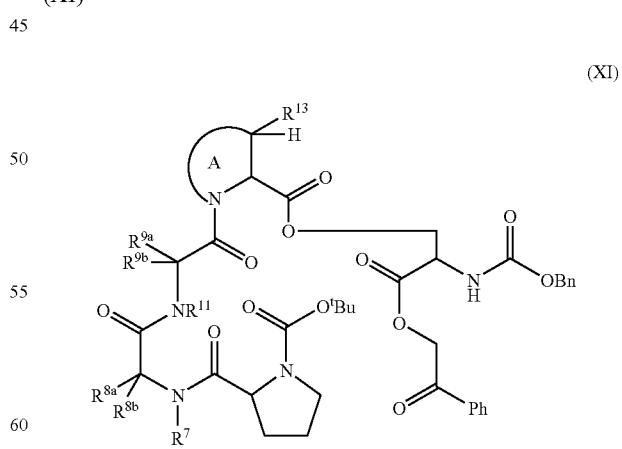

(XI)

in which
R$^7$ to R$^{11}$, R$^{13}$ and A have the meaning indicated above,
to a reductive ester hydrolysis, e.g. using zinc in 90% strength acetic acid.

The compounds of the general formula (XI) are new and can be prepared by reacting compounds of the general formula (XII)

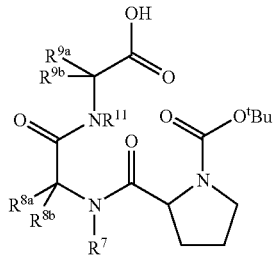
(XII)

in which
R⁷ to R⁹ and R¹¹ have the meaning indicated above,
with compounds of the general formula (XIII)

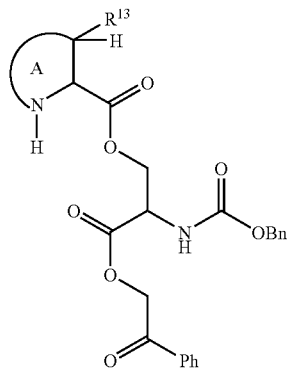
(XIII)

in which
R¹³ and A have the meaning indicated above, using dehydrating reagents.

Suitable dehydrating reagents in this context are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyl-uronium hexafluorophosphate (HATU), or 1-hydroxybenztriazole (HOBt), or benzotriazol-1-yloxytris(dimethylamino)-phosphonium hexafluoro-phosphate (BOP), or mixtures of these, with bases.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Preferably, the condensation is carried out using TPTU (2-(2-oxo-1(2H)-pyridyl)-1,1,3,3-tetramethyluronium tetrafluoroborate) in the presence of HOBT and base, in particular Hünig's base.

Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide or acetonitrile. Likewise, it is possible to employ mixtures of the solvents. Dichloromethane is particularly preferred.

The compounds of the general formula (XIII) can also be present in the form of their salts, in particular of their hydrochlorides.

The compounds of the general formula (XIII) are new and can be prepared by treating compounds of the general formula (XIV)

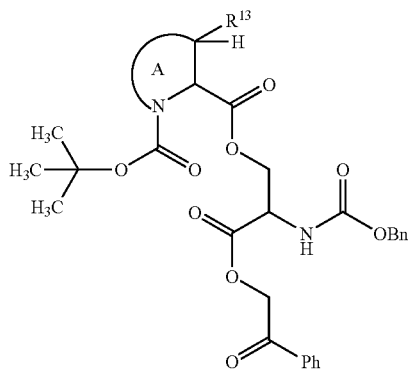
(XIV)

in which
R¹³ and A have the meaning indicated above,
with acid, in particular with hydrogen chloride in anhydrous organic solvents, in particular dioxane or tetrahydrofuran.

The compounds of the general formula (XIV) are new and can be prepared by reacting compounds of the general formula (XV)

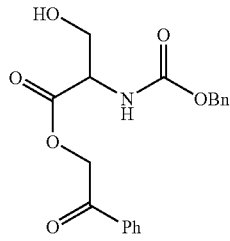
(XV)

with compounds of the general formula (XVI)

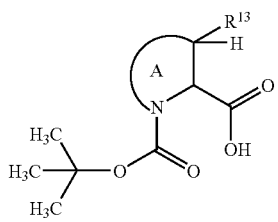
(XVI)

in which
R¹³ and A have the meaning indicated above,
optionally in the presence of dehydrating reagents.

Suitable dehydrating reagents in this context are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyl-uronium hexafluorophosphate (HATU), or 1-hydroxybenztriazole (HOBt), or benzotriazol-1-yloxytris(dimethylamino)-phosphonium hexafluoro-phosphate (BOP), or mixtures of these, with bases.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Preferably, the condensation is carried out using EDC in the presence of DMAP.

Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide or acetonitrile. Likewise, it is possible to employ mixtures of the solvents. Dichloromethane is particularly preferred.

The compounds of the general formula (XV) and (XVI) are known or can be prepared from amino acids according to methods known from the literature.

The compounds of the general formula (XII) are new and can be prepared by hydrogenating compounds of the general formula (XVII)

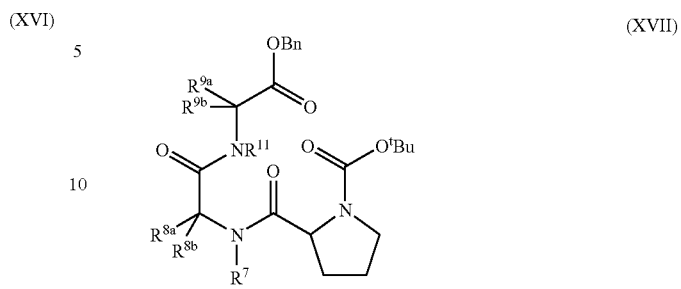
(XVII)

in which
R⁷ to R⁹ and R¹¹ have the meaning indicated above.

Suitable catalysts in this context are transition metals such as, for example, palladium, platinum or rhodium, preferably palladium, in an amount of from 0.01 to 1 equivalent, based on the mass of the compound of the general formula (XVII) employed, preferably 0.05 to 0.2 equivalents. Palladium, adsorbed on activated carbon, is very particularly preferred.

The compounds of the general formula (XVII) are new and can be prepared by reacting compounds of the general formula (XVIII)

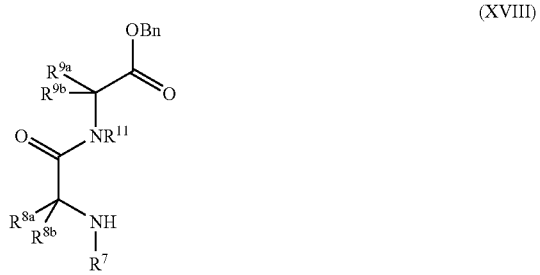
(XVIII)

in which
R⁷ to R⁹ and R¹¹ have the meaning indicated above,
with N-Boc-proline, optionally in the presence of dehydrating reagents.

Suitable dehydrating reagents in this context are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2l1)-pyridyl)-1,1,3,3-tetramethyluronium tetrafluoro-borate (TPTU) or O-(7-azabenzotriazol-1-yl)-N,N,N',N'-tetramethyl-uronium hexafluorophosphate (HATU), or 1-hydroxy-benztriazole (HOBt), or benzotriazol-1-yloxytris(dimethylamino)-phosphonium hexafluoro-phosphate (BOP), or mixtures of these, with bases.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Preferably, the condensation is carried out using HATU or using EDC in the presence of HOBt.

Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide or acetonitrile. Likewise, it is possible to employ mixtures of the solvents. Dichloromethane or dimethylformamide is particularly preferred.

The compounds of the general formula (XVIII) are new and can be prepared by treating compounds of the general formula (XIX)

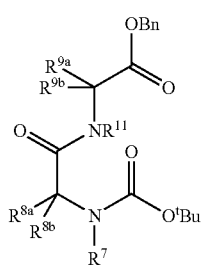

(XIX)

in which
$R^7$ to $R^9$ and $R^{11}$ have the meaning indicated above,
with acid, in particular with hydrogen chloride in anhydrous organic solvents, in particular dioxane or tetrahydrofuran, or with trifluoroacetic acid in dichloromethane.

The compounds of the general formula (XIX) are new and can be prepared by reacting compounds of the general formula (XX)

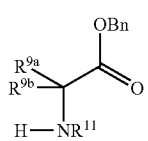

(XX)

in which
$R^9$ and $R^{11}$ have the meaning indicated above, with compounds of the general formula (XXI)

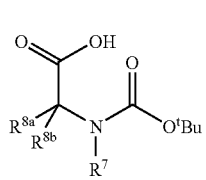

(XXI)

in which
$R^7$ and $R^8$ have the meaning indicated above,
optionally in the presence of dehydrating reagents.

Suitable dehydrating reagents in this context are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyl-uronium hexafluorophosphate (HATU), or 1-hydroxy-benztriazole (HOBt), or benzotriazol-1-yloxytris(dimethylamino)-phosphonium hexafluorophosphate (BOP), or mixtures of these, with bases.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Preferably, the condensation is carried out using HATU or using EDC in the presence of HOBt.

Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide or acetonitrile. Likewise, it is possible to employ mixtures of the solvents. Dimethylformamide or dichloromethane is particularly preferred.

The compounds of the general formulae (XX) and (XXI) are known or can be prepared from amino acids according to methods known from the literature.

Alternatively, for the preparation of the compounds of the general formula (I), compounds of the general formula (VII) can also be reacted with compounds of the general formula (XXII)

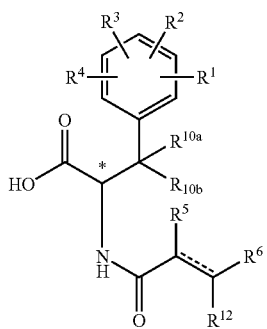

(XXII)

in which
$R^1$ to $R^6$, $R^{10}$, $R^{12}$ and

----- have the meaning indicated above,
optionally in the presence of dehydrating reagents.

Suitable dehydrating reagents in this context are, for example, carbodiimides such as, for example, N,N'-diethyl-, N,N,'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoro-borate (TPTU) or O-(7-azabenzotriazol-1-yl)-N,N,N',N'-tetramethyl-uronium hexafluorophosphate (HATU), or 1-hydroxybenztriazole (HOBt), or benzotriazol-1-yloxytris(dimethylamino)-phosphonium hexafluoro-phosphate (BOP), or mixtures of these, with bases.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Preferably, the condensation is carried out using HATU.

Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide or acetonitrile. Likewise, it is possible to employ mixtures of the solvents. Dimethylformamide is particularly preferred.

The compounds of the general formula (I) can epimerize in this reaction pathway on the carbon atom marked by an asterisk (*) in formula ((XXII) and can occur in the form of various diastereomers. In this case, undesired diastereomers are separated off according to standard methods, e.g. by chromatography.

The compounds of the general formula (XXII) are new and can be prepared by reacting compounds of the general formula (XXIII)

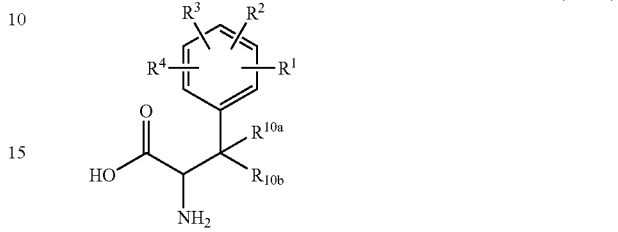

(XXIII)

in which
$R^1$ to $R^4$ and $R^{10}$ have the meaning indicated above,
with compounds of the general formula (XXIV)

(XXIV)

in which $R^5$, $R^6$, $R^{12}$ and

----- have the meaning indicated above and X is halogen denotes,
optionally in the presence of bases.

In this context, the acid function of the phenylamine is blocked in sistu as a silyl ester. Alternatively, the reaction can be carried out in a number of stages via the tert-butyl ester.

Bases are, for example, alkali metal carbonates, such as, for example, sodium or potassium carbonate, or sodium or potassium hydrogencarbonate, or organic bases such as trialkylamines, for example triethylamine, N-methylmorpholine, N-methylpiperidine, 4-dimethylaminopyridine or diisopropylethylamine.

Preferably, the reaction is carried out using diisopropylethylamine.

Suitable solvents in this context are inert organic solvents which do not change under the reaction conditions. These include halogenohydrocarbons such as dichloromethane or trichloromethane, hydrocarbon such as benzene, nitromethane, dioxane, dimethylformamide or acetonitrile. Likewise, it is possible to employ mixtures of the solvents. Dichloromethane is particularly preferred.

The compounds of the general formulae (XXIII) and (XXIV) are known or can be prepared from amino acids or carboxylic acids according to methods known from the literature.

The reactions described above are in general carried out in a temperature range from −78° C. up to reflux temperature, preferably from −78° C. to +20° C.

The reactions can be carried out at normal pressure, elevated pressure or at reduced pressure (e.g. from 0.5 to 5 bar). In general, they are carried out at normal pressure.

The active compound can act systemically and/or locally. For this purpose, it can be administered in a suitable manner, such as, for example, orally, parenterally, pulmonarily, nasally, sublingually, lingually, buccally, rectally, transdermally, conjunctivally, otically or as an implant.

For these routes of administration, the active compound can be administered in suitable administration forms.

For oral administration, known administration forms releasing the active compound rapidly and/or in modified form, such as, for example, tablets (noncoated and coated tablets, e.g. tablets provided with enteric coatings or film-coated tablets), capsules, coated tablets, granules, pellets, powders, emulsions, suspensions and solutions are suitable.

Parenteral administration can be carried out with circumvention of an absorption step (intravenous, intraarterial, intracardiac, intraspinal or intralumbar) or with involvement of an absorption (intramuscular, subcutaneous, intracutaneous, percutaneous, or intraperitoneal). For parenteral administration, suitable administration forms are, inter alia, injection and infusion preparations in the form of solutions, suspensions, emulsions, lyophilizates and sterile powders.

For the other routes of administration, for example, inhalation pharmaceutical forms (inter alia powder inhalers, nebulizers), nose drops/solutions, sprays; tablets or capsules to be administered lingually, sublingually or buccally, suppositories, aural and ophthalmic preparations, vaginal suppositories, aqueous suspensions (lotions, shake mixtures), lipophilic suspensions, ointments, creams, milk, pastes, dusting powder or implants are suitable.

The active compounds can be converted in a manner known per se to the administration forms mentioned. This is carried out using inert non-toxic, pharmaceutically suitable excipients. These include, inter alia, vehicles (e.g. microcrystalline cellulose), solvents (e.g. liquid polyethylene glycols), emulsifiers (e.g. sodium dodecyl sulfate), dispersants (e.g. polyvinylpyrrolidone), synthetic and natural biopolymers (e.g. albumin), stabilizers (e.g. antioxidants such as ascorbic acid), colorants (e.g. inorganic pigments such as iron oxides) or taste and/or odor corrigents.

In general, it has proven advantageous in the case of parenteral administration to administer amounts of approximately 5 to 250 mg/kg of bodyweight every 24 hours to achieve efficacious results. In the case of oral administration, the amount is approximately 5 to 100 mg/kg of bodyweight every 24 hours.

In spite of this, it can optionally be necessary to depart from the amounts mentioned, namely depending on the bodyweight, administration route, individual behavior toward the active compound, type of preparation and time or interval at which administration takes place.

Determination of the Minimum Inhibitory Concentration (MIC):

The MIC is determined in the liquid dilution test. Overnight cultures of the test microorganisms are diluted 1:5 000 or *S. aureus* 133 is diluted 1:10 000 in Müller Hinton broth (manufacturer: BBL) and incubated with dilutions of the test substances (dilution stages 1:2). Exceptions are the tests with *S. pyogenes* Wacker and *S. pneumoniae* 1707/4, which are carried out in Müller Hinton broth plus 20% bovine serum.

The cultures are incubated at 37° C. for 18-24 hours; enterococci and streptococci in the presence of 8-10% of $CO_2$.

Results:

The lowest substance concentration in each case at which visible bacterial growth no longer takes place is defined as the MIC. The MIC values in µg/ml of some compounds according to the invention compared with a series of test microorganisms are listed by way of example in the table below. The compounds show very good antibacterial action against most of the test microorganisms and thus a broad Gram-positive action.

| Ex. No. | *Staphylococcus aureus* 133 | *Enterococcus faecium* L 4001 | *Enterococcus faecalis* ICB 27159 | *Streptococcus pyogenes* Wacker | *Streptococcus pneumoniae* 1707/4 |
|---|---|---|---|---|---|
| 1 | 0.25 | <0.125 | <0.125 | 25 | <0.125 |
| 2 | 0.125 | <0.125 | <0.125 | 0.25 | <0.125 |
| 3 | 0.5 | <0.125 | <0.125 | 0.5 | <0.125 |
| 6 | <0.125 | <0.125 | <0.125 | 0.25 | 0.125 |
| 13 | 0.25 | <0.125 | <0.125 | <0.125 | <0.125 |
| 28 | 8 | 4 | 8 | 2 | 1 |
| 32 | 4 | 0.5 | 1 | 2 | 2 |
| 61 | 64 | 32 | 32 | 16 | 16 |
| 75 | 0.5 | <0.125 | <0.125 | 0.25 | <0.125 |
| 79 | 0.25 | <0.125 | <0.125 | 1 | 0.5 |
| 84 | 4 | 0.5 | 0.5 | 0.5 | 0.25 |
| 85 | 32 | 4 | 2 | 2 | 1 |

Systemic Infection with *S. aureus* 133

*S. aureus* 133 cells are cultured overnight in BH broth (Oxoid). The overnight culture was diluted 1:100 in fresh BH broth and spun at high speed for 3 hours. The bacteria in the logarithmic growth phase are centrifuged off and washed 2× with buffered, physiological saline solution. After this, a cell suspension in saline solution having an extinction of 50 units is adjusted in a photometer (Dr. Lange LP 2W). After a dilution step (1:15), this suspension is mixed 1:1 with a 10% strength mucin suspension. 0.25 ml/20 g mouse this infection solution are administered ip. This corresponds to a cell count of approximately 1×10E6 microorganisms/mouse. The ip therapy is carried out 30 minutes after the infection. For the infection experiment, female CFW1 mice are used. The survival of the animals is recorded over 6 days. The compounds according to the invention have a broad antibacterial spectrum, especially against gram-positive microorganisms. These properties make possible their use as chemotherapeutic active compounds in human and veterinary medicine. With their aid, it is possible to control gram-positive microorganisms, and to prevent, ameliorate and/or cure the diseases caused by these pathogens.

They are highly suitable for the prophylaxis and chemotherapy of local and systemic infections in human and veterinary medicine, which are caused by such pathogens.

| Abbreviations: | |
|---|---|
| aq. | aqueous |
| Bn | benzyl |
| Boc | Tert-Butoxycarbonyl |
| $CDCl_3$ | chloroform |
| CH | cyclohexane |
| DCM | dichloromethane |
| DMSO | dimethyl sulfoxide |
| DMAP | 4-N,N-dimethylaminopyridine |
| of th. | of theory |
| EDC | N'-(3-dimethylaminopropyl)-N-ethylcarbodiimide × HCl |
| EE | ethyl acetate |
| ESI | electrospray ionization (in MS) |
| sat. | Saturated |
| HATU | O-(7-azabenzotriazol-1-yl)-N,N,N',N'-tetramethyluronium hexafluorophosphate |
| HBTU | O-(benzotriazol-1-yl)-N,N,N',N'-tetramethyluronium hexafluorophosphate |
| HOBt | 1-hydroxy-1H-benzotriazole × $H_2O$ |
| h | hour |
| HPLC | high-pressure, high-performance liquid chromatography |
| LC-MS | liquid chromatography-coupled mass spectroscopy |
| MS | mass spectroscopy |
| MeOH | methanol |
| NMR | nuclear magnetic resonance spectroscopy |
| Pd/C | palladium/carbon |
| pc. | percent |
| $R_f$ | retention index (in TLC) |
| RT | room temperature |
| $R_t$ | retention time (in HPLC) |
| TPTU | 2-(2-oxo-1(2H)-pyridyl)-1,1,3,3-tetramethyluronium tetrafluoroborate |

HPLC Methods:

| A: | Column: | Kromasil C18 60 × 2 mm | |
|---|---|---|---|
| | Eluent: | A = 0.5% $HClO_4$ in water | |
| | | B = Acetonitrile | |
| | Gradient: | 0.0–0.5 min | 98% A |
| | | 4.5–6.5 min | 10% A |
| | | 6.7–7.5 min | 98% A |
| | Flow: | 0.75 ml/min | |
| | Temp.: | 30° C. | |
| | Detection: | 210 nm | |
| B: | Column: | Kromasil 100 C18 125 × 4 mm | |
| | Eluent: | A = 1.0% $HClO_4$ in water | |
| | | B = Acetonitrile | |
| | Gradient: | 0–1 min | 10% B |
| | | 1–9 min | 10% B–90% B |
| | | 9–13 min | 90% B |
| | Flow: | 2 ml/min | |
| | Temp.: | Room temp. | |
| | Detection: | 210 nm | |
| C: | Column: | Symmetry C18 RP C18 | |
| | Eluent: | A = 0.3 g 30% strength HCl in water | |
| | | B = Acetonitrile | |
| | Gradient: | 0 min | 98% A |
| | | 2.5 min | 5% A |
| | | 5 min | 5% A |

LC-MS Methods:

MHZ 2P

| Apparatus type MS: | Micromass Platform LCZ |  |  |  |
|---|---|---|---|---|
| | Ionization: ESI positive/negative |  |  |  |
| Apparatus type HPLC: | HP 1100 |  |  |  |
| | UV detector DAD: 208–400 nm |  |  |  |
| | Oven temp.: 40° C. |  |  |  |
| Column: | Symmetry C 18 |  |  |  |
| | 50 mm × 2.1 mm 3.5 µm |  |  |  |
| Gradient: | Time | A: % | B: % | Flow |
| | 0.00 | 10.0 | 90.0 | 0.50 |
| | 4.00 | 90.0 | 10.0 | 0.50 |
| | 6.00 | 90.0 | 10.0 | 0.50 |
| | 6.10 | 10.0 | 90.0 | 1.00 |
| | 7.50 | 10.0 | 90.0 | 0.50 |
| A: | Acetonitrile + 0.1% formic acid |  |  |  |
| B: | Water + 0.1% formic acid |  |  |  |

MHZ2Q

| Apparatus type MS: | Micromass Quattro LCZ |  |  |  |
|---|---|---|---|---|
| | Ionization: ESI positive/negative |  |  |  |
| Apparatus type HPLC: | HP 1100 |  |  |  |
| | UV detector DAD: 208–400 nm |  |  |  |
| | Oven temp.: 40° C. |  |  |  |
| Column: | Symmetry C 18 |  |  |  |
| | 50 mm × 2.1 mm 3.5 µm |  |  |  |
| Gradient: | Time | A: % | B: % | Flow |
| | 0.00 | 10.0 | 90.0 | 0.50 |
| | 4.00 | 90.0 | 10.0 | 0.50 |
| | 6.00 | 90.0 | 10.0 | 0.50 |
| | 6.10 | 10.0 | 90.0 | 1.00 |
| | 7.50 | 10.0 | 90.0 | 0.50 |
| A: | Acetonitrile + 0.1% formic acid |  |  |  |
| B: | Water + 0.1% formic acid |  |  |  |

SMKL-ZQ-1

Method MHZ-2P-01

Instrument: Micromass Platform LCZ, HP1100; column: Symmetry C18, 50 mm×2.1 mm, 3.5 µm; eluent A: water+0.05% formic acid, eluent b: acetonitrile+0.05% formic acid; gradient: 0.0 min 90% A→4.0 min 10% A→6.0 min 10% A; oven: 40° C.; flow: 0.5 ml/min; UV detection: 208-400 nm.

Method MHZ-2Q-01

Instrument: Micromass Quattro LCZ, HP1100; column: Symmetry C18, 50 mm×2.1 mm, 3.5 µm; eluent A: water+0.05% formic acid, eluent B: acetonitrile+0.05% formic acid; gradient: 0.0 min 90% A→4.0 min 10% A→6.0 min 10% A; oven: 40° C.; flow: 0.5 ml/min; UV detection: 208-400 nm.

Method SMKL-ZQ-1

Instrument: Waters Alliance 2790 LC; column: Symmetry C18, 50 mm×2.1, 3.5 µm; eluent A: water+0.0% formic acid, eluent B: acetonitrile+0.05% formic acid; gradient: 0.0 min 10% B→4.0 min 90% B→6.0 min 90% B→6.1 min 10% B; temperature: 50° C.; flow: 0.8 ml/min; UV detection: 210 nm.

EXAMPLE 1A (2-Oxo-2-phenyl-ethyl) (S)-2-benzyloxycarbonylamino-3-hydroxy-propionate

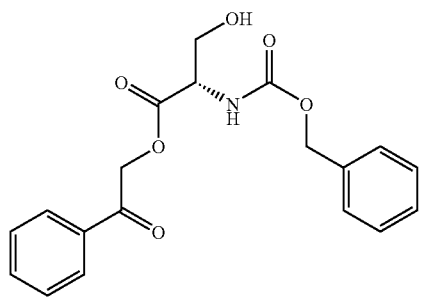

169.0 g (706 mmol) of Z-(L)-serine and 197 ml (1.41 mol) of triethylamine are added to 1.6 l of ethyl acetate at room temperature. In the course of 10 min, 154.7 g (777 mmol) of 2-bromoacetophenone are added. The reaction mixture is stirred at RT for 3 h. It is diluted with 2.4 l of ethyl acetate, extracted by shaking once with 2 l of 2N sulfuric acid, filtered from suspended matter, the organic phase is separated off and the aqueous phase is extracted twice with 500 ml each of ethyl acetate. The combined organic phases are washed with saturated sodium hydrogencarbonate solution, the aqueous phase is extracted with 800 ml of ethyl acetate and the combined organic phases are dried over sodium sulfate. After filtration, the solvent is removed in vacuo. The residue is dissolved in 3.0 l of hot ethyl acetate and cooled to RT in an ice bath. The deposited crystals are filtered off with suction, washed with a little diethyl ether and dried in a high vacuum. 124.5 g (49% of th.) of the product are obtained. The mother liquor is concentrated to one half, the precipitate is dissolved in the presence of heat and the solution is cooled to 0° C. After filtering off and drying, a further 30.6 g (12% of th.) of product are isolated. The remaining mother liquor is concentrated to dryness, and the residue is dissolved in 500 ml of hot ethyl acetate and again precipitated at 0° C. 17.0 g (7%) of the product, and after concentration and drying of the mother liquor, a further 38.8 g (15%) of the product, which is still 96 percent according to HPLC analysis, are obtained.

$R_f$(MeOH/dichloromethane 1/20)=0.54.

HPLC (method A): $R_t$=4.21 min.

MS (ESI pos): m/z=358 (M+H)$^+$, 380 (M+Na)$^+$, 715 (2M+H)$^+$, 737 (2M+Na)$^+$.

$^1$H-NMR (200 MHz, CDCl$_3$): δ=3.64 (dd, 1H), 3.91 (dt, 1H, $J_t$=11.0 Hz, $J_d$=3.2 Hz), 4.34 (m, 1H), 4.63 (m, 1H), 5.14 (s, 2H), 5.32 (d, 1H, J=16.7 Hz), 5.74 (d, 1H, J=16.4 Hz), 5.74-5.84 (m, 1H), 7.29-7.41 (m, 5H), 7.46-7.57 (m, 2H), 7.61-7.71 (m, 1H), 7.86-7.96 (m, 2H).

EXAMPLE 2A

2-[(S)-2-Benzyloxycarbonylamino-2-(2-oxo-2-phenyl-ethoxycarbonyl)-ethyl] 1-tert-butyl (S)-pyrrolidine-1,2-dicarboxylate

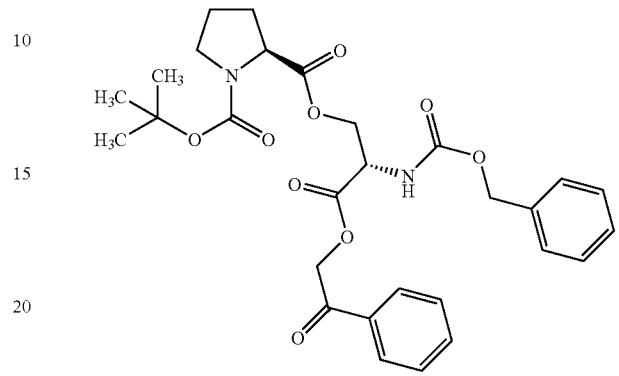

15.06 g of N-Boc-(L)-proline (69.96 mmol) and 25.00 g (69.96 mmol) of the serine ester from example 1A are dissolved in methylene chloride (250 ml) under argon. The solution is cooled to –20° C. and treated with 13.41 g of EDC (69.96 mmol) and 0.85 g of DMAP (7.00 mmol). The reaction solution is stirred at –20° C. for 1 h and then at room temperature for 48 h, evaporated and the residue is taken up in ethyl acetate. The solution is washed with aq. citric acid, aq. saturated sodium hydrogen-carbonate solution and aq. saturated sodium chloride solution. The organic phase is dried over sodium sulfate and evaporated. 32.47 g (84% of th.) of product are isolated after silica gel chromatography using toluene/ethyl acetate (5/1).

LC-MS: $R_t$=4.66 min;

MS (ESI+, method MHZ2P): m/z=577 (M+Na$^+$).

$^1$H-NMR (300 MHz, DMSO-d$_6$,): δ=1.85-2.3 (m, 4H), 3.25 (m, 2H), 4.4-4.8 (m, 4H), 5.1 (s, 2H), 5.5-5.8 (m, 2H), 7.3-8.1 (m, 10H), 8.9 (s, 1H).

EXAMPLE 3A (S)-2-[(S)-2-Benzyloxycarbonylamino-2-(2-oxo-2-phenyl-ethoxycarbonyl)-ethoxycarbonyl]pyrrolidinium chloride

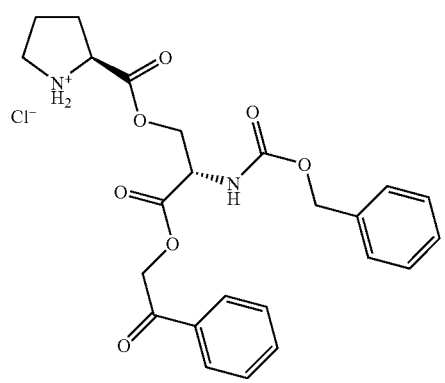

31.5 g (56.8 mmol) of the compound from example 2A are dissolved in 200 ml of 4M hydrogen chloride solution in dioxane under argon and stirred overnight at RT. The reaction solution is concentrated, and taken up once using ethyl acetate and concentrated again, and concentrated twice using dichloromethane. The residue is dissolved in ethanol (100 ml), diethyl ether (400 ml) is slowly added with stirring, the mixture is cooled and the precipitate is filtered off with suction. 25.2 g (86% of th.) of the product are obtained, which is reacted further without further purification.

LC-MS (method MHZ2P): $R_t$=2.84 min;
MS (ESI+): m/z=454 (M$^+$).

EXAMPLE 4A

Benzyl (S)-2-[(S)-2-(tert-butoxycarbonyl-methyl-amino)-propanoylamino]-propionate

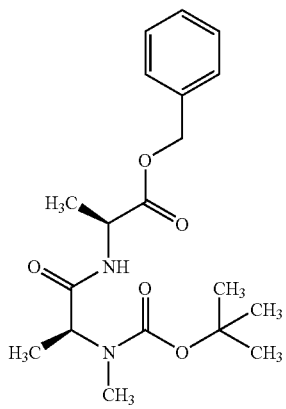

4.81 g (22.3 mmol) of L-alanine benzyl ester hydrochloride, 3.32 g (24.6 mmol) of HOBt and 4.92 g (25.7 mmol) of EDC are introduced into 10 ml of anhydrous dimethylformamide under argon. At 0° C., 4.54 g (22.3 mmol) of N-Boc-N-methyl-L-alanine and 14.7 ml (133.9 mmol) of N-methyl-morpholine are added, and the reaction mixture is stirred overnight with slow warming to RT. The reaction solution is treated with water and toluene and extracted with shaking. The aqueous phase is extracted twice with toluene, and the combined organic phases are dried over sodium sulfate and concentrated to dryness after filtration. The product is purified chromatographically by silica gel chromatography on about 1500 ml of silica gel using MeOH/dichloromethane 10/1. 7.9 g (97% of th.) of the product are obtained.

HPLC (method A): $R_t$=4.56 min.
MS (ESI pos): m/z=365 (M+H)$^+$, 387 (M+Na)$^+$.
$^1$H-NMR (300 MHz, CDCl$_3$): δ=1.34 (d, 3H), 1.40 (d, 3H), 1.48 (s, 9H), 2.78 (s, 3H), 4.52-4.73 (m, 2H), 5.15 (d, 1H), 5.19 (d, 1H), 6.57 (br. s, 1H), 7.29-7.41 (m, 5H).

EXAMPLE 5A

[(S)-1-((S)-1-Benzyloxycarbonyl-ethylcarbamoyl)-ethyl]-methyl-ammonium chloride

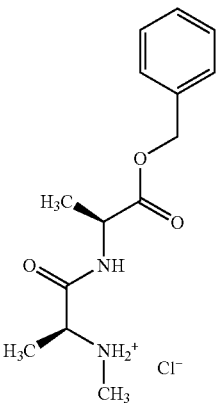

7.80 g (21.4 mmol) of the compound from example 4A are dissolved in 4N hydrogen chloride solution in dioxane (80 ml). After a few minutes, precipitate formation commences. The mixture is stirred for a further 1 h at RT, and the solid is filtered off with suction and washed with diethyl ether. After drying in vacuo, 5.96 g (93% of th.) of the product are obtained.

HPLC (method A): $R_t$=3.55 min.
MS (ESI pos): m/z=265 [(M−HCl)+H]$^+$.
$^1$H-NMR (300 MHz, DMSO-d$_6$): δ=1.36 (d, 6H), 2.45 (br. s, 3H), 3.80 (br. s, 1H), 4.40 (quint., 1H), 5.13 (s, 2H), 7.30-7.40 (m, 5H), 8.96 (br. s, 1H), 9.13 (d, 1H), 9.58 (br. s, 1H).

EXAMPLE 6A tert-Butyl (S)-2-{[(S)-1-((S)-1-benzyloxycarbonyl-ethylcarbamoyl)-ethyl]-methylcarbamoyl}-pyrrolidine-1-carboxylate

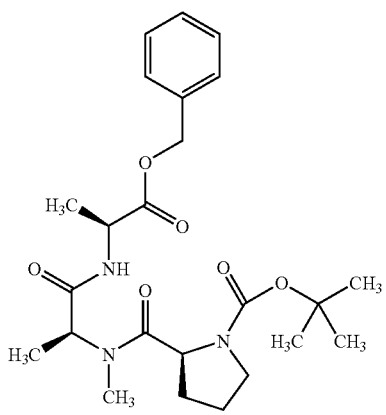

7.53 g (19.8 mmol) of HATU and 3.8 ml (21.8 mmol) of ethyldiisopropylamine are added under argon at 0° C. to a solution of 5.96 g (19.8 mmol) of the hydrochloride from example 5A and 4.27 g (19.8 mmol) of N-Boc-(L)-proline in anhydrous dimethylformamide (150 ml). After stirring with cooling for 30 min. in an ice bath, a further 7.6 ml (43.6 mmol) of ethyldiisopropylamine are added and the reaction mixture is stirred overnight with slow warming to RT. The reaction solution is treated with toluene and 10 pc. aqueous citric acid, extracted with shaking, the organic phase is again washed with aqueous citric acid solution, and the combined organic phases are extracted by shaking twice each with saturated aqueous sodium hydrogencarbonate solution and with water and dried over sodium sulfate. After the removal of the solvent in vacuo, the residue is taken up using dichloromethane and concentrated again. 9.14 g (98% of th.) of the product are obtained.

HPLC (method A): $R_t$=4.46 min.
MS (ESI pos): m/z=462 (N+H)$^+$, 484 (M+Na)$^+$.
$^1$H-NMR (300 MHz, CDCl$_3$): δ=1.31-1.48 (m, 15H), 1.73-2.26 (m, 4H), 2.76 (s, 2H), 2.96 (d, 1H), 3.37-3.69 (m, 2H), 4.47-4.66 (m, 2H), 4.76 (q, 0.66H), 5.04 (q, 0.33H), 5.07-5.25 (m, 2H), 6.62 (br. d, 0.33H), 7.29-7.37 (m, 5H), 8.45 (br. d, 0.66H).*
* amide isomerism

EXAMPLE 7A tert-Butyl (S)-2-{[(S)-1-((S)-1-carboxy-ethylcarbamoyl)-ethyl]-methyl-carbamoyl}-pyrrolidine-1-carboxylate

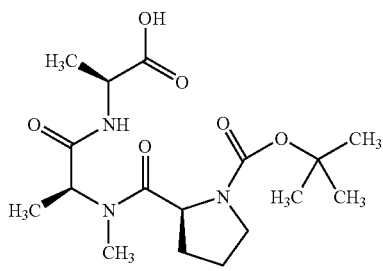

9.10 g (19.7 mmol) of the compound from example 6A are dissolved in methanol (100 ml), 1 g of 10 pc. palladium on activated carbon is added under argon and the mixture is then hydrogenated at a hydrogen pressure of 3 bar for 3 h at RT. The reaction solution is filtered off with suction through kieselguhr, which is washed with methanol and the solvent is removed in vacuo. 7.03 g (96% of th.) of the product are obtained as a colorless solid.

HPLC (method A): $R_t$=3.52 min.
MS (ESI pos): m/z=372 (M+H)$^+$, 394 (M+Na)$^+$, 765 (2M+Na)$^+$.
$^1$H-NMR (200 MHz, CDCl$_3$): δ=1.31-1.51 (m, 15H), 1.70-2.35 (m, 4H), 2.78 (s, 1.5H), 3.00 (d, 1.5H), 3.35-3.68 (m, 2H), 4.40-4.75 (m, 2H), 4.85 (q, 0.5H), 4.98 (q, 0.25H), 5.24 (q, 0.25H), 7.00 (br. t, 0.5H), 6.5-8.2 (br., 1H), 8.49 (br. d, 0.5H)*.
* amide isomerism

EXAMPLE 8A tert-Butyl (S)-2-{[(S)-1-((S)-2-{(S)-2-[(S)-2-benzyloxycarbonylamino-2-(2-oxo-2-phenyl-ethoxycarbonyl)-ethoxycarbonyl]-pyrrolidin-1-yl}-1-methyl-2-oxo-ethylcarbamoyl)-ethyl]-methyl-carbamoyl}-pyrrolidine-1-carboxylate

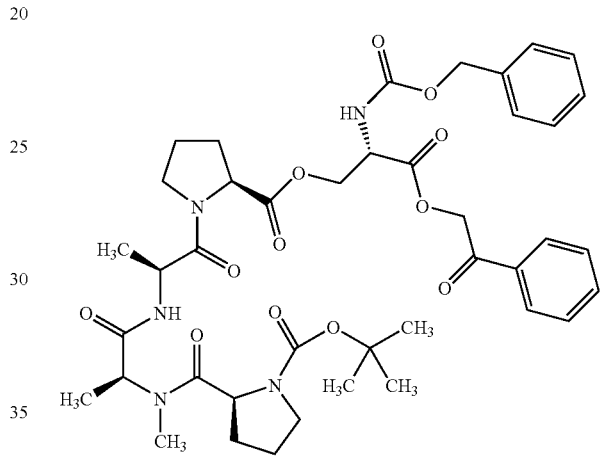

90.0 g (242 mmol) of the tripeptide from example 7A and 152.5 g (242 mmol) of the hydrochloride from example 3A are introduced together into dichloromethane (2.0 l) at −5° C. unter argon and 86.4 (291 mmol) of TPTU, 45.8 g (339 mmol) of HOBT and 118 ml (678 mmol) of ethyldiisopropylamine are added successively. The reaction mixture is stirred overnight with slow warming to RT. For working up, the mixture is concentrated, the residue is taken up in ethyl acetate, extracted by shaking twice with aqueous 10 pc. citric acid, twice with aqueous 10 pc. sodium hydrogencarbonate solution and once with saturated aqueous sodium chloride solution. The organic phase is dried over magnesium sulfate, filtered and concentrated to dryness. The residue is purified by chromatography on silica gel using ethyl acetate/ethanol 20/1. 162 g (83% of th.) of the product are obtained.

LC-MS (method MHZ2P): $R_t$=4.26 min; MS (ESI−): m/z=806 (M$^-$).
$^1$H-NMR (300 MHz, DMSO-d$_6$,): δ=1.1-1.4 (m, 13H), 1.5-2.3 (m, 10H), 2.5 (m, 1H), 2.7 (s, 2H), 2.85 (2, 2H), 3.2-3.65 (m, 4H), 3.95-5.1 (m, 10H), 5.5-5.6 (m, 2H), 7.25-8.0 (m, 10H).

EXAMPLE 9A tert-Butyl (S)-2-[((S)-1-{(S)-2-[(S)-2-((S)-2-benzyloxycarbonylamino-2-carboxyethoxycarbonyl)-pyrrolidin-1-yl]-1-methyl-2-oxo-ethylcarbamoyl}-ethyl)-methylcarbamoyl]-pyrrolidine-1-carboxylate

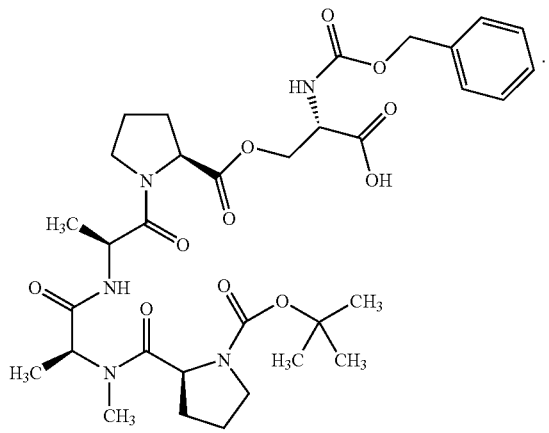

Under argon, are introduced into a solution of 17.0 g (21.0 mmol) of the compound from example 8A in 90 pc. aqueous acetic acid and 10.3 g (158 mmol) of zinc. The reaction mixture warms slightly and is cooled to 25° C. It is stirred at this temperature for 3 h and the mixture is subsequently filtered off with suction through kieselguhr and washed with ethyl acetate. The solvent is removed on a rotary evaporator, and the residue is taken up in ethyl acetate and extracted by shaking twice with 1N aqueous hydrochloric acid. The organic phase is concentrated again, treated three times with toluene and evaporated to dryness in vacuo and finally dried in vacuo. 14 g (94% of theory) are isolated. The product is reacted without further purification.

LC-MS (method MHZ2Q): $R_t$=3.62 min; MS (ESI+): m/z=689 (M+).

EXAMPLE 10A

Benzyl ((3S,7S,13S,16S,19S)-13,16,17-trimethyl-2,6,12,15,18-pentaoxo-5-oxa-1,11,14,17-tetraaza-tricyclo[17.3.0.0$^{7,11}$]docos-3-yl)-carbamate

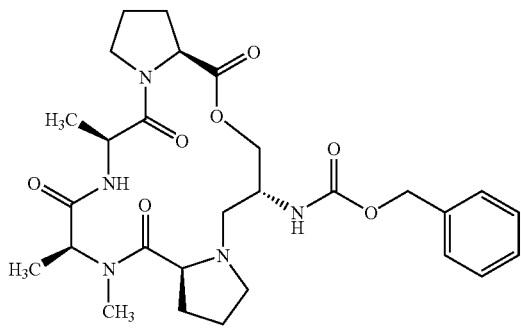

109.0 g (158 mmol) of the carboxylic acid from example 9A and 116.4 g (632 mmol) of pentafluorophenol are dissolved in 1000 ml of anhydrous dichloromethane, cooled to −20° C. and 39.4 g (205 mmol) of EDC are introduced. The reaction mixture is stirred overnight with slow warming to RT. The solvent is removed in vacuo and the residue is treated with hydrogen chloride in dioxane (600 ml) with ice cooling. The mixture is stirred at RT for 3 h, the solvent is removed in vacuo and the residue is taken up three times using toluene and again concentrated to dryness. The residue is divided into thirds and each part is treated as follows: The intermediate product is taken up in dichloromethane (900 ml) and introduced with a flow rate of 0.8 ml/min at RT into a vigorously stirred 2-phase mixture of 1.5 l of aqueous sodium hydrogencarbonate solution and 5 l of dichloromethane and stirred for about 2 h. The organic phase is separated off, the aqueous phase is extracted three times with 500 ml each of dichloromethane, and the combined organic phases are dried over sodium sulfate, filtered and concentrated to dryness.

The combined residues from the three reactions are purified by chromatography on silica gel using firstly ethyl acetate/cyclohexane 2/1, then pure ethyl acetate, then ethyl acetate/ethanol 20/1 and finally 10/1. 49.2 g (53% of th.) of the product are obtained. By repeated chromatography of an impure batch and taking up in ethyl acetate/dichloromethane, incomplete concentration and cooling, about a further 5 g (5%) of crystalline product are obtained.

LC-MS (method MHZ2Q): $R_t$=3.32 min;

MS (ESI+): m/z=571 (M+).

$^1$H-NMR (300 MHz, DMSO-d$_6$,): δ=1.4 (d, 3H), 1.5 (d, 3H), 1.9-2.4 (m, 9H), 3,5-3.85 (m, 5H), 4.2-4.2 (m, 1H), 4.5 (m, 1H), 4.75-5.25 (m, 5H), 5.64 (m, 1H), 7.3-7.4 (m, 5H), 8.3 (m, 1H).

EXAMPLE 11A (3S,7S,13S,16S,19S)-13,16,17-Trimethyl-2,6,12,15,18-pentaoxo-5-oxa-1,11,14,17-tetraaza-tricyclo[17.3.0.0$^{7,11}$]docos-3-yl-ammonium chloride

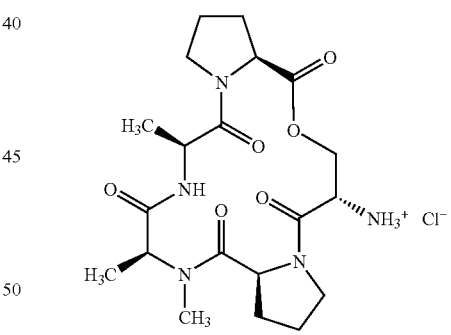

4.10 g (7.17 mmol) of the compound from example 11A are introduced into methanol (30 ml) under argon, treated with 8.6 ml (8.6 mmol) of 1N aqueous hydrochloric acid and 500 mg of 10 pc. palladium on activated carbon are added. The mixture is hydrogenated at normal pressure and RT for 2 h. The reaction mixture is filtered through kieselguhr, washed with methanol and concentrated to dryness. For working up, the residue is stirred with diethyl ether and filtered off with suction. 3.18 g (94% of th.) of the product are obtained, which is reacted without further purification.

LC-MS (method MHZ2Q): $R_t$=0.36 min.

HPLC (method B): $R_t$=1.95 min.

MS (ESI pos): m/z=438 [(M−HCl)+H]+, 875 [2×(M−HCl)+H]+.

EXAMPLE 12A tert-Butyl [(S)-2-(3,5-difluorophenyl)-1-((3S,7S,13S,16S,19S)-13,16,17-trimethyl-2,6,12,15,18-pentaoxo-5-oxa-1,11,14,17-tetraaza-tricyclo[17.3.0.0^{7,11}]docos-3-ylcarbamoyl)-ethyl]-carbamate

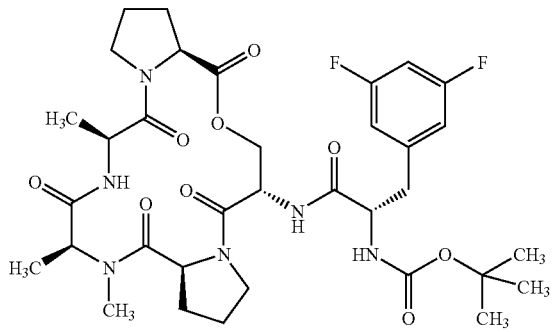

1.30 g (2.74 mmol) of the ammonium chloride from example 11A and 0.91 g (3.02 mmol) of N-Boc-3,5-difluoro-L-phenylalanine are dissolved in anhydrous dimethylformamide (6 ml) under argon and cooled in an ice bath. 1.15 g (3.02 mmol) of HATU and 0.525 ml (3.02 mmol) of ethyldiisopropylamine are added, and the reaction mixture is stirred at 0° C. for 30 min, before a further 1.05 ml (6.03 mmol) of ethyldiisopropylamine are added. The reaction mixture is stirred overnight with slow warming to RT. The reaction solution is purified directly by chromatography in 3 fractions by means of preparative RP-HPLC using acetonitrile/water (gradient). 1.13 g (57% of th.) of the product are obtained.

LC-MS (method MHZ2P): $R_t$=4.03 min; MS (ESI+): m/z=720 (M+).

HPLC (method A): $R_t$=4.51 min.

MS (ESI pos): m/z=721 (M+H)+, 743 (M+Na)+.

$^1$H-NMR (400 MHz, CDCl$_3$): δ=1.40 (d, 3H), 1.42 (s, 9H), 1.52 (d, 3H), 1.88-2.40 (m, 8H), 2.82 (s, 3H), 2.87 (dd, 1H), 3.06 (dd, 1H), 3.50-3.71 (m, 4H), 3.76 (m, 1H), 4.27 (q, 1H), 4.48-4.56 (m, 2H), 4.77 (q, 1H), 4.84-4.94 (m, 2H), 5.17 (m, 1H), 5.84 (br. d, 1H), 6.66 (br. t, 1H), 6.73-6.80 (m, 2H), 6.90 (br. d, 1H), 8.51 (br. d, 1H).

The reaction can alternatively be carried out in dichloromethane and the product purified by means of silica gel chromatography using dichloromethane/methanol, then ethyl acetate.

EXAMPLE 13A (S)-2-(3,5-Difluorophenyl)-1-((3S,7S,13S,16S,19S)-13,16,17-trimethyl-2,6,12,15,18-pentaoxo-5-oxa-1,11,14,17-tetraaza-tricyclo[17.3.0.0^{7,11}]docos-3-ylcarbamoyl)-ethylammonium 2,2,2-trifluoroacetate

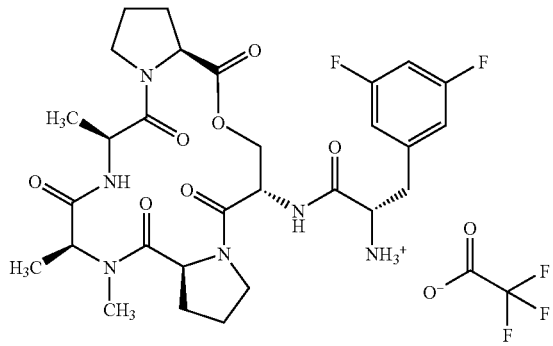

2.12 g (2.94 mmol) of the carbamate from example 12A are dissolved in dichloromethane (32 ml) and cooled to 0° C. Subsequently, a mixture of water and trifluoroacetic acid (1/9) (32 ml) is added, and the mixture is stirred at 0° C. for 45 min. and then evaporated. 2.83 g of crude product are obtained, which after taking up in toluene and dichloromethane and subsequent concentration is reacted further.

LC-MS (method MHZ2Q): $R_t$=2.33 min;

MS (ESI+): m/z=620 (M+)

EXAMPLE 14A 3-(3,5-Difluorophenyl)-2-((E)-hept-2-enoylamino)-propionic acid

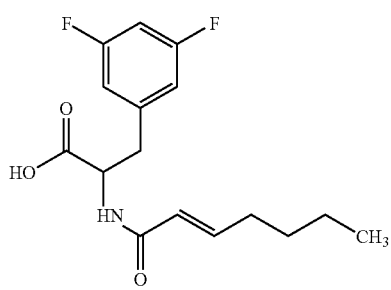

6.3 ml (49.7 mmol) of chlorotrimethylsilane are added to a solution of 5.0 g (24.9 mmol) of 3,5-difluoro-DL-phenylalanine in dichloromethane (150 ml) and the reaction mixture is heated to reflux for 1 h. After cooling to 0° C., 9.7 ml (55.9 mmol) of ethyldiisopropylamine are added slowly and then, dropwise, 3.64 g (24.9 mmol) of trans-2-heptenoyl chloride. The reaction mixture is stirred overnight with slow warming to RT and remains standing at RT for 2 days. For working up, it is evaporated to dryness in vacuo, the residue is taken up using diethyl ether and extracted with 2.5 pc. aqueous sodium hydrogencarbonate solution (250 ml). The aqueous phase is extracted twice with ether, and the combined organic phases are extracted a further three times with sodium hydrogencarbonate solution. The combined aqueous phases are brought to pH=2 using 1N aqueous hydrochloric acid and extracted three times with ethyl acetate. The combined ethyl acetate phases are dried over sodium sulfate, filtered, and the solvent is concentrated in vacuo. The residue is washed by stirring with diethyl ether and filtered. The filter residue is isolated, the filtrate is concentrated and again treated with diethyl ether. After repetition twice, a total of 6.12 g (79% of th.) of product are obtained as a colorless solid.

HPLC (method A): $R_t$=4.30 min.

MS (ESI pos): m/z=312 (M+H)+, 334 (M+Na)+, 623 (2M+H)+, 645 (2M+Na)+.

$^1$H-NMR (200 MHz, CDCl$_3$): δ=0.91 (t, 3H), 1.20-1.53 (m, 4H), 2.20 (br. q, 2H), 3.14 (dd, 1H), 3.28 (dd, 1H), 4.92 (br. q, 1H), 5.80 (br. d, 1H, Jd=15.4 Hz), 5.99 (br. d, 1H), 6.63-6.79 (m, 3H), 6.91 (dt, 1H, Jd=15.3 Hz, Jt=6.9 Hz), 7.5-9.0 (br., 1H).

EXAMPLE 15A 1-tert-Butyl 2-methyl (2S,4R)-4-(toluyl-4-sulfonyloxy)-pyrrolidine-1,2-dicarboxylate

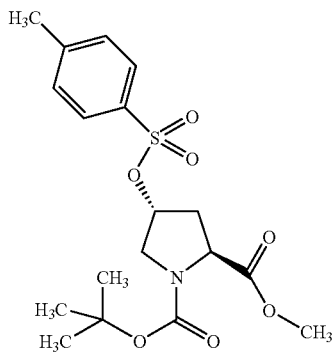

20.0 g (81.5 mmol) of trans-N-Boc-L-hydroxyproline methyl ester are introduced into 75 ml of dichloromethane unter argon, 26.4 ml (326 mmol) of pyridine are added and, at 0° C., 31.1 g (163 mmol) of p-toluenesulfonyl chloride in dichloromethane (75 ml) are added. The reaction mixture is stirred overnight with slow warming to RT and allowed to stand at RT for 2 days. For working up, the mixture is extracted by shaking with water, and the organic phase is dried over sodium sulfate, filtered and concentrated to dryness. The residue is purified by chromatography on silica gel using ethyl acetate/cyclohexane 1/5. 30.1 g (92% of th.) of the product are obtained as a colorless solid.

$R_f$(ethyl acetate/cyclohexane 1/1)=0.56.

LC-MS (MHZ2P): $R_t$=4.30 min.

MS (ESI pos): m/z=400 (M+H)$^+$, 422 (M+Na)$^+$, 821 (2M+Na)$^+$.

$^1$H-NMR (200 MHz, CDCl$_3$): δ=1.39+1.42 (2×s, 9H), 2.05-2.24 (m, 1H), 2.33-2.62 (m, 1H), 2.46 (s, 3H), 3.56-3.65 (m, 2H), 3.72 (s, 3H), 4.37 (q, 1H), 4.97-5.11 (m, 1H), 7.36 (d, 2H), 7.79 (d, 2H).

EXAMPLE 16A 1-tert-Butyl (2S,4R)-4-(toluyl-4-sulfonyloxy)-pyrrolidine-1,2-dicarboxylate

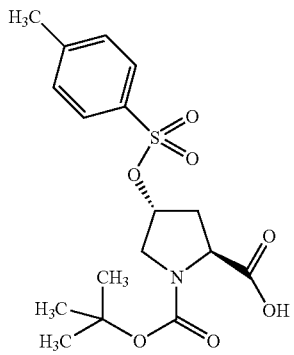

25.0 g (62.6 mmol) of methyl ester from example 15A are dissolved in acetonitrile/water 3/1 and treated with 10.5 g (250 mmol) of lithium hydroxide hydrate. The reaction mixture is stirred overnight at RT. For the removal of the acetonitrile, the solution is concentrated in vacuo. 50 ml of 5N aqueous hydrochloric acid are added to the aqueous solution, pH=3 is adjusted using 1N aqueous hydrochloric acid and the mixture is extracted three times using ethyl acetate. The combined organic phases are dried over sodium sulfate, filtered and the solvent is removed in vacuo. 21.0 g (87% of th.) of the product are obtained as a colorless solid. The $^1$H-NMR spectroscopic characterization indicates a proportion of about 20% of the diastereomeric compound.

HPLC (method A): $R_t$=4.23 min.

MS (DCI-NH$_3$): m/z=403 (M+NH$_4$)$^+$.

$^1$H-NMR (400 MHz, CDCl$_3$): δ=1.48 (s, 9H), 2.23-2.31 (m, 1H), 2.47 (s, 3H), 2.55 (m, 1H), 3.49 (dd, 1H), 3.81 (br. d, 1H), 4.47 (t, 1H), 4.98 (br. m, 1H), 7.38 (d, 2H), 7.79 (d, 2H).

Signals of the diastereomeric impurity: δ=1.42 (s), 2.60 (br. m), 3.56 (br. m), 3.66 (br. d), 4.41 (br. t), 5.03 (br.).

Alternatively, the synthesis can be carried out via the proline benzyl ester and a hydrogenolysis using palladium on carbon.

EXAMPLE 17A 1-tert-Butyl (2S,4R)-4-methyl-pyrrolidine-1,2-dicarboxylate

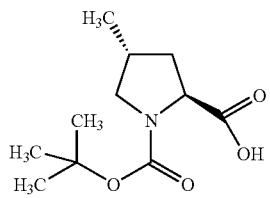

11.0 g (123 mmol) of copper(I) cyanide in a heated flask under argon are introduced into anhydrous tetrahydrofuran (110 ml) at −78° C. 153 ml of 1.6 M methyllithium solution in diethyl ether are added dropwise, and the solution is warmed to 0° C. and stirred at this temperature for 10 min. After cooling to −78° C., 18.9 g (49.0 mmol) of the tosylate from example 16A in anhydrous tetrahydrofuran (110 ml) are slowly added. The tosylate is dried beforehand by taking up in toluene and evaporating again. After addition has taken place, the colorless, slightly turbid reaction mixture is cooled to −20° C. and stirred for 3 h with slow warming to 0° C. The reaction is ended at −20° C. by addition of saturated aqueous ammonium chloride solution (150 ml) and the mixture is stirred overnight with warming to RT. After acidifying to pH=3 using 5N aqueous hydrochloric acid, it is extracted three times with ethyl acetate. The combined organic phases are extracted by shaking with saturated aqueous sodium chloride solution, dried over sodium sulfate, filtered, and the solvent is removed in vacuo. The residue is taken up using dichloromethane and filtered again. The evaporation of the filtrate in vacuo affords 11.8 g of the crude product as a viscous oil. The compound is employed in the next reaction without further purification.

LC-MS (MHZ2Q): $R_t$=3.32 min.

MS (ESI neg): m/z=228 (M−H)$^+$.

$^1$H-NMR (200 MHz, CDCl$_3$): δ=1.06 (d, 3H), 1.43+1.49* (2×s, 9H), 1.55-2.04 (br. m, 1H), 2.04-2.57 (br. m, 2H), 2.80-3.06 (br. m, 1H), 3.45-3.82 (br. m, 1H), 4.16-4.50 (br. m, 1H).

* intensity ratio about 1:2.

EXAMPLE 18A

2-[(S)-2-Benzyloxycarbonylamino-2-(2-oxo-2-phenyl-ethoxycarbonyl)-ethyl]1-tert-butyl (2S,4R)-4-methyl-pyrrolidine-1,2-dicarboxylate

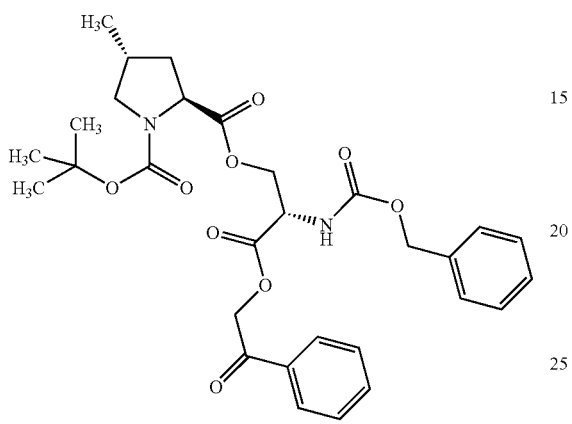

11.8 g (≦49.0 mmol) of the crude product from example 17A and 17.5 g (49.0 mmol) of phenacyl ester from example 1A are introduced into dichloromethane (140 ml) at 0° C. and 0.6 g (4.9 mmol) of DMAP and 9.4 g (49.0 mmol) of EDC are added. The reaction mixture is stirred overnight with slow warming to RT. For working up, it is extracted by shaking with water and dichloromethane, the organic phase is washed twice with 0.1N aqueous hydrochloric acid and the organic phase is extracted by shaking with saturated NaCl solution. The aqueous phases are reextracted once each with dichloromethane. The combined organic phases are dried over sodium sulfate, filtered and concentrated in vacuo. The residue is purified by chromatography on silica gel using ethyl acetate/cyclohexane 1/4 to 1/2. 19.3 g (69% of th.) of the product are obtained.

$R_f$(ethyl acetate/cyclohexane 1/1)=0.58.

HPLC (method A): $R_t$=5.09 min.

MS (ESI pos): m/z=569 (M+H)$^+$, 591 (M+Na)$^+$, 469 [(M−Boc)+H]$^+$.

$^1$H-NMR (300 MHz, CDCl$_3$): δ=0.95-1.07 (m, 3H), 1.33-1.48 (m, 9H), 1.53-1.67+1.73-1.89 (2×m, 0.25H+0.75H), 2.08-2.26 (m, 1H), 2.26-2.48 (m, 1H), 2.83-3.02 (m, 1H), 3.58-3.78 (m, 1H), 4.16-4.26+4.27-4.39 (2×m, 0.2H+0.8H), 4.48-4.71 (m, 2H), 4.79-4.90 (m, 1H), 5.07-5.20 (m, 2H), 5.37 (dd, 1H, J$_1$=16.2 Hz, J$_2$=3.6 Hz), 5.49 (dd, 1H, J$_1$=16.4 Hz, J$_2$=2.1 Hz), 5.32-5.54 (br. 0.25H), 5.57 (br. q, 0.25H), 5.97 (br. d, 0.38H), 6.45H (br. d, 0.12H), 7.29-7.40 (m, 5H), 7.45-7.55 (m, 2H), 7.58-7.67 (m, 1H), 7.84-7.93 (m, 2H).

EXAMPLE 19A (2S,4R)-2-[(S)-2-Benzyloxycarbonylamino-2-(2-oxo-2-phenyl-ethoxycarbonyl)-ethoxycarbonyl]-4-methyl-pyrrolidinium chloride

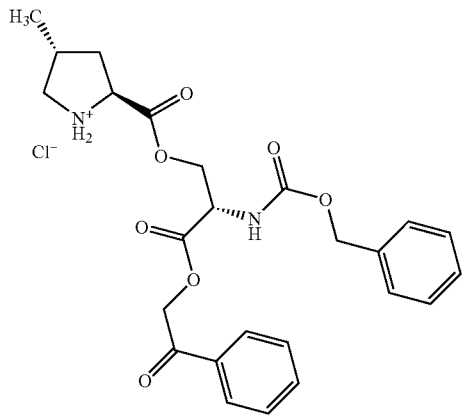

92 ml (366 mmol) of 4N hydrogen chloride solution in dioxane are added to 16 g (28.1 mmol) of the compound from example 18A. The reaction mixture is stirred at RT for 1 h and the solvent is removed in vacuo. The residue is taken up twice using dichloromethane and concentrated to dryness. 15.1 g of crude product are obtained as a pale yellow hard foam, which still contains about 4% by weight of dioxane. The crude product is reacted further without further purification.

LC-MS (MHZ2Q): $R_t$=2.91 min.

MS (ESI pos): m/z=469 [(M−HCl)+H]$^+$.

$^1$H-NMR (300 MHz, DMSO-d$_6$,): δ=1.03-1.08 (m, 3H), 1.76 (br. q, 0.25H), 1.93 (m, 0.75H), 2.38-2.52 (m, 2H), 2.95 (br. m, 1H), 3.65 (br. m, 1H), 4.42-4.61 (m, 2H), 4.78-4.95 (m, 2H), 5.13 (t*, 2H), 5.32 (d, 0.75H), 5.40 (d, 0.25H), 5.56 (d, 1H), 7.01 (br. d, 0.75H), 7.12 (br. d, 0.25H), 7.27-7.41 (m, 5H), 7.45-7.53 (m, 2H), 7.57-7.65 (m, 1H), 7.87 (br. d, 1.5H), 7.91 (br. d, 0.5H), 8.81 (br. s, 0.66H), 9.08 (br. s, 0.33H), 11.05 (br. s, 0.33H), 11.20 (br. s, 0.66H).

* AB system intensity ratio: 1:12:1

EXAMPLE 20A tert-Butyl (S)-2-((S)-1-benzyloxycarbonyl-ethylcarbamoyl)-piperidine-1-carboxylate

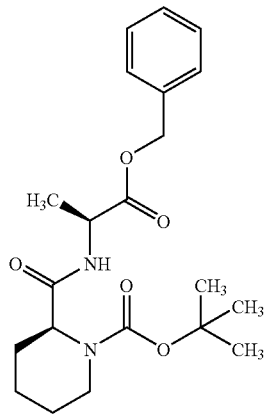

9.85 g (45.57 mmol) of alanine benzyl ester, 6.79 g of HOBT (50.23 mmol) and 10.07 g (52.52 mmol) of EDC are introduced into dimethylformamide (30 ml) at 0° C., treated with 10.47 g (45.67 mmol) of N-Boc-pipecolic acid. and 27.71 g (274 mmol) of N-methylmorpholine and stirred overnight at room temperature. Subsequently, the mixture is treated with water and toluene, the phases are separated and the organic phase is washed with sat. aqueous sodium chloride solution. 14.9 g (83% of th.) of product are isolated by means of silica gel chromatography using cyclohexane/ethyl acetate 10/1.

LC-MS (method MHZ2P): $R_t$=4.40 min;
MS (ESI+): m/z=390 (M$^+$)
$^1$H-NMR (300 MHz, DMSO-d$_6$,): δ=1.48-1.65 (m, 17H), 2.2-2.3 (m, 1H), 2.7-2.8 (m, 1H), 3.9-4.1 (m, 1H), 4.52-4.8 (m, 2H), 5.15 (m, 2H), 6.6 (m, 1H), 7.3-7.4 (m, 5H).

EXAMPLE 21A (S)-2-((S)-1-Benzyloxycarbonyl-ethylcarbamoyl)-piperidinium chloride

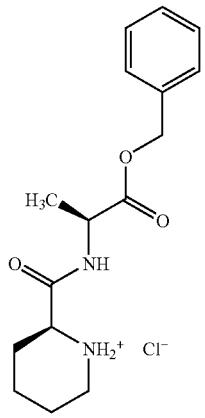

2.30 g (5.89 mmol) of the carbamate from example 20A are dissolved in 4N hydrochloric acid in dioxane (23 ml) and stirred at room temperature for 1 h. The solution is subsequently evaporated, taken up again in toluene and concentrated again. The residue is washed with diethyl ether with stirring and filtered off with suction. 1.70 g (88% of th.) of product are obtained, which is employed in the following reaction without further purification.

LC-MS (method MHZ2Q): $R_t$=1.76 min;
MS (ESI+): m/z=290 (M$^+$).

EXAMPLE 22A tert-Butyl (S)-2-{1-[(S)-2-((S)-1-benzyloxycarbonyl-ethylcarbamoyl)-piperidin-1-yl]-methanoyl}-pyrrolidine-1-carboxylate

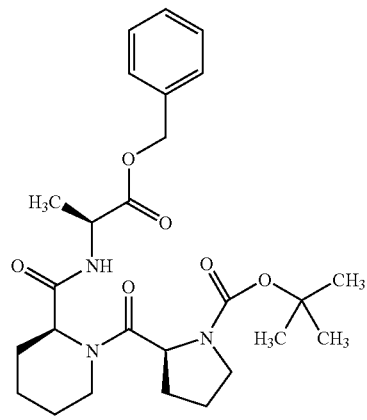

12.27 g (37.54 mmol) of the hydrochloride from example 21A and 10.50 g (48.81 mmol) of N-Boc-L-proline are dissolved in methylene chloride (30 ml) and cooled to 0° C. Subsequently, the solution is treated with 18.56 g (48.81 mmol) of HATU and 5.82 g (45.05 mmol) of ethyldiisopropylamine and stirred at 0° C. for 30 min. After further addition of 11.64 g (90.10 mmol) of ethyldiisopropylamine, the mixture is stirred at room temperature for 72 h and then evaporated. The residue is taken up using ethyl acetate and the solution is washed with aq. citric acid and aq. sodium hydrogencarbonate solution and sat. aq. sodium chloride solution, dried over sodium sulfate and evaporated. The residue is purified by means of silica gel chromatography using cyclohexane/ethyl acetate 5/1. 18.25 g (99% of th.) of product are obtained.

LC-MS (method MHZ2Q): $R_t$=4.30 min;
MS (ESI+): m/z=487 (M+Na$^+$).

EXAMPLE 23A tert-Butyl (S)-2-{1-[(S)-2-((S)-1-carboxy-ethylcarbamoyl)-piperidin-1-yl]-methanoyl}-pyrrolidine-1-carboxylate

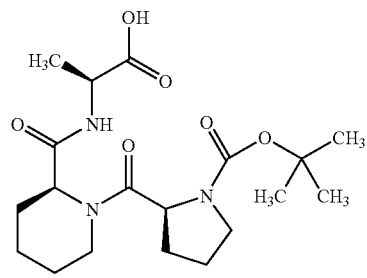

A solution of 10.00 g (20.51 mmol) of the ester from example 22A in methanol (100 ml) is treated with Pd/C (1.00 g) (10 pc.) and hydrogenated at RT at a hydrogen pressure of 1 bar. Subsequently, the solution is filtered through silica gel and evaporated. 7.93 g (97% of th.) of the product are obtained, which is reacted without further purification.

LC-MS (method MHZ2P): R$_t$=3.16 min;

MS (ESI+): m/z=397 (M+).

$^1$H-NMR (300 MHz, DMSO-d$_6$): δ=1.45-1.58 (m, 15H), 1.6-1.75 (m, 2H), 1.78-2.0 (m, 2H), 2.05-2.2 (m, 2H), 2.4-2.6 (m, 2H), 3.05-3.2 (m, 1H), 3.38-3.6 (m, 2H).

EXAMPLE 24A tert-Butyl (S)-2-{1-[(S)-2-((S)-2-{(2S,4R)-2-[(S)-2-benzyloxycarbonylamino-2-(2-oxo-2-phenylethoxy-carbonyl)-ethoxycarbonyl]-4-methyl-pyrrolidin-1-yl}-1-methyl-2-oxo-ethylcarbamoyl)-piperidin-1-yl]-methanoyl}-pyrrolidine-1-carboxylate

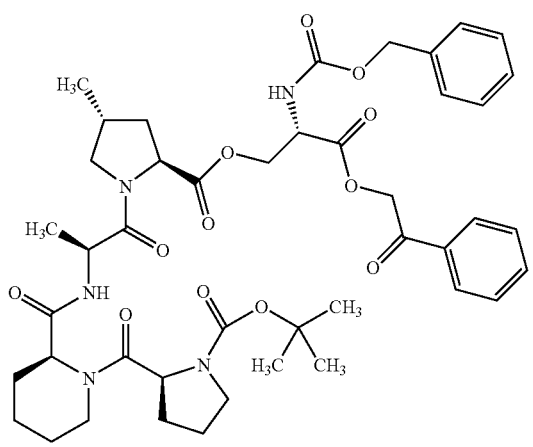

3.12 g (6.18 mmol) of the hydrochloride from example 19A and 2.46 g (6.18 mmol) of the tripeptide acid from example 23A are introduced into dichloromethane (40 ml) at −0° C. unter argon and 1.17 g (8.65 mmol) of HOBT, 2.20 g (7.41 mmol) of TPTU and 3.0 ml (17.4 mmol) of ethyldiiso-propylamine are added successively. The reaction mixture is stirred overnight with slow warming to RT. For working up, it is concentrated, and the residue is taken up in ethyl acetate and extracted by shaking with saturated aqueous sodium hydrogencarbonate solution. The organic phase is washed with 0.1 N hydrochloric acid, water and saturated aqueous sodium chloride solution, the organic phase is dried over sodium sulfate, filtered and the solvent is removed in vacuo. 5.8 g (71% of th.) of the product is obtained as a hard pale yellow foam, which is employed in the following reaction without further purification.

LC-MS (MHZ2P): R$_t$=4.59 min.

HPLC (method A): R$_t$=4.81 min.

MS (ESI pos): m/z=848 (M+H)$^+$, 870 (M+Na)$^+$.

$^1$H-NMR (400 MHz, CDCl$_3$): δ=1.00-1.13 (m, 3H), 1.25-1.34 (m, 3H), 1.34-1.48 (m, 11H), 1.58-1.70 (m, 3H), 1.75-2.57 (m, 8H), 2.95-3.19 (m, 2H), 3.29-3.82 (m, 4H), 4.30-4.75 (m, 5H), 4.77-4.84 (m, 1H), 5.09-5.21 (m, 3H), 5.26-5.55 (m, 2.33H), 5.74-5.81 (m, 0.66H), 6.64 (dd, 0.66H), 7.29-7.41 (m, 5H), 7.45-7.55 (m, 2H), 7.59-7.66 (m, 1H), 7.85-7.94 (m, 2H), 8.41-8.53 (m, 0.33H).

EXAMPLE 25A tert-Butyl (S)-2-[1-((S)-2-{(S)-2-[(2S,4R)-2-((S)-2-benzyloxycarbonylamino-2-carboxy-ethoxycarbo-nyl)-4-methyl-pyrrolidin-1-yl]-1-methyl-2-oxo-ethylcarbamoyl}-piperidin-1-yl)-methanoyl]-pyrrolidine-1-carboxylate

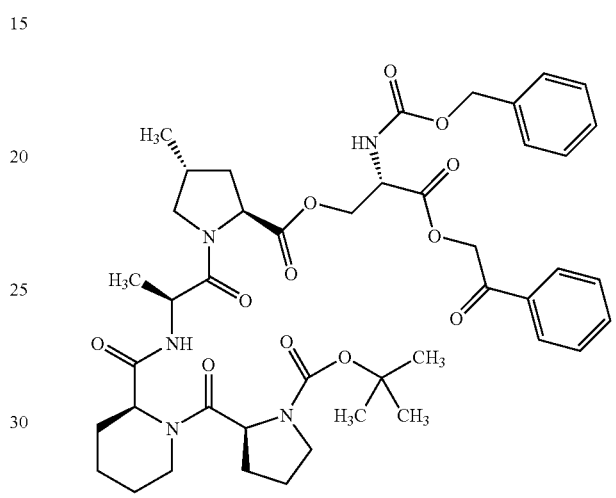

5.17 g (6.1 mmol) of the phenacyl ester from example 24A are dissolved in 90 pc. aqueous acetic acid (60 ml) and treated with 2.99 g (45.8 mmol) of zinc powder. The reaction mixture is stirred at RT for 2 h. The reaction solution is filtered off through kieselguhr and washed with ethyl acetate. The organic phase is concentrated in vacuo (not to dryness), the residue is extracted by shaking with ethyl acetate and 1N hydrochloric acid, and the phases are separated. The aqueous phase is extracted with ethyl acetate, and the combined organic phases are dried over sodium sulfate, filtered and concentrated to dryness. The residue is taken up twice in toluene and evaporated in vacuo. The residue is taken up in diethyl ether, extracted by shaking with saturated aqueous sodium hydrogencarbonate solution and the aqueous phase is washed again with diethyl ether. The aqueous phase is subsequently adjusted to pH 2.7 using 5N hydrochloric acid and extracted twice with ethyl acetate. The combined organic extracts are dried over sodium sulfate, filtered and the solvent is removed in vacuo. 4.01 g (91% of th.) of the product are obtained as a hard foam.

LC-MS (MHZ2P): R$_t$=4.02 min.

MS (ESI pos): m/z=730 (M+H)$^+$, 752 (M+Na)$^+$.

MS (ESI neg): m/z=728 (M−H)$^-$.

$^1$H-NMR (400 MHz, CDCl$_3$): δ=1.02-1.11 (m, 3H), 1.23-1.34 (m, 3H), 1.35-1.44 (m, 6H), 1.46 (br. d, 3H), 1.51-1.76 (br. m, 4H), 1.77-2.41 (br. m, 7H), 2.41-2.55 (m, 1H), 3.00 (dd, 0.66H), 3.07-3.23 (m, 1H), 3.32-3.90 (m, 4H), 4.14-4.21 (br. m, 0.5H), 4.31-4.38 (br. m, 0.66H), 4.39-4.86 (m, 5H), 5.08-5.19 (m, 3H), 5.20-5.28 (m, 0.5H), 5.82-5.93 (m, 1H), 7.00 (dd, 0.4H), 7.29-7.40 (m, 5H), 8.01-8.06 (m, 0.2H).

EXAMPLE 26A

Benzyl ((3S,9S,13S,15R,19S,22S)-15,19-dimethyl-2,8,12,18,21-pentaoxo-11-oxa-1,7,17,20-tetraaza-tetracyclo[20.4.0.0³,⁷.0¹³,¹⁷]hexacos-9-yl)-carbamate

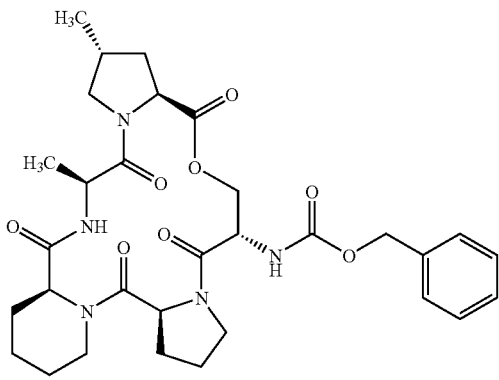

3.95 g (5.41 mmol) of the acid from example 25A and 3.98 g (21.65 mmol) of pentafluorophenol are dissolved in dichloromethane (13 ml) and cooled to −20° C. under argon. 1.14 g (5.95 mmol) of EDC are added, and the reaction mixture is stirred overnight with slow warming to RT. The reaction solution is concentrated to dryness and the residue is treated at 0° C. with 4N hydrogen chloride solution in dioxane (80 ml). The mixture is stirred for 3 h and the solvent is subsequently removed in vacuo. The residue is dissolved in dichloromethane (about 900 ml) and slowly added dropwise at RT to a vigorously stirred two-phase mixture of 1N aqueous sodium hydrogencarbonate solution (700 ml) and dichloromethane (1200 ml). The reaction mixture is stirred overnight. The phases are separated, the aqueous phase is extracted three times with dichloromethane and the combined organic phases are dried over sodium sulfate, filtered and concentrated to dryness. The residue (2.7 g of yellow hard foam) is purified by chromatography in 3 portions by means of preparative RP-HPLC using acetonitrile/water (gradient). 1.98 g (60% of th.) of the product are obtained.

LC-MS (MHZ2P): $R_t$=3.74 min.
MS (ESI pos): m/z=612 (M+H)⁺.
MS (ESI neg): m/z=610 (M−H)⁻.
¹H-NMR (400 MHz, CDCl₃): δ=1.08 (d, 3H), 1.24-1.51 (m, 3H), 1.42 (d, 3H), 1.58-1.65 (br. d, 1H), 1.71-1.78 (br. m, 1H), 1.86 (m, 1H), 1.91-2.01 (m, 2H), 2.06-2.20 (m, 1H), 2.10 (dd, 1H), 2.30-2.42 (m, 1H), 2.45-2.61 (m, 2H), 2.73 (br. d, 1H), 3.22 (dd, 1H), 3.55 (dt, 1H, $J_d$=11.5 Hz, $J_t$=7.1 Hz), 3.62 (dd, 1H, $J_1$=9.7 Hz, $J_2$=11.7 Hz), 3.71 (dd, 1H, $J_1$=8.8 Hz, $J_2$=11.8 Hz), 3.78 (m, 1H), 4.21 (dt, 1H, $J_d$=1.2 Hz, $J_t$=9.7 Hz), 4.47-4.55 (br. m, 2H), 4.69 (br. s, 1H), 4.80 (dd, 1H, $J_1$=11.6 Hz, $J_2$=1.2 Hz), 5.02 (m, 1H), 5.08 (q*, 2H), 5.19 (dd, 1H), 5.60 (br. d, 1H), 7.28-7.40 (m, 5H), 8.32 (br. d, 1H).
* AB system, intensity ratio about 1:12:12:1

EXAMPLE 27A (3S,9S,13S,15R,19S,22S)-15,19-Dimethyl-2,8,12,18,21-pentaoxo-11-oxa-1,7,17,20-tetraaza-tetracyclo[20.4.0.0³,⁷.0¹³,¹⁷]hexacos-9-yl-ammonium chloride

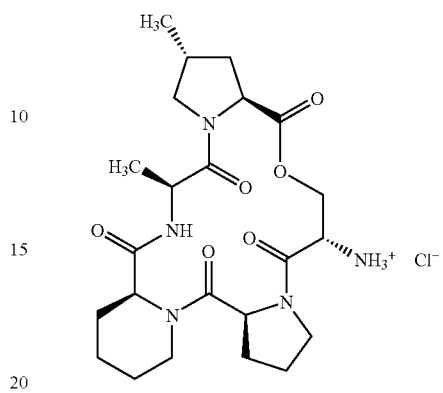

1.45 g (2.37 mmol) of the benzyl carbamate-protected cyclic system from example 26A are introduced into methanol (60 ml) under argon, 1N hydrochloric acid (2.8 ml) is added and the mixture is treated with 320 mg of 10% palladium on activated carbon. The mixture is hydrogenated at normal pressure for 2 h at RT. The reaction mixture is filtered through kieselguhr, washed with methanol and the filtrate is concentrated. 1.2 g (98% of th.) of the product are obtained, which is employed in the subsequent reaction without further purification.

LC-MS (method A): $R_t$=3.44 min.
MS (ESI pos): m/z=478 [(M−HCl)+H]⁺.
¹H-NMR (400 MHz, CDCl₃): δ=1.07 (d, 3H), 1.20-1.80 (m, 6H), 1.42 (d, 3H), 1.88 (m, 1H), 1.80-2.12 (m, 4H), 2.13-2.29 (br. m, 1H), 2.40 (m, 1H), 2.45-2.67 (br. m, 2H), 2.75 (br. m, 1H), 3.08-3.28 (br. m, 1H), 3.55-3.67 (br. m, 1H), 3.67-4.04 (br. m, 4H), 4.49 (br. d, 1H), 4.55 (d, 1H), 4.61 (br. d, 2H), 4.72-5.20 (br. m, 2H).

EXAMPLE 28A tert-Butyl [(S)-2-(3,5-difluorophenyl)-1-((3S,9S,13S,15R,19S,22S)-15,19-dimethyl-2,8,12,18,21-pentaoxo-11-oxa-1,7,17,20-tetraaza-tetracyclo-[20.4.0.0³,⁷.0¹³,¹⁷]hexacos-9-ylcarbamoyl)-ethyl]-carbamate

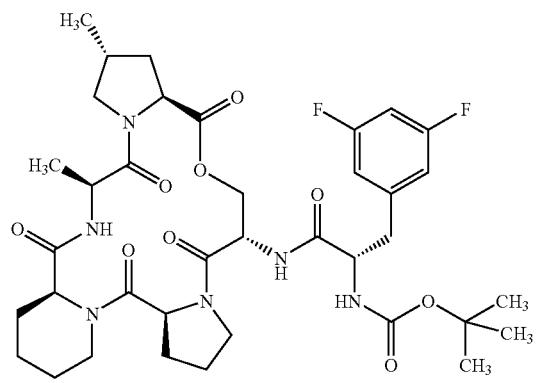

337 mg (0.89 mmol) of HATU and 0.138 ml (0.78 mmol) of ethyldiisopropylamine are added under argon at 0° C. to a solution of 350 mg (0.68 mmol) of the hydrochloride from example 27A and 267 mg (0.89 mmol) of N-Boc-L-3,5-difluorophenylalanine in anhydrous dimethylformamide (2 ml). After stirring for 30 min., a further 0.277 ml (1.56 mmol) of ethyldiisopropylamine are added, and the reaction mixture is stirred overnight with slow warming to RT. The reaction solution is employed directly in a preparative RP-HPLC using acetonitrile/water as the eluent. After the chromatographic purification, 505 mg (97% of th.) of the product are obtained.

HPLC (method A): $R_t$=4.62 min.

MS (ESI pos): m/z=761 (M+H)$^+$, 783 (M+Na)$^+$, $^1$H-NMR (400 MHz, CDCl$_3$): δ=1.09 (d, 3H), 1.36-1.49 (m, 14H), 1.65 (br. d, 1H), 1.72-1.80 (br. m, 1H), 1.83-2.01 (m, 3H), 2.08-2.19 (m, 2H), 2.30-2.51 (m, 2H), 2.64 (dt, 1H, $J_d$=2.4 Hz, $J_t$=13.4 Hz), 2.72 (br. d, 1H), 2.85 (dd, 1H), 3.07 (dd, 1H), 3.16 (dd, 1H), 3.50-3.65 (m, 2H), 3.72-3.87 (m, 2H), 4.25 (br. q, 1H), 4.51 (dt, 1H, $J_d$=1.3 Hz, $J_t$=9.9 Hz), 4.56 (d, 1H), 4.61-4.70 (br. m, 2H), 4.83 (br. d, 1H), 4.99 (m, 1H), 5.13 (m, 1H), 5.84 (br. d, 1H), 6.62-6.71 (m, 2H), 6.72-6.79 (m, 2H), 6.84 (br. d, 1H), 8.58 (br. d, 11H).

EXAMPLE 29A (S)-2-(3,5-Difluorophenyl)-1-((3S,9S,13S,15R,19S,22S)-15, 19-Dimethyl-2,8,12,18,21-pentaoxo-11-oxa-1,7,17,20-tetraaza-tetracyclo[20.4.0.0$^{3,7}$.0$^{13,17}$] hexacos-9-ylcarbamoyl)-ethylammonium 2,2,2-trifluoroacetate

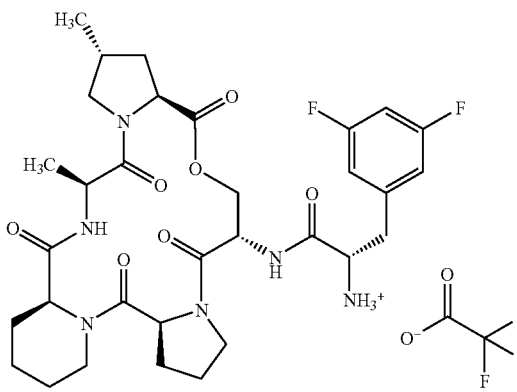

485 mg (0.64 mmol) of the compound from example 28A are introduced into dichloromethane (7 ml) at 0° C. 7 ml of a solution of 9 parts by volume of trifluoroacetic acid and 1 part of water are added and the reaction mixture is stirred for 45 min. The solvent is removed in vacuo and the residue is in each case taken up using dichloromethane and subsequently using toluene and concentrated to dryness. 588 mg of crude product are obtained, which is employed in the subsequent step without further purification.

Alternatively, the reaction can also be carried out in dichloromethane.

LC-MS (MHZ2P): $R_t$=2.70 min.

MS (ESI pos): m/z=661 [(M-TFA)+H]$^+$.

MS (ESI neg): m/z=659 [(M-TFA)–H]$^-$.

$^1$H-NMR (400 MHz, CDCl$_3$): δ=1.02 (d, 3H), 1.26 (d, 3H), 1.31-1.55 (m, 4H), 1.63-1.89 (m, 4H), 1.91-2.03 (m, 2H), 2.04-2.19 (m, 2H), 2.32-2.51 (m, 2H), 2.60 (br. t, 1H), 2.67-2.75 (br. m, 1H), 2.97 (dd, 1H), 3.10-3.25 (m, 2H), 3.47-3.57 (m, 1H), 3.60-3.87 (m, 4H), 4.30 (br. t, 1H), 4.44 (br. t, 1H), 4.53 (d, 1H), 4.62-4.70 (br. m, 2H), 4.77 (d, 1H), 4.96 (m, 1H), 5.11 (m, 1H), 6.72 (m, 1H), 6.77-6.85 (m, 2H), 7.86 (br. s, 1H), 8.23 (br. d, 1H).

EXAMPLE 30A

3-Cylcohexyl-2-propenoic acid

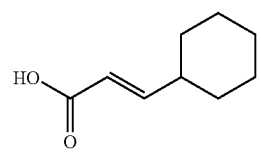

3.34 g (32.1 mmol) of malonic acid are dissolved in pyridine (10 ml), after the weakly exothermic reaction has subsided 3.0 g (26.7 mmol) of cyclohexanecarbaldehyde and 0.23 g (2.7 mmol) of piperidine are added, and the reaction mixture is heated to reflux for 4 h. The cooled reaction solution is added to a mixture of ice and concentrated hydrochloric acid, the aqueous phase is extracted three times with diethyl ether, the combined organic phases are dried over sodium sulfate, filtered, and the solvent is removed in vacuo. 4.42 g of product are obtained, which is reacted further without purification.

HPLC (method A): $R_t$=4.21 min.

MS (ESI pos): m/z=155 (M+H)$^+$, 177 (M+Na)$^+$.

$^1$H-NMR (200 MHz, CDCl$_3$): δ=1.02-1.45 (m, 5H), 1.59-1.87 (m, 5H), 2.06-2.28 (m, 1H), 5.77 (dd, 1H, $J_1$=15.8 Hz, $J_2$=1.1 Hz), 7.03 (dd, 1H, $J_1$=15.8 Hz, $J_2$=6.8 Hz), 11.7 (br.s, 1H).

EXAMPLE 31A

3-Cylcohexyl-2-propenoyl chloride

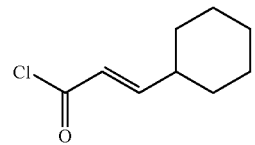

4.22 g (27.3 mmol) of 3-cylcohexyl-2-propenoic acid are suspended in dichloromethane (30 ml), 5 drops of DMF are added and at RT 1.9 ml (164 mmol) of thionyl chloride are slowly added dropwise. The reaction mixture is heated to reflux for 2 h, cooled and concentrated to dryness on a rotary evaporator. The oily residue is taken up twice using toluene, concentrated to dryness and dried in vacuo. 4.72 g of product are obtained, which is directly reacted further.

EXAMPLE 32A

N-[(2E)-3-Cyclohexyl-2-propenoyl]-3,5-difluorophenylalanine

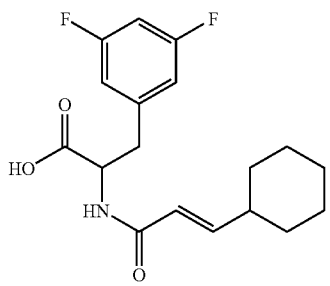

6.3 ml (49.7 mmol) of chlorotrimethylsilane are added to a solution of 5.0 g (24.9 mmol) of 3,5-difluoro-DL-phenylalanine in dichloromethane (150 ml) and the reaction mixture is heated to reflux for 1 h. After cooling to 0° C., 9.7 ml (55.9 mmol) of ethyldiisopropylamine are slowly added and then, dropwise, 4.29 g (24.9 mmol) of trans-3-cyclohexyl-2-propenoyl chloride. The reaction mixture is stirred overnight with slow warming to RT and remains standing at RT for two days. For working up, the mixture is evaporated to dryness in vacuo, the residue is taken up using diethyl ether and extracted with 2.5 pc. aq. sodium hydrogencarbonate solution (250 ml). The aqueous phase is extracted twice with diethyl ether. The combined organic phases are extracted a further three times with sodium hydrogencarbonate solution. The combined aqueous phases are brought to pH=2 using 1N aqueous hydrochloric acid and extracted three times with ethyl acetate. The combined ethyl acetate phases are dried over sodium sulfate, filtered, and the solvent is concentrated in vacuo. The residue (4.63 g) is washed by stirring with diethyl ether and filtered. 3.64 g (43% of th.) of colorless solid are obtained. The residue from the concentrated mother liquor and the residue from the concentrated diethyl ether phase of the alkaline extraction (see above), are taken up together in ethyl acetate and extracted with 1N hydrochloric acid. The organic phase is dried over sodium sulfate, filtered and concentrated. The residue is washed by stirring with diethyl ether and filtered off with suction. A further 2.18 g (26%) of product are isolated.

PREPARATION EXAMPLES

Example 1

(E)-Hept-2-enoic acid [(S)-2-(3,5-difluorophenyl)-1-((3S,7S,13S,16S,19S)-13,16,17-trimethyl-2,6,12,15,18-pentaoxo-5-oxa-1,11,14,17-tetraazatricyclo[17.3.0.0$^{7,11}$]docos-3-ylcarbamoyl)-ethyl]-amide

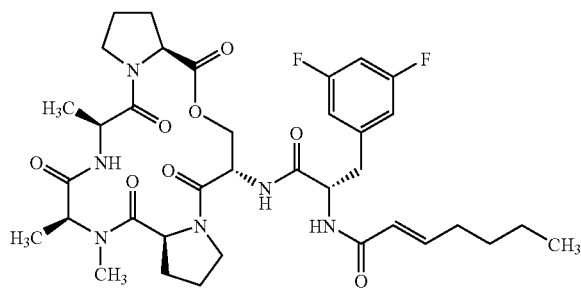

2.89 g (2.75 mmol) of the compound from example 13A and 458.8 mg (3.58 mmol) of trans-2-heptenoic acid are introduced into dichloromethane (20 ml), cooled to 0° C., then treated with 2.09 g (5.51 mmol) of HATU and 462.7 mg (3.58 mmol) of ethyldiisopropylamine. The solution is stirred at 0° C. for 30 min, then a further 925.3 mg (7.16 mmol) of ethyldiisopropylamine are added, and it is stirred at room temperature for 18 h. The reaction solution is evaporated, and the residue is taken up using ethyl acetate and washed with aq. citric acid, aq. sodium hydrogencarbonate solution and sat. aq. sodium chloride solution, dried over sodium sulfate, filtered and concentrated to dryness. The residue is chromatographed on silica gel using ethyl acetate/cyclohexane 1/2. 1.51 g (56% of th.) of the product are obtained.

LC-MS (method MHZ2Q): R$_t$=4.32 min;

MS (ESI+): m/z=731 (MH$^+$).

HPLC (method A): R$_t$=4.54 min.

MS (ESI pos): m/z=731 (M+H)$^+$, 753 (M+Na)$^+$.

$^1$H-NMR (400 MHz, CDCl$_3$): δ=0.90 (t, 3H), 1.28-1.39 (m, 5H), 1.40-1.48 (m, 2H), 1.53 (d, 3H), 1.85-2.06 (m, 5H), 2.09-2.26 (m, 4H), 2.30-2.41 (m, 1H), 2.83 (s, 3H), 2.96 (d, 2H), 3.32 (m, 1H), 3.50-3.67 (m, 3H), 3.77 (m, 1H), 4.45-4.54 (m, 2H), 4.62 (q, 1H), 4.77 (q, 1H), 4.84 (dd, 1H, J$_1$=11.7 Hz, J$_2$=1.7 Hz), 4.89 (dq, 1H), 5.15 (dd, 1H), 6.18 (dt, 1H, J$_d$=15.3 Hz, J$_t$=1.5 Hz), 6.63 (br. d, 1H), 6.67 (tt, 1H, J$_1$=9.1 Hz, J$_2$=2.3 Hz), 6.75 (m, 2H), 6.88-7.00 (m, 2H), 8.46 (br. d, 1H).

Alternatively, firstly the acyl-phenylalanine side chain can be constructed analogously to example 14A (see below). The hydrochloride from example 11A is then reacted with this acid to give the amide. In this case, the target compound example 1 must still be separated off from the (R)-phenylalanine epimers.

Example 2

(E)-Hept-2-enoic acid [(S)-2-(3,5-difluorophenyl)-1-((3S,9S,13S,15R,19S,22S)-15,19-Dimethyl-2,8,12,18,21-pentaoxo-11-oxa-1,7,17,20-tetraaza-tetracyclo[20.4.0.0$^{3,7}$.0$^{13,17}$]hexacos-9-ylcarbamoyl)-ethyl]-amide

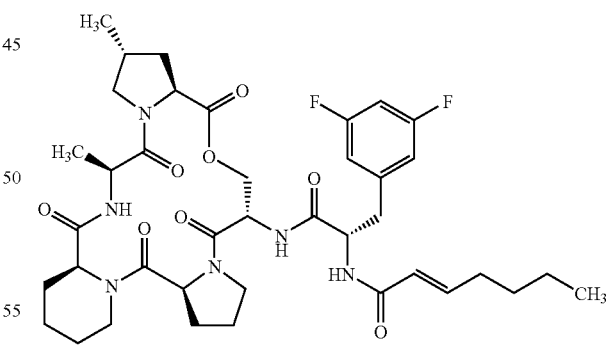

101.5 mg (0.13 mmol) of the compound from example 29A and 23.0 mg (0.17 mmol) of trans-2-heptenoic acid are introduced under argon into anhydrous dimethylformamide (2 ml) at 0° C. and then 65.0 mg (0.17 mmol) of HATU and 0.025 ml (0.14 mmol) of ethyldiisopropylamine are added. After 30 min, a further 0.05 ml (0.29 mmol) of ethyldiisopropylamine are added to the reaction mixture. The reaction mixture is stirred overnight with slow warming to RT. The reaction solution is subjected directly to an RP-HPLC using acetonitrile/water as eluent. In the course of this, 63 mg (62% of th.) of a colorless solid are obtained.

HPLC (method A): $R_t$=4.90 min.

MS (ESI pos): m/z=771 (M+H)$^+$.

$^1$H-NMR (400 MHz, CDCl$_3$): δ=0.98 (t, 3H), 1.02 (d, 3H), 1.29-1.53 (m, 10H), 1.66 (br. d, 1H), 1.73-1.87 (m, 2H), 1.91-2.02 (m, 2H), 2.05-2.18 (m, 2H), 2.22 (br. q, 2H), 2.31-2.48 (m, 2H), 2.63 (br. t, 1H), 2.71 (br. d, 1H), 2.90-3.00 (m, 2H), 3.10 (dd, 1H), 3.48-3.59 (m, 3H), 3.76 (m, 1H), 4.46-4.54 (m, 2H), 4.63 (dt, 1H), 4.65-4.73 (m, 2H), 4.80 (dd, 1H, $J_1$=11.8 Hz, $J_2$=1,5 Hz), 4.98 (dq, 1H), 5.11 (dd, 1H), 6.19 (dt, 1H, $J_d$=15.4 Hz, $J_t$=1.5 Hz), 6.60 (br. d, 1H), 6.66 (tt, 1H, $J_1$=9.0 Hz, $J_2$=2.2 Hz), 6.70-6.76 (m, 2H), 6.90-7.00 (m, 2H), 8.50 (br. d, 1H).

Example 3

3-Cylcohexylpropanoic acid [(S)-2-(3,5-difluorophenyl)-1-((3S,9S,13S,15R,19S,22S)-15,19-Dimethyl-2,8,12,18,21-pentaoxo-11-oxa-1,7,17,20-tetraaza-tetracyclo[20.4.0.0$^{3,7}$.0$^{13,17}$] hexacos-9-ylcarbamoyl)-ethyl]-amide

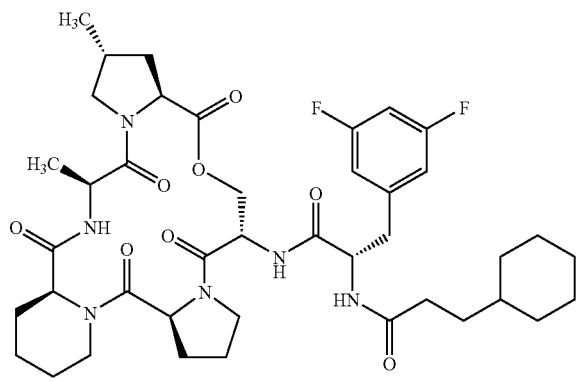

100 mg (0.13 mmol) of the compound from example 29A and 22.0 mg (0.14 mmol) of 3-cyclohexylpropionic acid are introduced under argon into anhydrous dimethylformamide (1 ml) at 0° C. and then 54.0 mg (0.14 mmol) of HATU and 0.025 ml (0.14 mmol) of ethyldiisopropylamine are added. After 30 min, a further 0.05 ml (0.29 mmol) of ethyldiisopropylamine are added to the reaction mixture. The reaction mixture is stirred overnight with slow warming to RT. The reaction solution is subjected directly to an RP-HPLC using acetonitrile/water as eluent. In the course of this, 50 mg (49% of th.) of a colorless solid are obtained.

HPLC (method A): $R_t$=5.14 min.

MS (ESI pos): m/z=799 (M+H)$^+$, 821 (M+Na)$^+$.

$^1$H-NMR (400 MHz, CDCl$_3$): δ=0.84-0.98 (m, 2H), 1.05 (d, 3H), 1.10-1.30 (m, 4H), 1.37 (d, 3H), 1.35-1.80 (m, 12H), 1.80-1.89 (m, 1H), 1.92-2.03 (m, 2H), 2.04-2.20 (m, 2H), 2.31-2.52 (m, 4H), 2.63 (br. t, 1H), 2.72 (br. d, 1H), 2.89 (dd, 1H), 2.95 (dd, 1H), 3.15 (dd, 1H), 3.48-3.59 (m, 3H), 3.77 (m, 1H), 4.44-4.55 (m, 3H), 4.64-4.73 (br. d, 2H), 4.80 (br. d, 1H), 4.97 (m, 1H), 5.11 (dd, 1H, $J_1$=8.7 Hz, $J_2$=2.8 Hz), 6.43 (br. d, 1H), 6.67 (tt, 1H, $J_1$=9.0 Hz, $J_2$=2.2 Hz), 6.71-6.76 (m, 2H), 6.84 (br. d, 1H), 8.47 (br. d, 1H).

Example 4

3-Cyclohexyl-2-propenoic acid [(S)-2-(3,5-difluorophenyl)-1-((3S,9S,13S,15R,19S,22S)-15,19-Dimethyl-2,8,12,18,21-pentaoxo-11-oxa-1,7,17,20-tetraaza-tetracyclo [20.4.0.0$^{3,7}$.0$^{13,17}$] hexacos-9-ylcarbamoyl)-ethyl]-amide

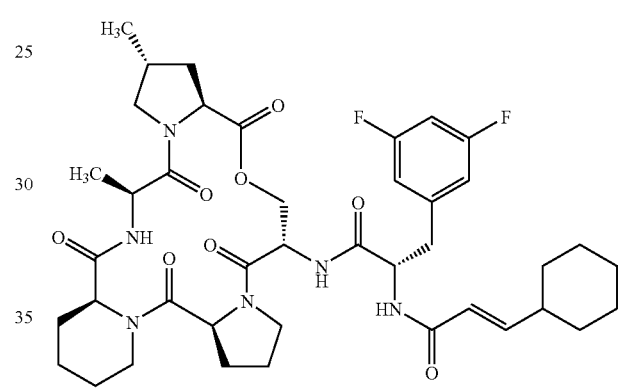

152 mg (0.30 mmol) of the ammonium chloride from example 27A and 110 mg (0.33 mmol) of the acid from example 32A are introduced under argon into anhydrous dimethylformamide (1 ml) at 0° C. and then 124 mg (0.33 mmol) of HATU and 0.057 ml (0.11 mmol) of ethyldiisopropylamine are added. After 30 min a further 0.113 ml (0.22 mmol) of ethyldiisopropylamine are added to the reaction mixture. The reaction mixture is stirred overnight with slow warming to RT. The reaction solution is subjected directly to an RP-HPLC using acetonitrile/water as eluent. In the course of this, 104 mg (44% of th.) of product and 71 mg (30% of th.) of epimer are isolated.

HPLC (method A): $R_t$=5.31 min.

MS (ESI pos): m/z=797 (M+H)$^+$.

$^1$H-NMR (200 MHz, CDCl$_3$): δ=1.02 (d, 3H), 1.08-1.30 (m, 5H), 1.37 (d, 3H), 1.30-1.57 (m, 4H), 1.60-1.88 (m, 7H), 1.88-2.28 (m, 5H), 2.28-2.52 (m, 2H), 2.52-2.82 (m, 2H), 2.84-3.05 (m, 2H), 3.11 (dd, 1H), 3.44-3.66 (m, 3H), 3.68-3.85 (m, 1H), 4.42-4.58 (m, 2H), 4.61-4.86 (m, 4H), 4.98 (m, 1H), 5.12 (br. d, 1H), 6.16 (br. d, 1H, J=15.4 Hz), 6.58-6.79 (m, 3H), 6.80-7.02 (m, 3H), 8.52 (d, 1H).

Epimer:

HPLC (method A): $R_t$=5.31 min.

MS (ESI pos): m/z=797 (M+H)$^+$, 819 (M+Na)$^+$.

| Ex. No. | Structure | HPLC/LCMS method | Retention time | Mass peak | Mass found |
|---|---|---|---|---|---|
| 5 | 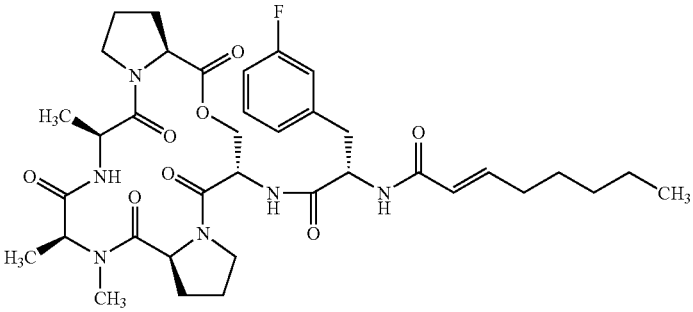 | MHZ2Q | 4.5 | M+ | 726 |
| 6 | 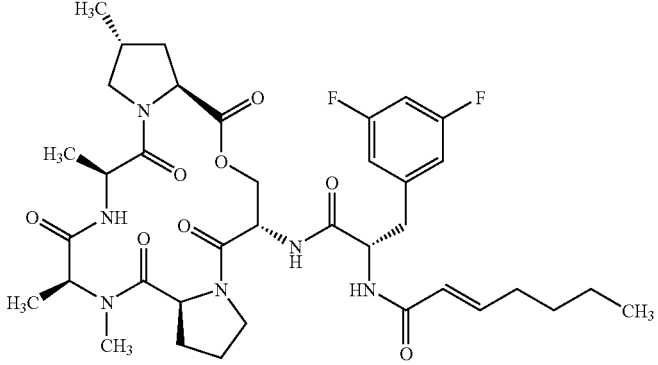 | MHZ2P | 4.46 | M− | 743 |
| 7 | 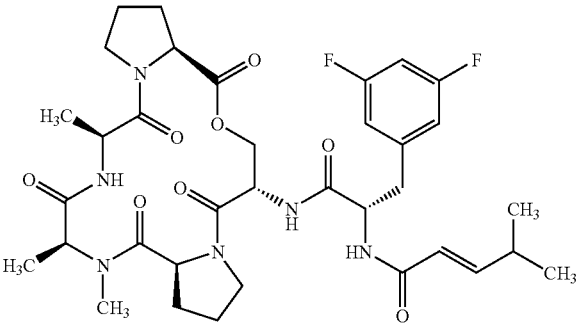 | A | 4.49 | M+ | 716 |
| 8 | 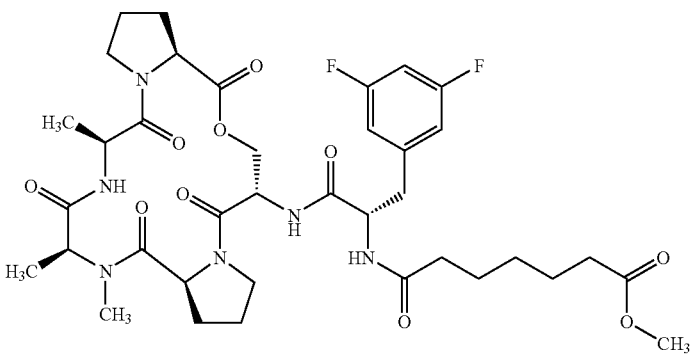 | MHZ2Q | 3.8 | M+ | 776 |

-continued

| Ex. No. | Structure | HPLC/LCMS method | Retention time | Mass peak | Mass found |
|---|---|---|---|---|---|
| 9 | 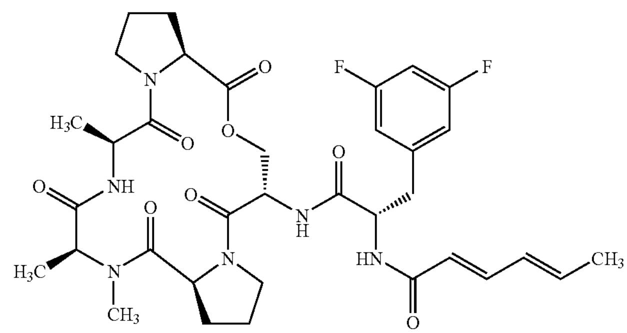 | MHZ2Q | 4.0 | M+ | 714 |
| 10 | 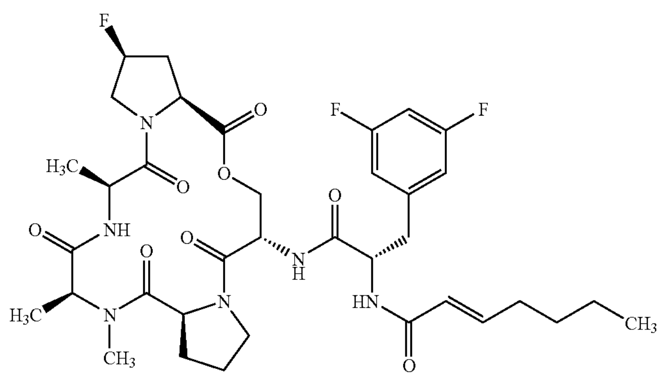 | A | 4.56 | MH+ | 749 |
| 11 | 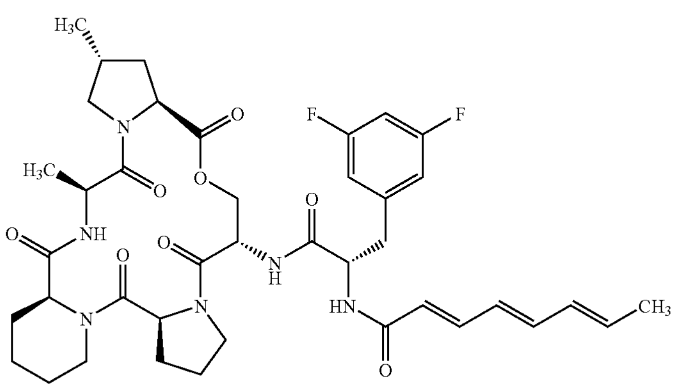 | A | 4.84 | MH+ | 781 |
| 12 | 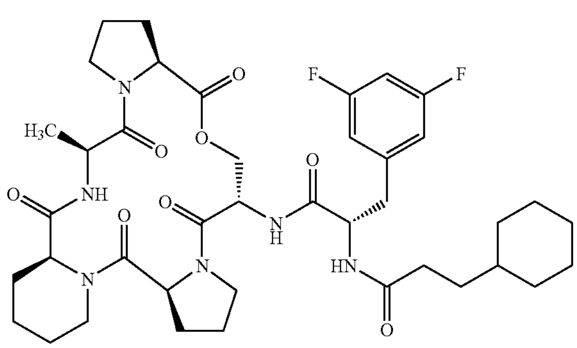 | MHZ2P | 4.86 | M+ | 784 |

| Ex. No. | Structure | HPLC/LCMS method | Retention time | Mass peak | Mass found |
|---|---|---|---|---|---|
| 13 | 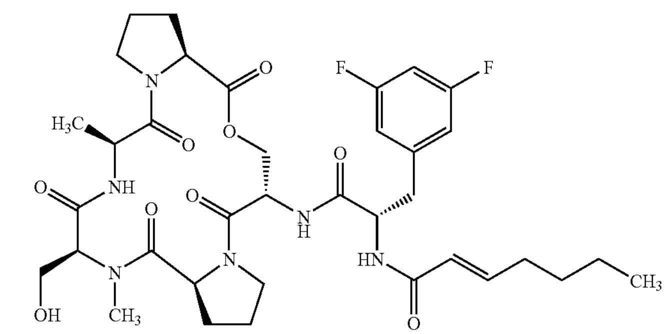 | MHZ2P | 4.08 | M+ | 746 |
| 14 | 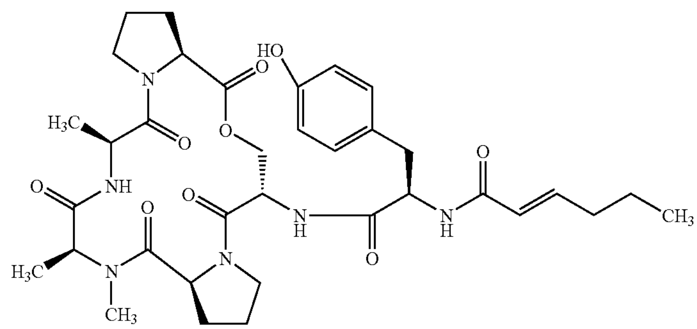 | MHZ2P | 3.50 | MH+ | 697 |
| 15 | 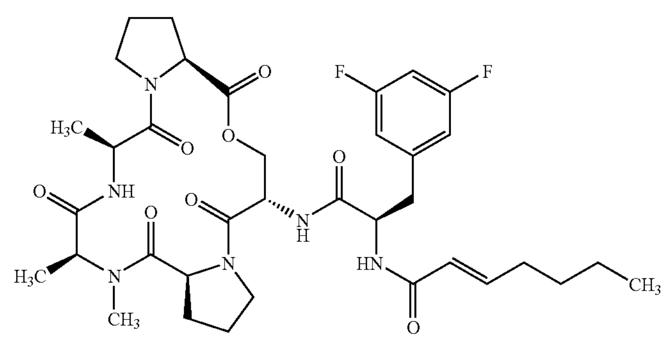 | B | 6.35 | MH+ | 731 |
| 16 | 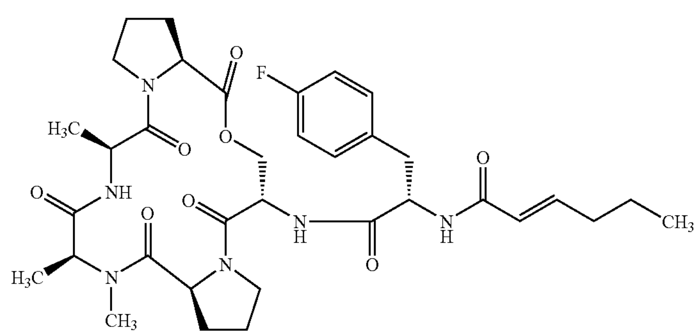 | MHZ2P | 4.04 | M+ | 698 |

-continued
| Ex. No. | Structure | HPLC/LCMS method | Retention time | Mass peak | Mass found |
|---|---|---|---|---|---|
| 17 | 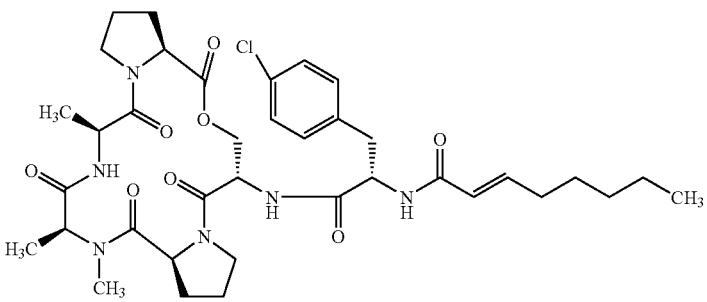 | MHZ2P | 4.66 | M+ | 742 |
| 18 | 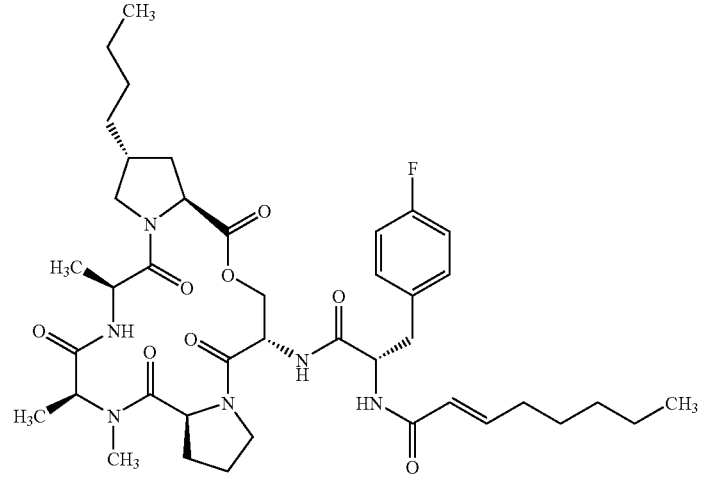 | MHZ2P | 5.1 | M+ | 782 |
| 19 | 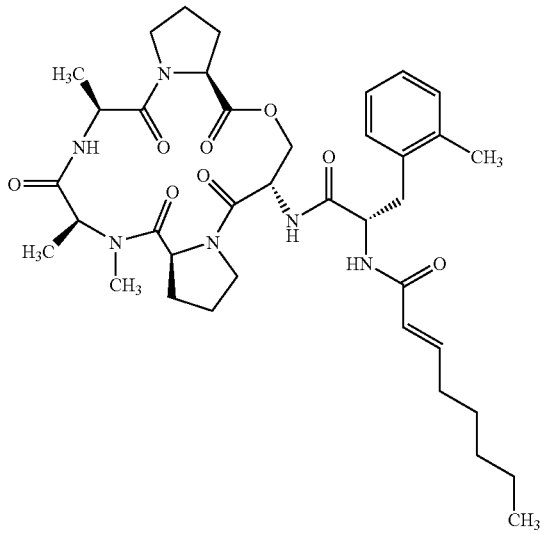 | A | 4.85 | M+ | 722 |

-continued
| Ex. No. | Structure | HPLC/LCMS method | Retention time | Mass peak | Mass found |
|---|---|---|---|---|---|
| 20 | 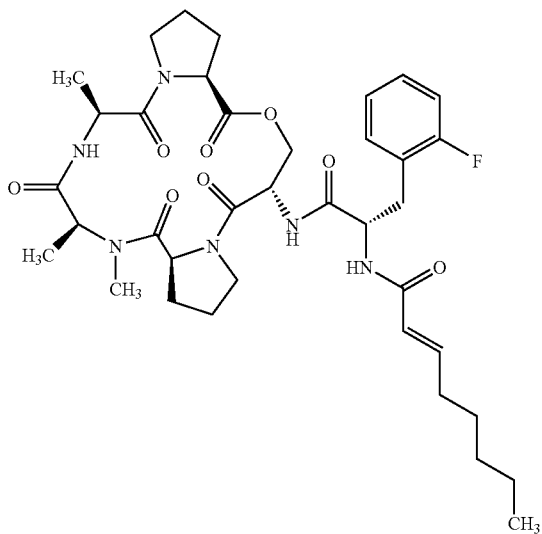 | A | 4.79 | M+ | 726 |
| 21 | 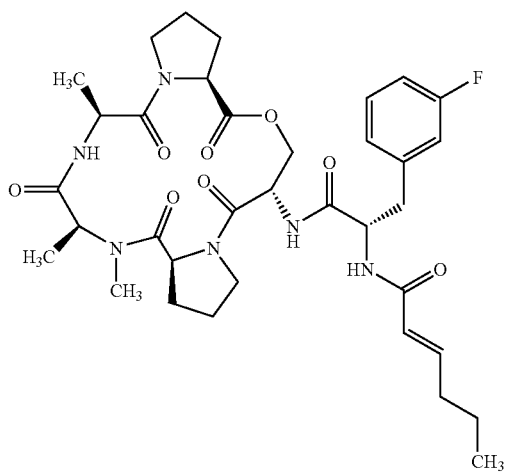 | C | 2.79 | M+ | 698 |

-continued

| Ex. No. | Structure | HPLC/LCMS method | Retention time | Mass peak | Mass found |
|---|---|---|---|---|---|
| 22 | 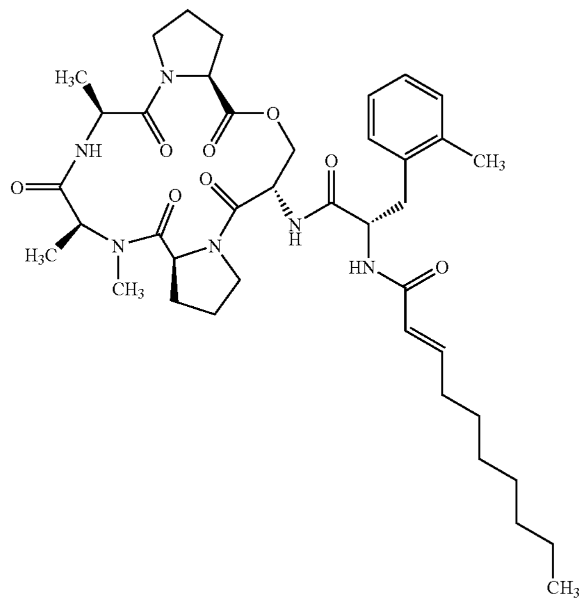 | MHZ2Q | 5.07 | M+ | 750 |
| 23 | 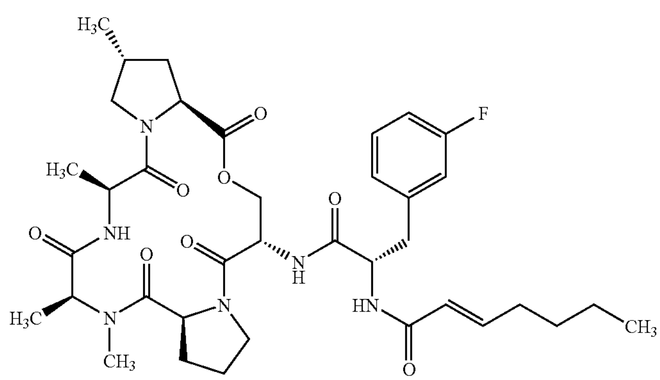 | MHZ2P | 4.38 | MH+ | 727 |
| 24 | 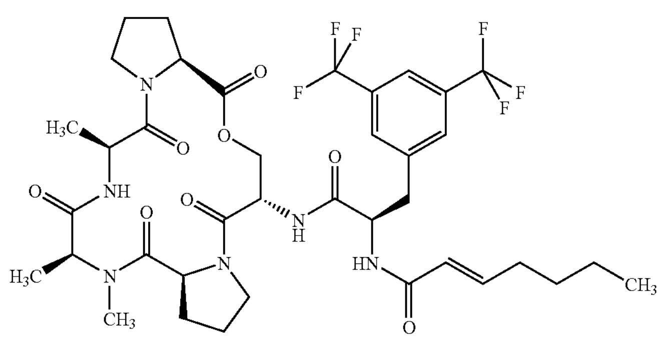 | A | 4.93 | MH+ | 831 |

| Ex. No. | Structure | HPLC/LCMS method | Retention time | Mass peak | Mass found |
|---|---|---|---|---|---|
| 25 | 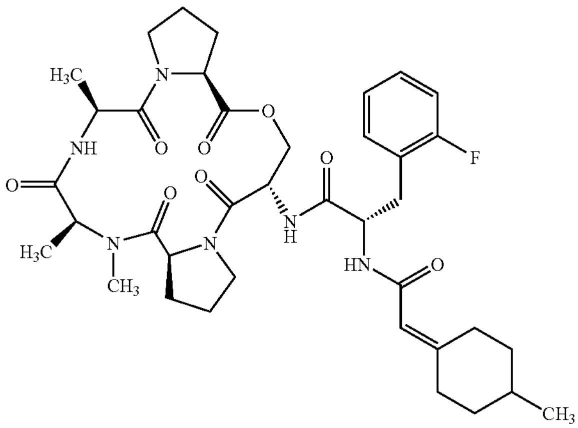 | MHZ2P | 4.35 | M+ | 739 |
| 26 | 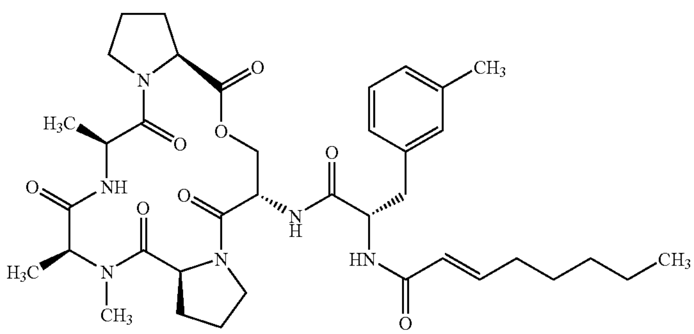 | A | 4.79 | M+Na+ | 745 |
| 27 | 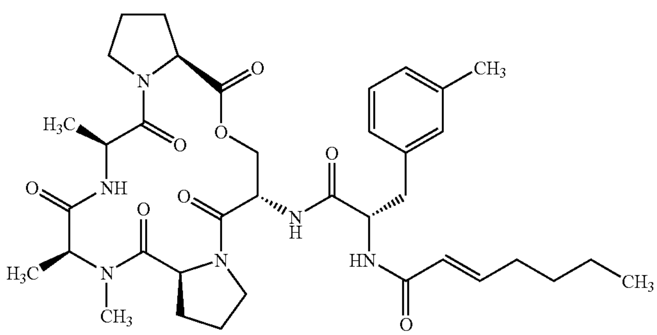 | MHZ2P | 4.34 | MH+ | 709 |
| 28 | 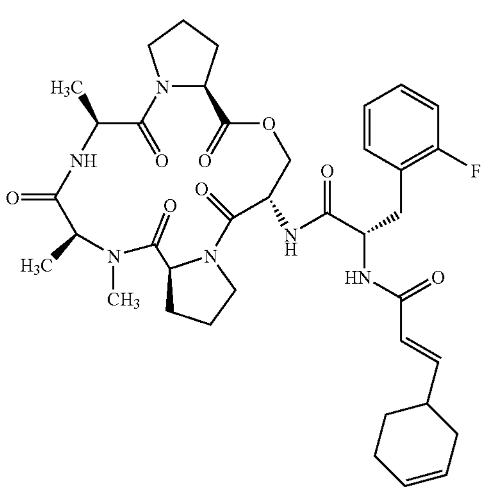 | MHZ2P | 4.22 | MH+ | 737 |

| Ex. No. | Structure | HPLC/LCMS method | Retention time | Mass peak | Mass found |
|---|---|---|---|---|---|
| 29 | 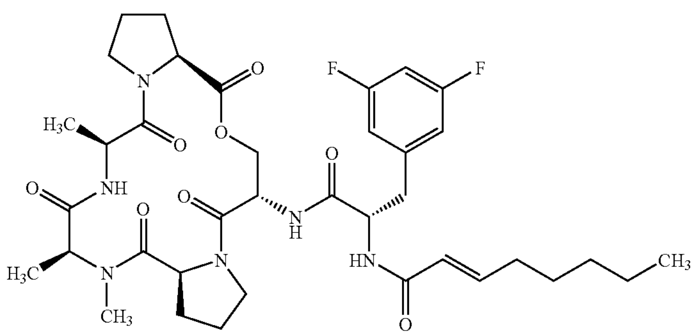 | B | 6.68 | MH+ | 744 |
| 30 | 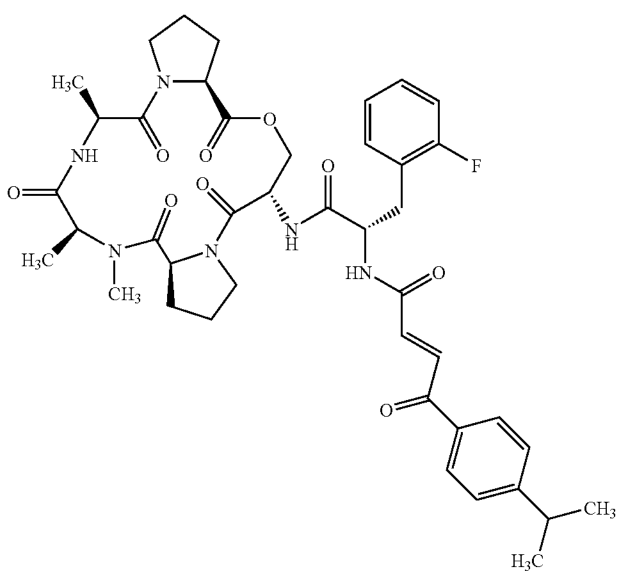 | MHZ2p | 4.52 | M+ | 802 |
| 31 | 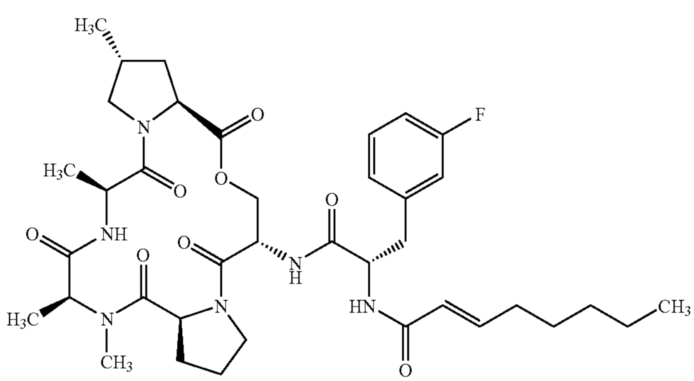 | MHZ2P | 4.59 | MH+ | 741 |

-continued

| Ex. No. | Structure | HPLC/LCMS method | Retention time | Mass peak | Mass found |
|---|---|---|---|---|---|
| 32 | 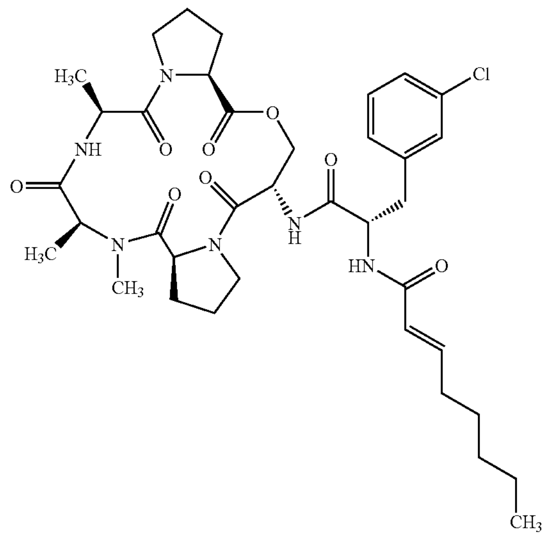 | A | 6.42 | MH+ | 743 |
| 33 | 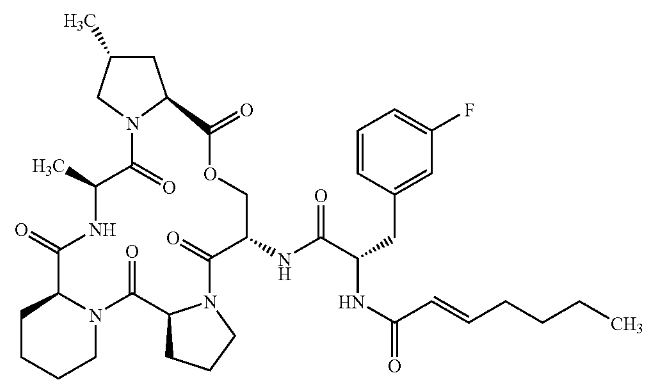 | MHZ2P | 4.60 | MH+ | 753 |
| 34 | 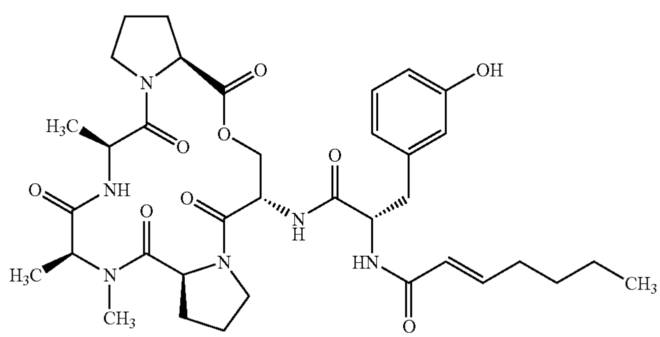 | B | 5.63 | MH+ | 711 |
| 35 | 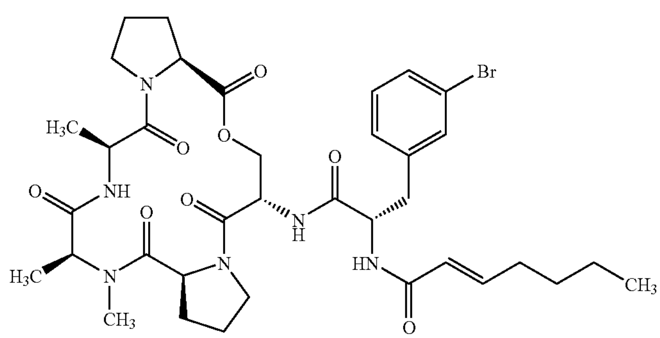 | B | 6.17 | MH+ | 773 |

-continued
| Ex. No. | Structure | HPLC/LCMS method | Retention time | Mass peak | Mass found |
|---|---|---|---|---|---|
| 36 | 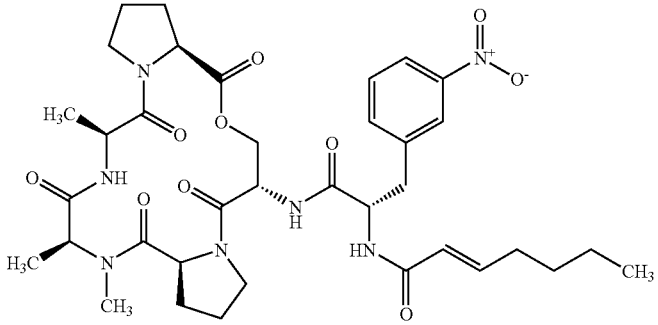 | B | 5.87 | MH+ | 740 |
| 37 | 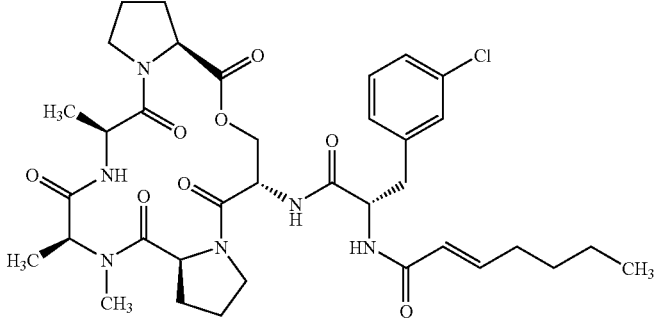 | B | 6.07 | MH+ | 729 |
| 38 | 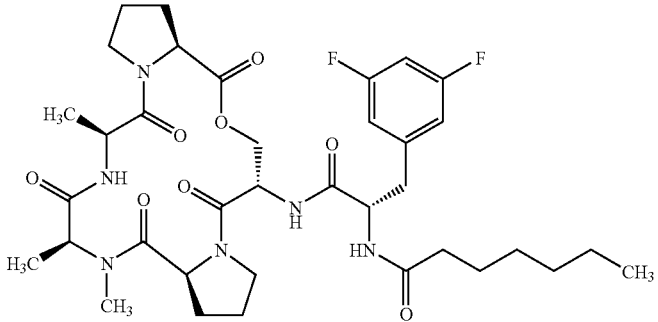 | MHZ2Q | 4.35 | M+ | 732 |
| 39 | 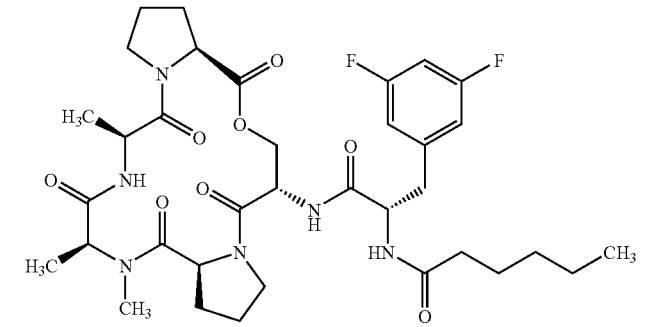 | MHZ2P | 4.11 | M+ | 719 |

-continued

| Ex. No. | Structure | HPLC/LCMS method | Retention time | Mass peak | Mass found |
|---|---|---|---|---|---|
| 40 | 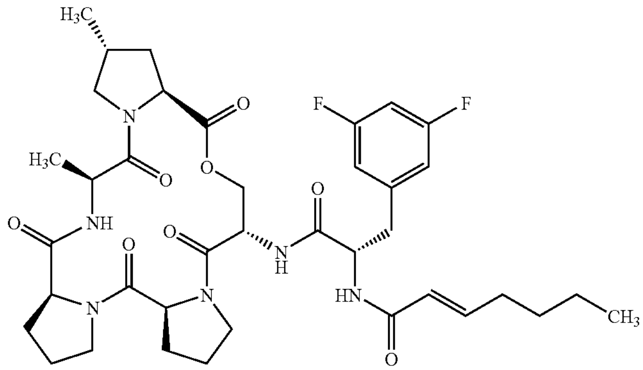 | B | 6.17 | MH+ | 757 |
| 41 | 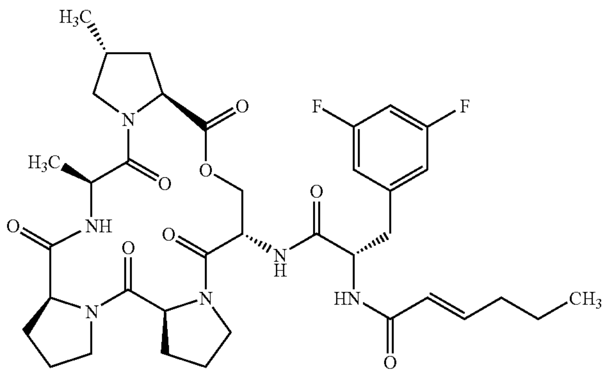 | B | 5.74 | MH+ | 743 |
| 42 | 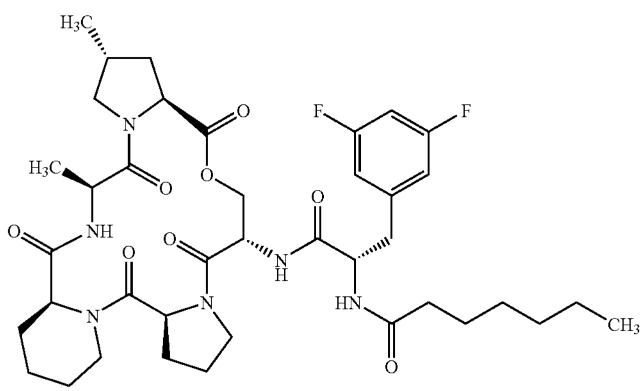 | MHZ2P | 4.70 | M+ | 773 |
| 43 | 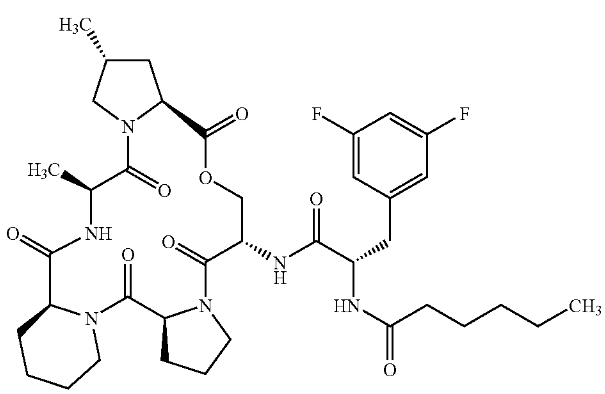 | MHZ2P | 4.5 | M+ | 759 |

-continued

| Ex. No. | Structure | HPLC/LCMS method | Retention time | Mass peak | Mass found |
|---|---|---|---|---|---|
| 44 | 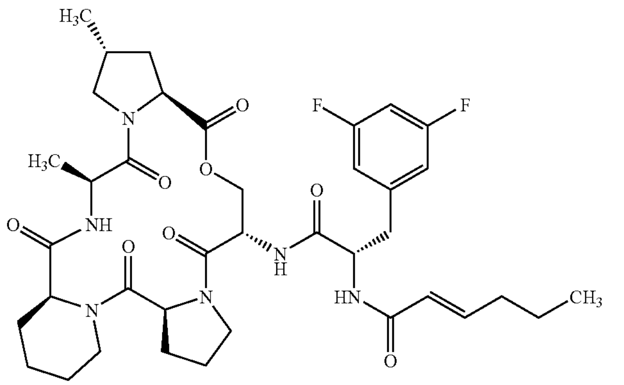 | B | 5.68 | MH+ | 757 |
| 45 | 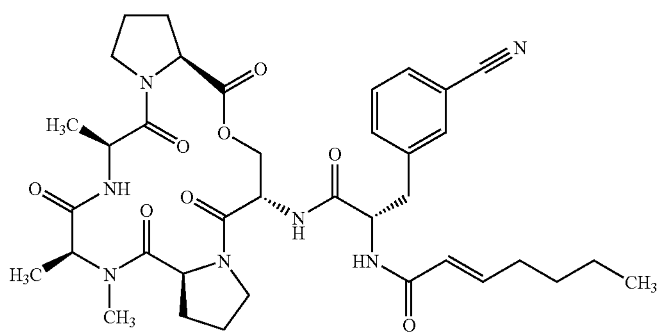 | B | 5.12 | MH+ | 720 |
| 46 | 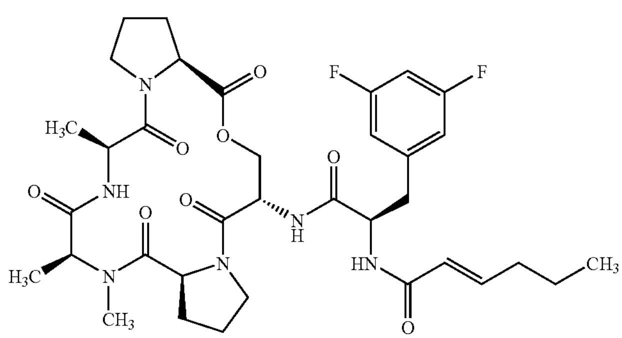 | B | 5.03 | MH+ | 717 |
| 47 | 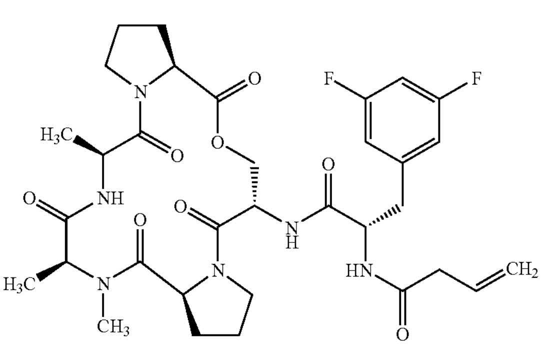 | MHZ2P | 3.7 | M+ | 688 |

-continued

| Ex. No. | Structure | HPLC/LCMS method | Retention time | Mass peak | Mass found |
|---|---|---|---|---|---|
| 48 | 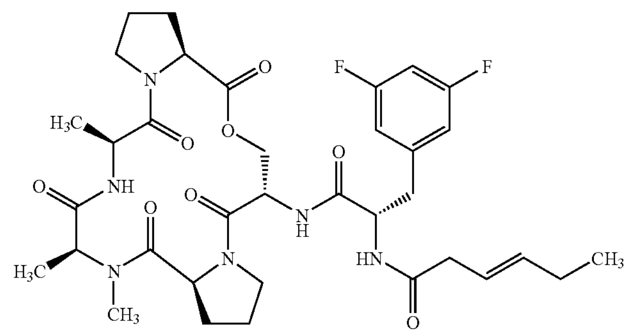 | MHZ2P | 4.0 | M+ | 716 |
| 49 | 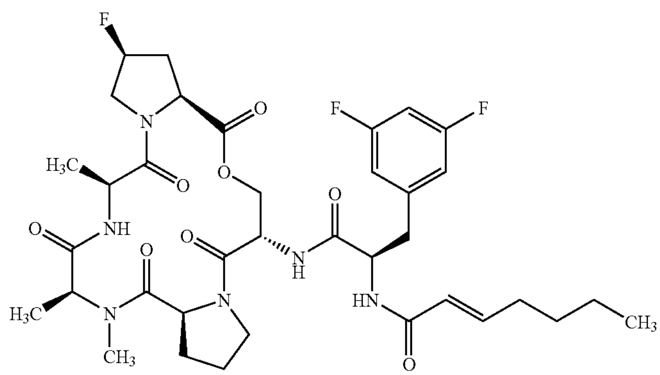 | MHZ2Q | 4.07 | MH+ | 749 |
| 50 | 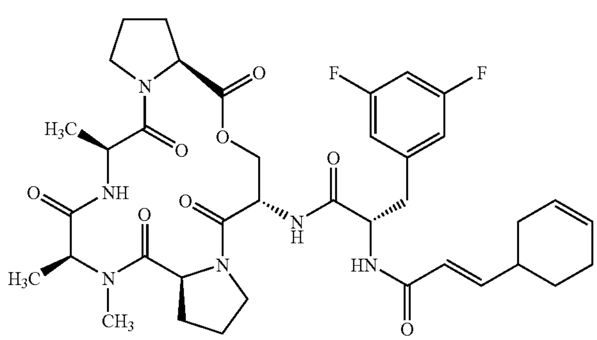 | A | 4.66 | MH+ | 755 |
| 51 | 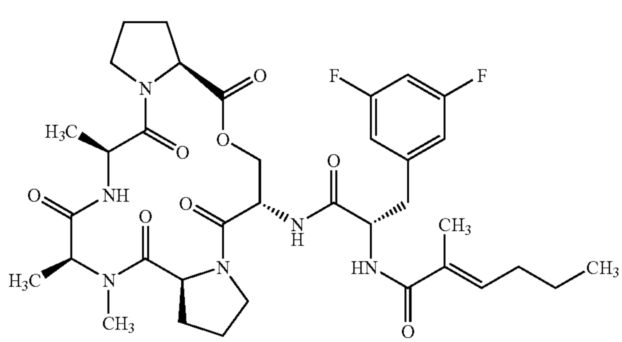 | A | 4.57 | MH+ | 731 |

-continued

| Ex. No. | Structure | HPLC/LCMS method | Retention time | Mass peak | Mass found |
|---|---|---|---|---|---|
| 52 | 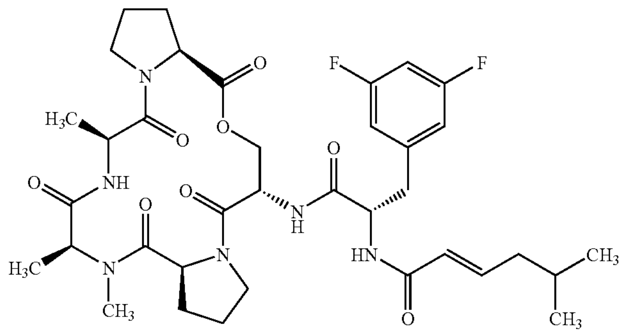 | A | 4.61 | MH+ | 731 |
| 53 | 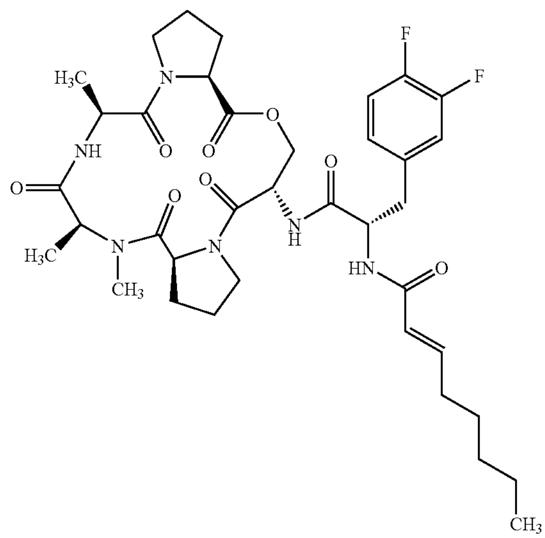 | C | 2.79 | MH+ | 745 |
| 54 | 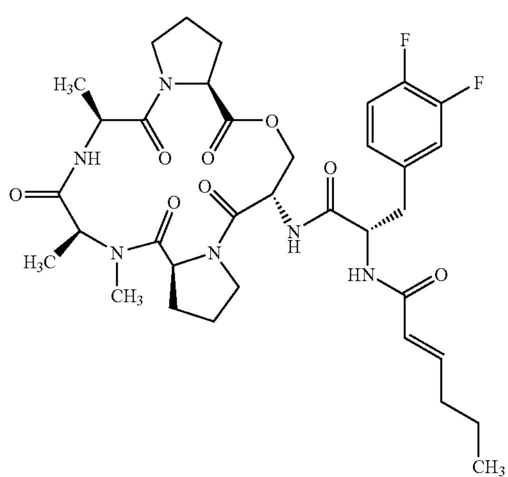 | C | 2.57 | MH+ | 717 |

-continued
| Ex. No. | Structure | HPLC/LCMS method | Retention time | Mass peak | Mass found |
|---|---|---|---|---|---|
| 55 | 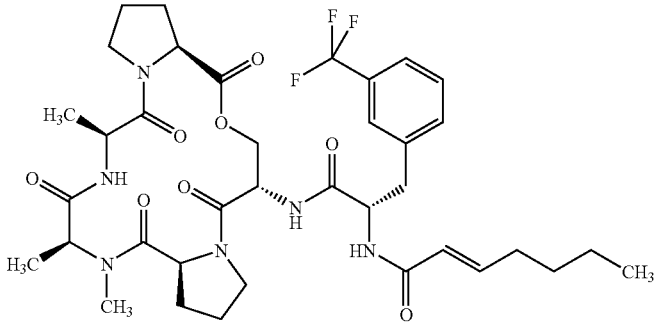 | A | 4.64 | MH+ | 763 |
| 56 | 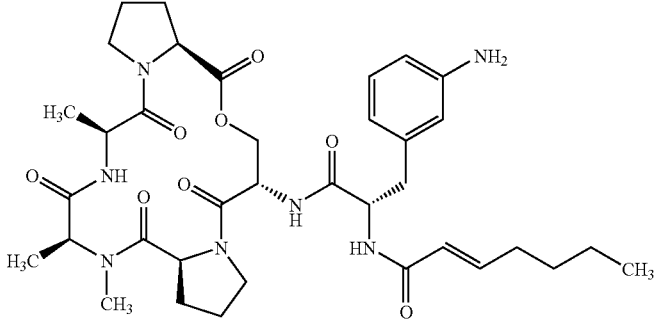 | A | 4.14 | MH+ | 710 |
| 57 | 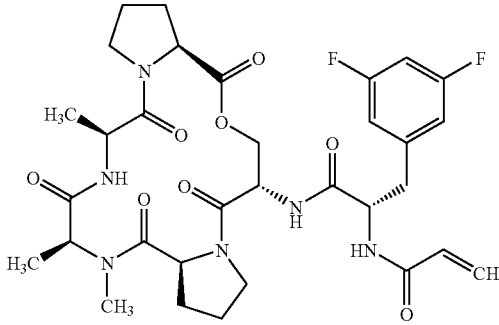 | A | 4.07 | MH+ | 675 |
| 58 | 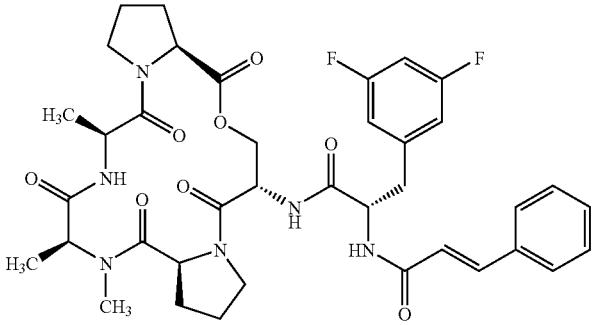 | A | 4.56 | MH+ | 751 |

-continued

| Ex. No. | Structure | HPLC/LCMS method | Retention time | Mass peak | Mass found |
|---|---|---|---|---|---|
| 59 | 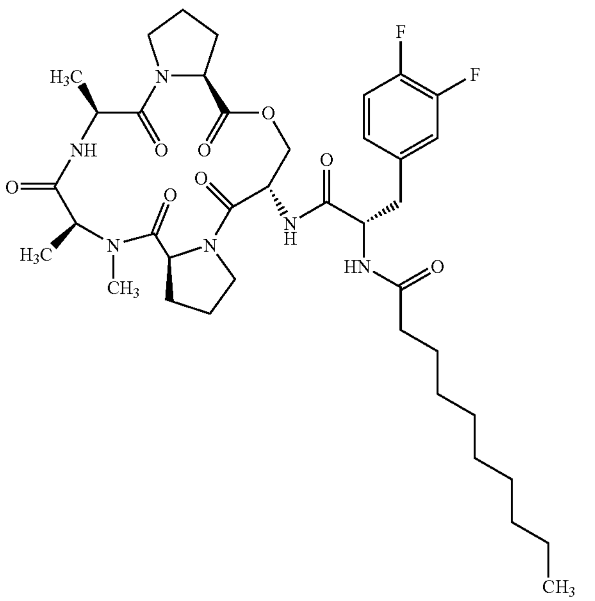 | C | 3.08 | MH+ | 775 |
| 60 | 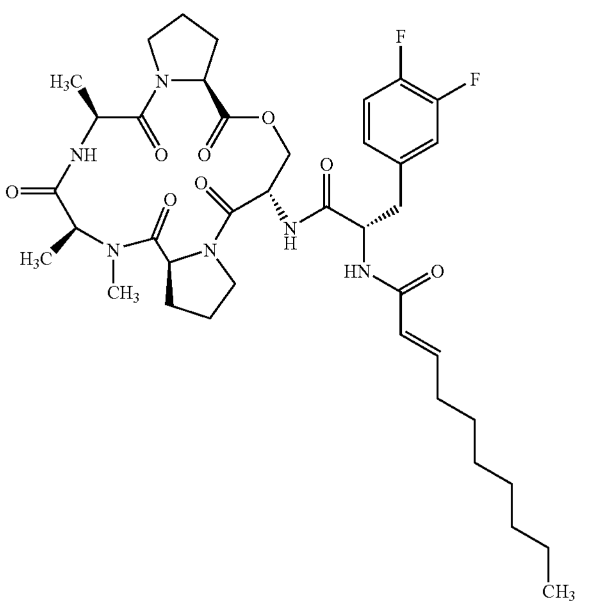 | C | 3.06 | MH+ | 773 |
| 61 | 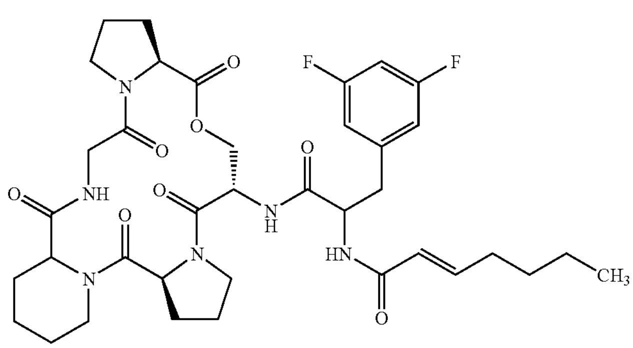 | MHZ2P | 4.05 | M+ | 742 |

-continued

| Ex. No. | Structure | HPLC/LCMS method | Retention time | Mass peak | Mass found |
|---|---|---|---|---|---|
| 62 | 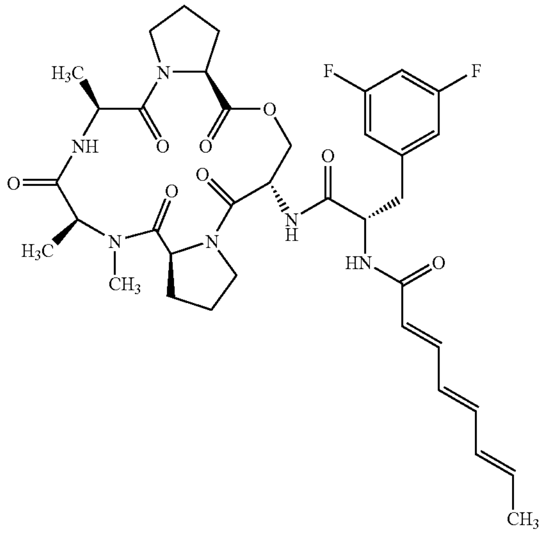 | C | 2.68 | MH+ | 741 |
| 63 | 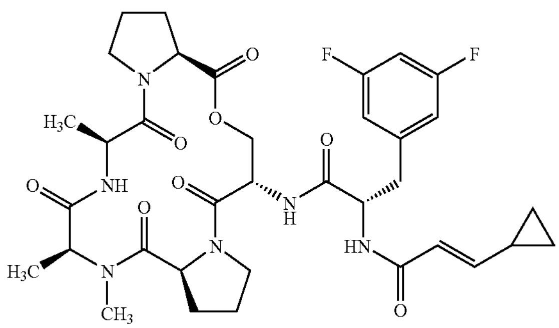 | A | 4.32 | MH+ | 714 |
| 64 | 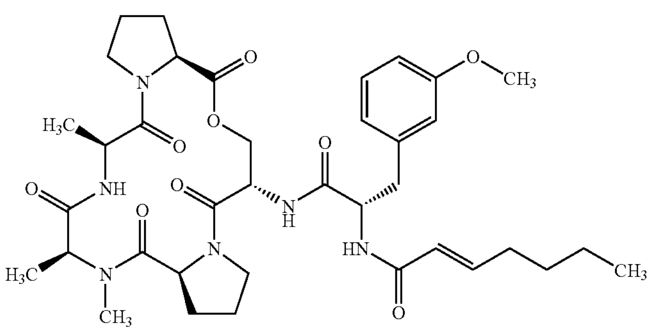 | A | 4.54 | MH+ | 725 |
| 65 | 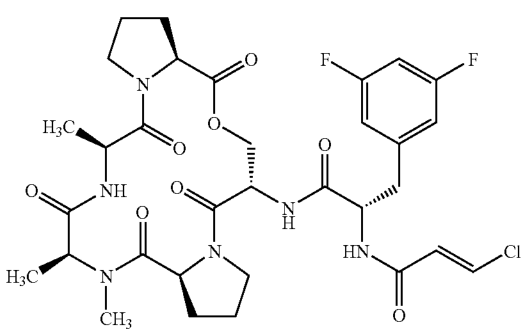 | MHZ2P | 3.90 | M+ | 708 |

-continued

| Ex. No. | Structure | HPLC/LCMS method | Retention time | Mass peak | Mass found |
|---|---|---|---|---|---|
| 66 | 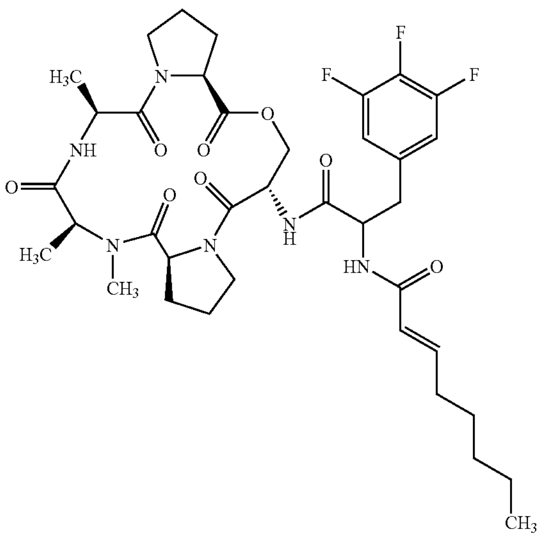 | C | 2.89 | MH+ | 763 |
| 67 | 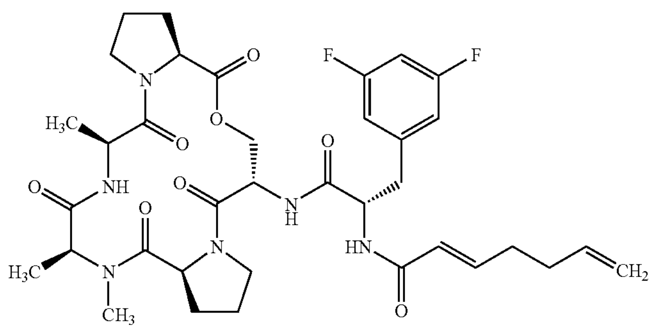 | MHZ2P | 4.1 | M+ | 728 |
| 68 | 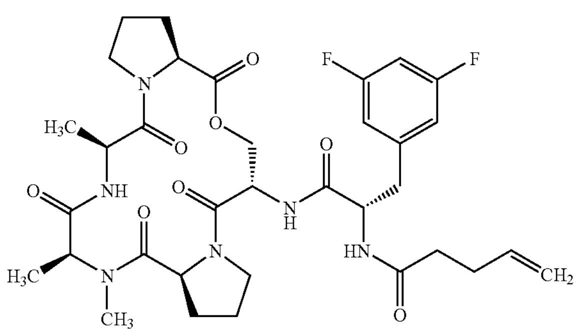 | MHZ2P | 3.8 | M+ | 702 |
| 69 | 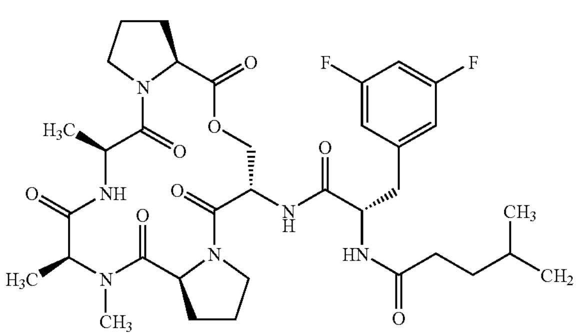 | MHZ2P | 4.1 | M+ | 718 |

| Ex. No. | Structure | HPLC/LCMS method | Retention time | Mass peak | Mass found |
|---|---|---|---|---|---|
| 70 | 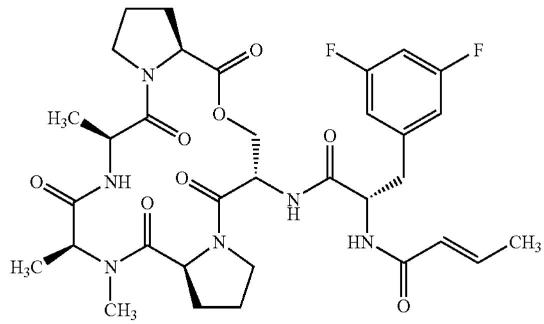 | MHZ2P | 3.7 | M+ | 688 |
| 71 | 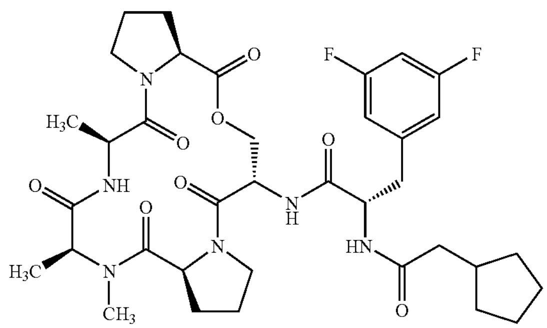 | MHZ2P | 4.1 | M+ | 730 |
| 72 | 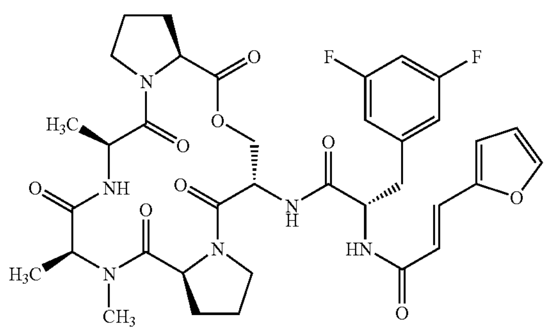 | MHZ2P | 4.0 | M+ | 740 |
| 73 | 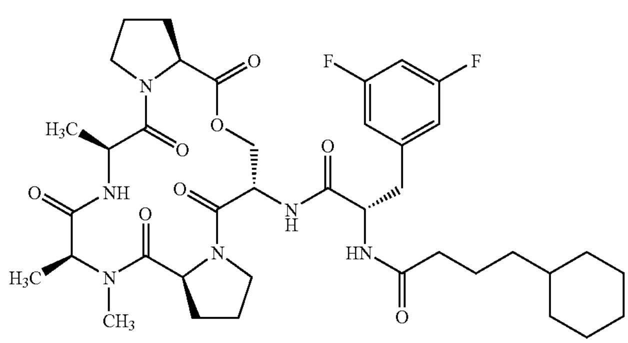 | MHZ2P | 4.77 | M+ | 773 |

-continued
| Ex. No. | Structure | HPLC/LCMS method | Retention time | Mass peak | Mass found |
|---|---|---|---|---|---|
| 74 | 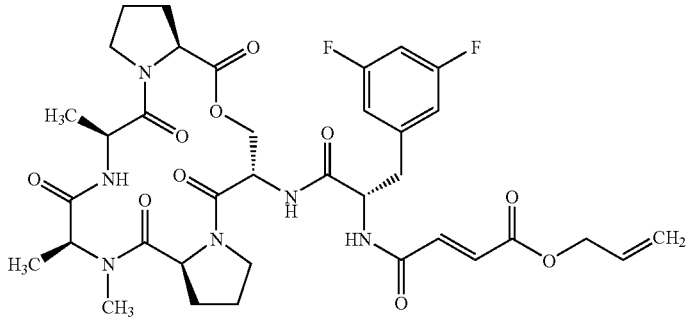 | MHZ2P | 4.0 | M+ | 758 |
| 75 | 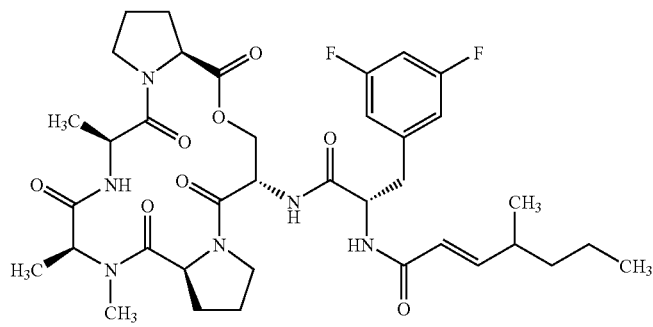 | MHZ2Q | 4.52 | MH+ | 745 |
| 76 | 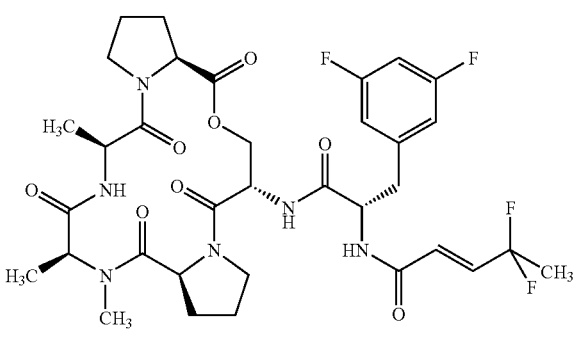 | MHZ2P | 4.1 | MH+ | 739 |
| 77 | 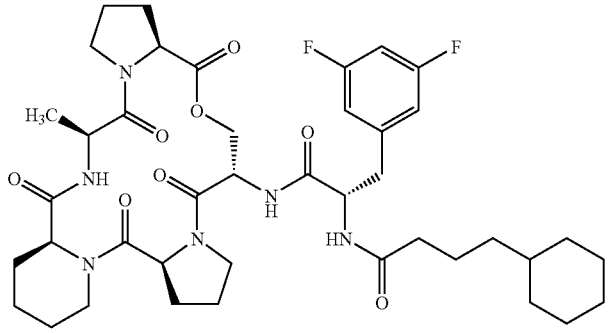 | MHZ2P | 5.1 | M+ | 798 |

-continued

| Ex. No. | Structure | HPLC/LCMS method | Retention time | Mass peak | Mass found |
|---|---|---|---|---|---|
| 78 | 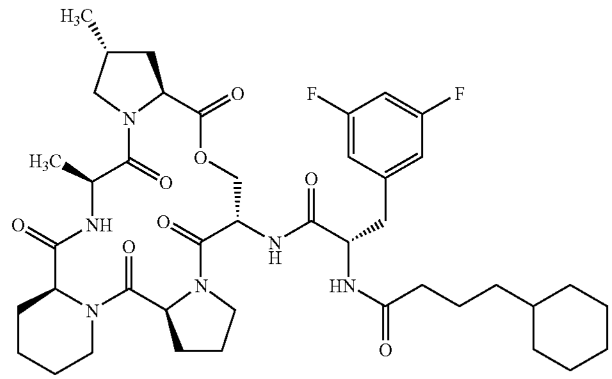 | MHZ2P | 5.2 | M+ | 812 |
| 79 | 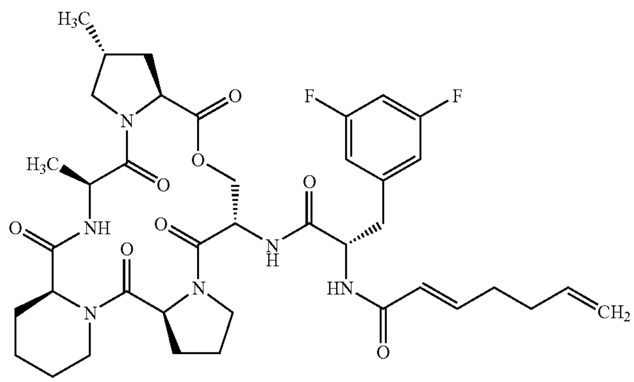 | MHZ2P | 4.6 | M+ | 768 |
| 80 | 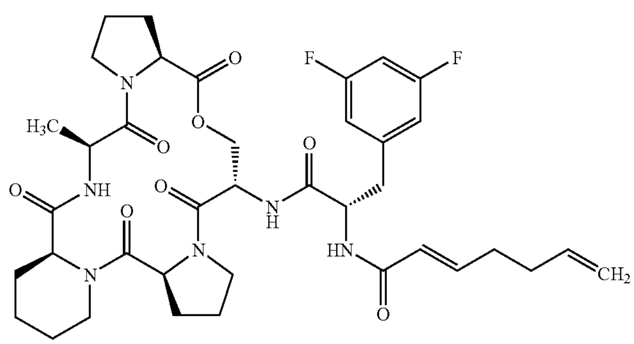 | MHZ2P | 4.35 | M+ | 754 |
| 81 | 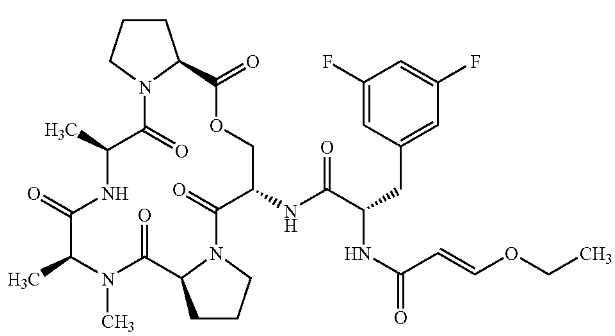 | A | 4.28 | MH+ | 719 |

-continued

| Ex. No. | Structure | HPLC/LCMS method | Retention time | Mass peak | Mass found |
|---|---|---|---|---|---|
| 82 | 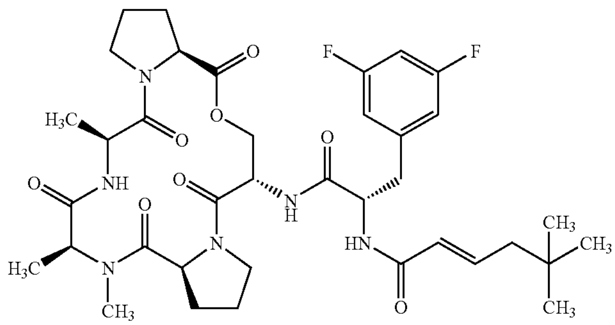 | A | 4.74 | MH+ | 745 |
| 83 | 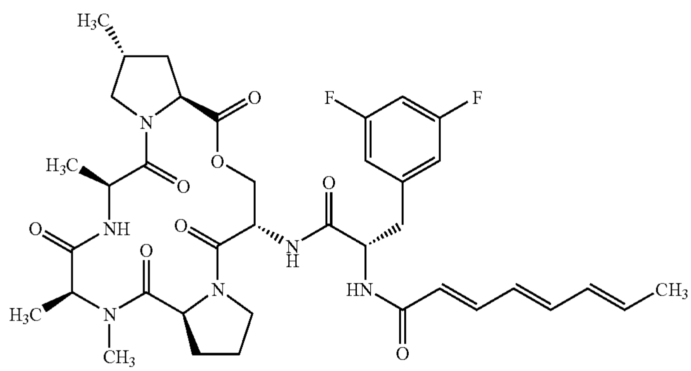 | A | 4.77 | MH+ | 755 |
| 84 | 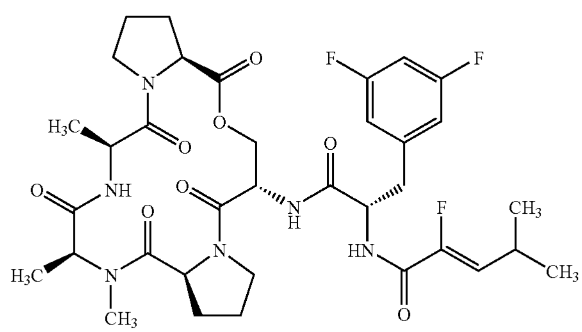 | A | 4.57 | MH+ | 735 |
| 85 | 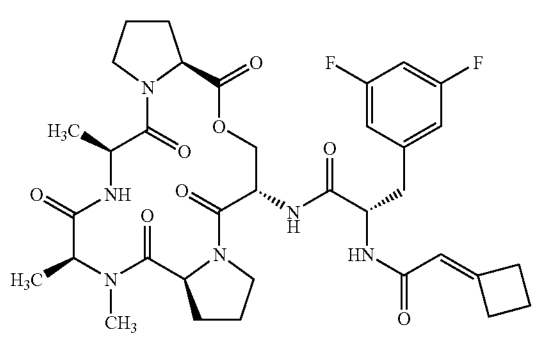 | MHZ2Q | 3.92 | MH+ | 715 |

-continued

| Ex. No. | Structure | HPLC/LCMS method | Retention time | Mass peak | Mass found |
|---|---|---|---|---|---|
| 86 | 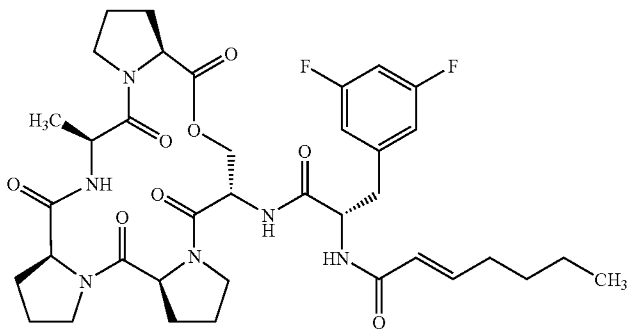 | MHZ2P | 3.95 | M+ | 742 |
| 87 | 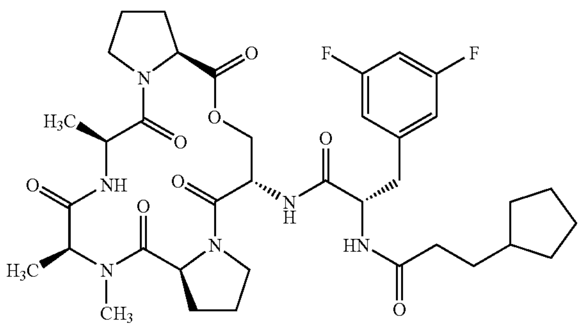 | A | 4.68 | MH+ | 745 |
| 88 | 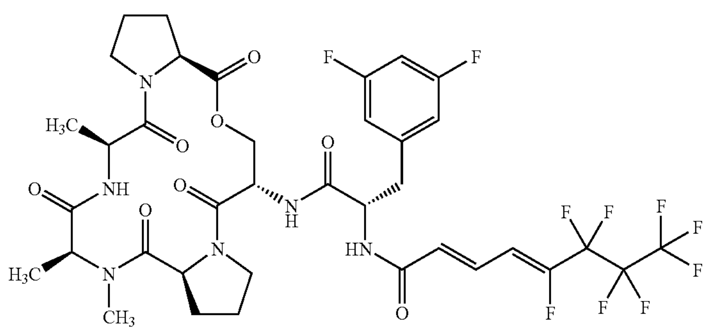 | A | 4.89 | MH+ | 887 |

| Example | Structure | MW | HPLC or LCMS Rt [min] | MS ESI [M + H]+ | HPL or LCMS method |
|---|---|---|---|---|---|
| 89 | 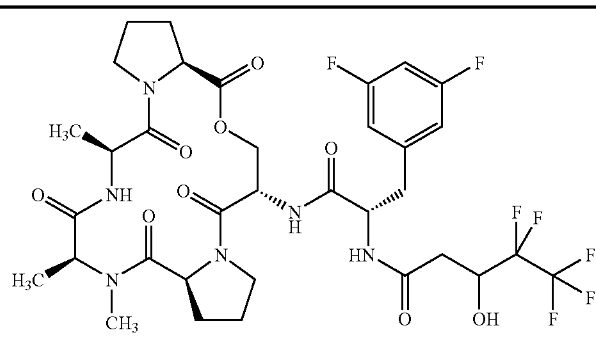 | | 3.95 | MH+ | 811 |

(Example 89 row: HPLC/LCMS method = A)

-continued

| Example | Structure | MW | HPLC or LCMS Rt [min] | MS ESI [M + H]+ | HPL or LCMS method |
|---|---|---|---|---|---|
| 90 | 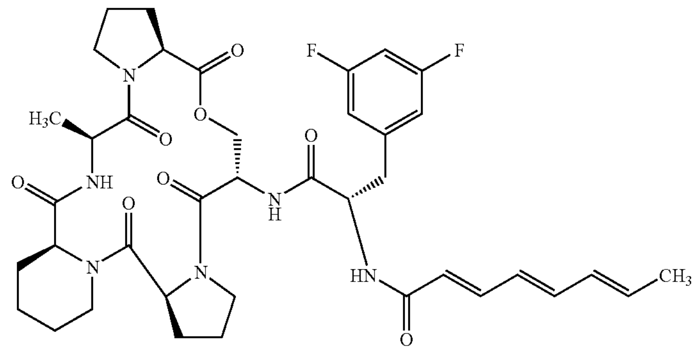 | 766.84 | 4.50 | 767 | MHZ2Q |
| 91 | Chiral | 784.90 | 4.90 | 784 | MHZ2Q |
| 92 | 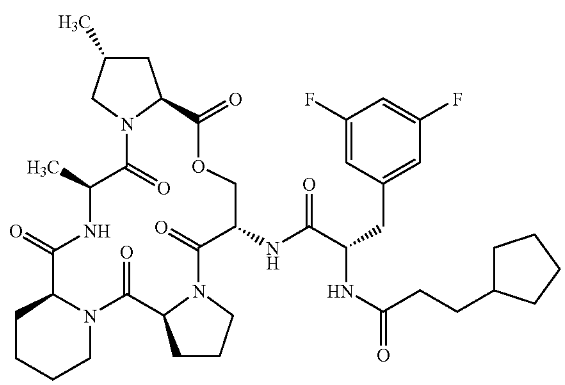 | 784.90 | 4.70 | 785 | MHZ2Q |
| 93 | Chiral | 792.88 | 4.50 | 792 | MHZ2Q |

-continued

| Example | Structure | MW | HPLC or LCMS Rt [min] | MS ESI [M + H]+ | HPL or LCMS method |
|---|---|---|---|---|---|
| 94 | Chiral | 744.79 | 3.70 | 744 | MHZ2Q |
| 95 | Chiral | 829.89 | 3.00 | 829 | MHZ2Q |
| 96 | 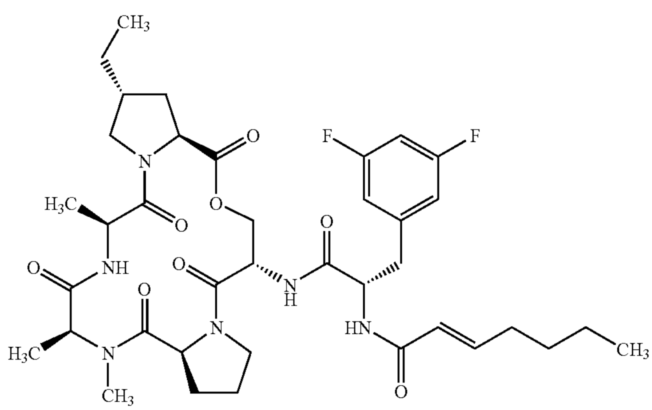 | 758.86 | 4.94 | 759 | A |
| 97 | 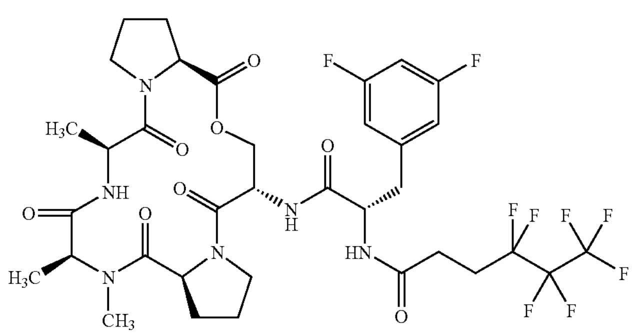 | 844.72 | 4.84 | 845 | A |

-continued

| Example | Structure | MW | HPLC or LCMS Rt [min] | MS ESI [M + H]⁺ | HPL or LCMS method |
|---|---|---|---|---|---|
| 98 | Chiral | 784.90 | 4.90 | 785 | MHZ2Q |
| 99 | 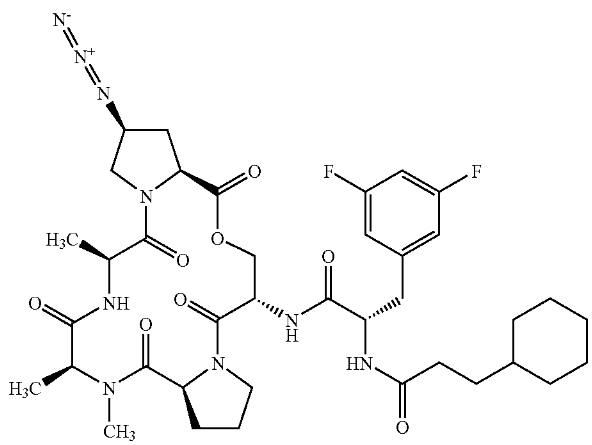 | 799.88 | 4.60 | 800 | MHZ2Q |
| 100 | ClH | 810.33 | 2.05 | 774 (—HCl) | C |

-continued

| Example | Structure | | MW | HPLC or LCMS Rt [min] | MS ESI [M + H]+ | HPL or LCMS method |
|---|---|---|---|---|---|---|
| 101 | 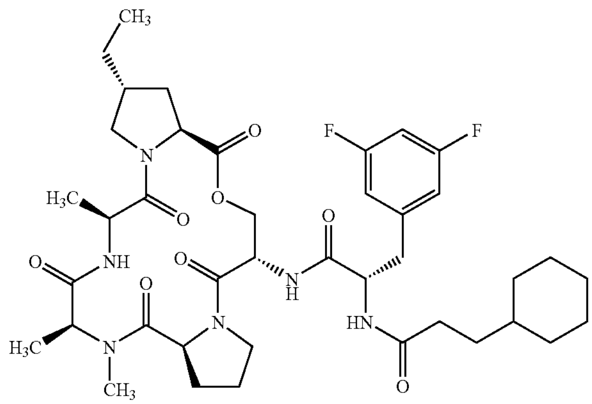 | | 786.91 | 4.90 | 787 | MHZ2Q |
| 102 | 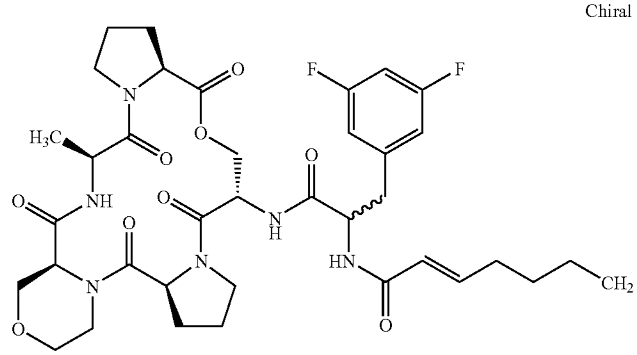 | Chiral | 758.82 | 4.1 and 4.2 | 758 | MHZ2Q |
| 103 | 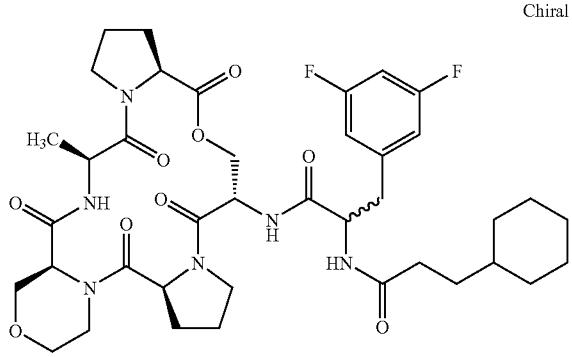 | Chiral | 786.87 | 4.3 and 4.4 | 786 | MHZ2Q |
| 104 | 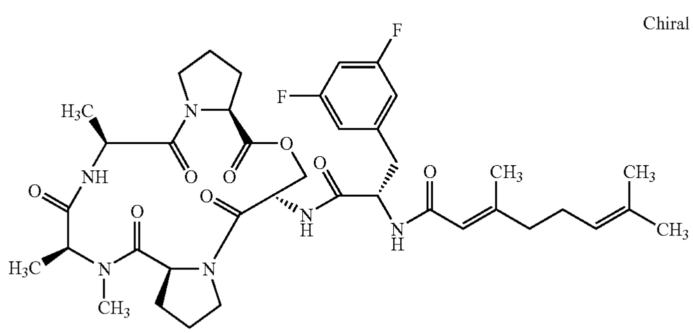 | Chiral | 770.87 | 2.95 | 770 | C |

-continued

| Example | Structure | MW | HPLC or LCMS Rt [min] | MS ESI [M + H]+ | HPL or LCMS method |
|---|---|---|---|---|---|
| 105 | 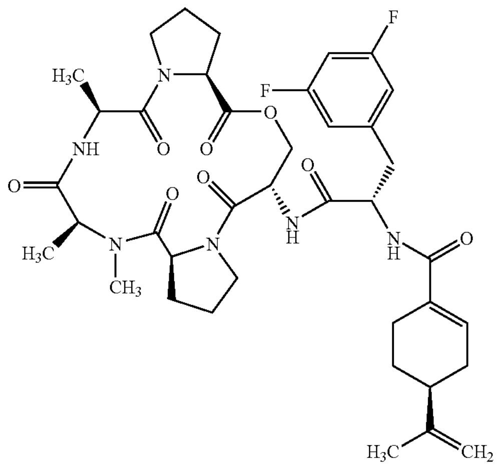 | 768.87 | 2.81 | 768 | C |
| 106 | Chiral | 774.90 | 3.05 | 774 | C |
| 107 | 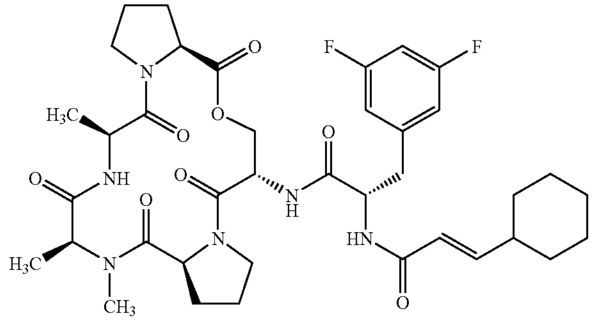 | 758.84 | 4.84 | 757 | A |
| 108 | Chiral | 886.00 | 5.03 | 885 | MHZ2P |

-continued
| Example | Structure | MW | HPLC or LCMS Rt [min] | MS ESI [M + H]+ | HPL or LCMS method |
|---|---|---|---|---|---|
| 109 | 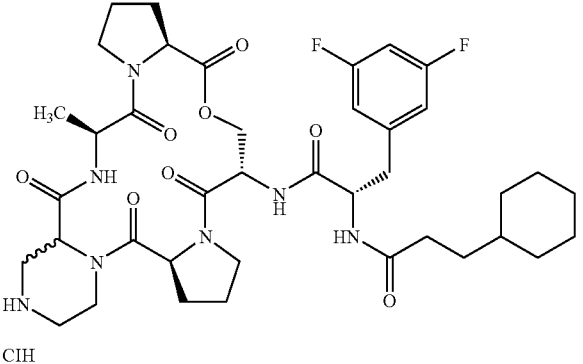 Chiral ClH | 822.35 | 3.19 | 785 | MHZ2P |
| 110 | 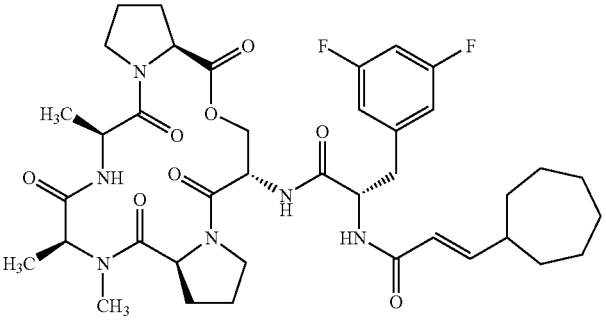 | 770.87 | 5.12 | 771 | A |
| 111 | 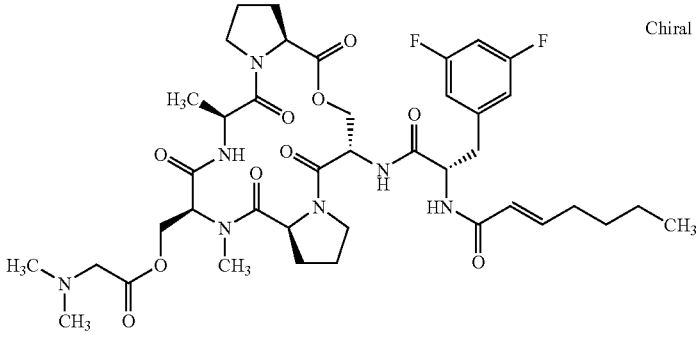 Chiral | 831.91 | 2.01 | 831 | C |
| 112 | 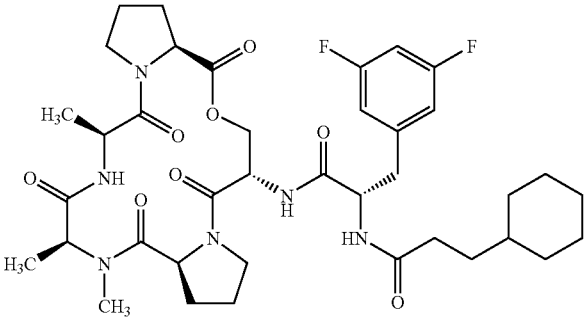 | 758.86 | 4.99 | 759 | A |

-continued

| Example | Structure | MW | HPLC or LCMS Rt [min] | MS ESI [M + H]⁺ | HPL or LCMS method |
|---|---|---|---|---|---|
| 113 | 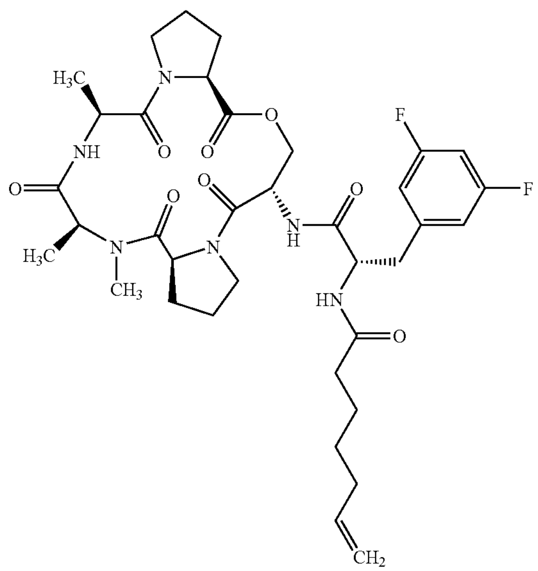 | 730.81 | 2.64 | 730 | C |
| 114 | 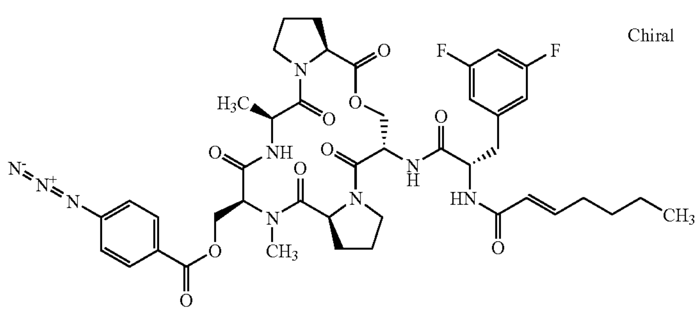 | 891.92 | 5.00 | 891 | MHZ2Q |
| 115 | 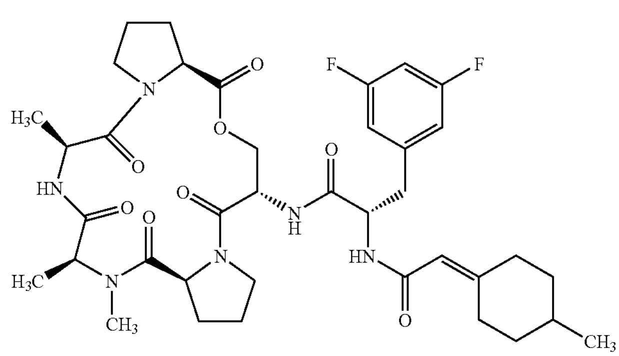 | 756.84 | 4.91 | 757 | A |

-continued
| Example | Structure | MW | HPLC or LCMS Rt [min] | MS ESI [M + H]+ | HPL or LCMS method |
|---|---|---|---|---|---|
| 116 | 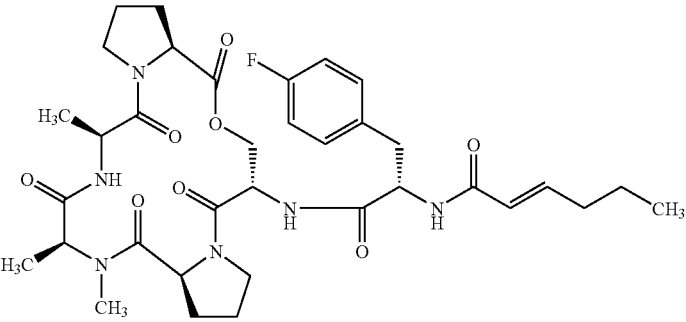 | 871.03 | 5.21 | 871 | MHZ2P |
| 117 | 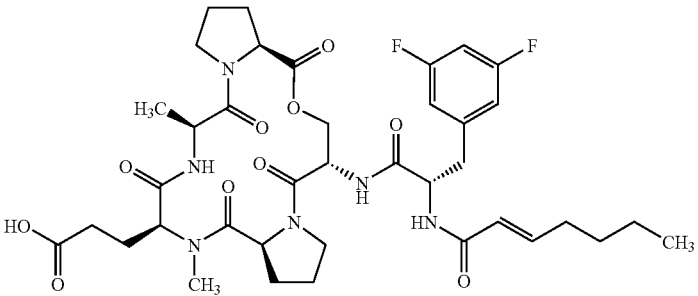 | 788.84 | 4.45 | 789 | A |
| 118 | 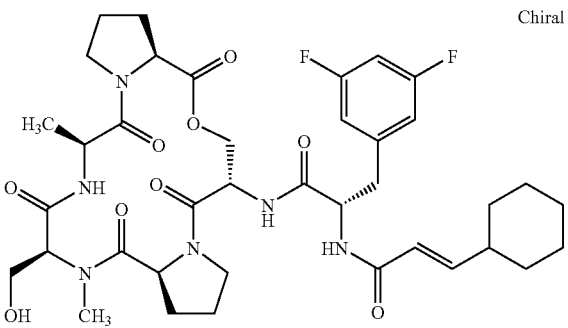 Chiral | 772.84 | 4.21 | 772 | MHZ2Q |
| 119 | 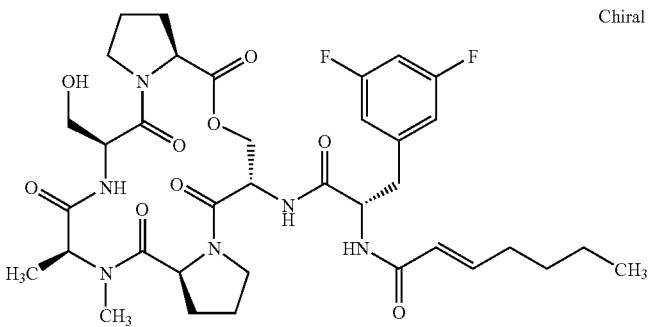 Chiral | 746.82 | 3.87 | 746 | MHZ2Q |

-continued

| Example | Structure | | MW | HPLC or LCMS Rt [min] | MS ESI [M + H]+ | HPL or LCMS method |
|---|---|---|---|---|---|---|
| 120 | 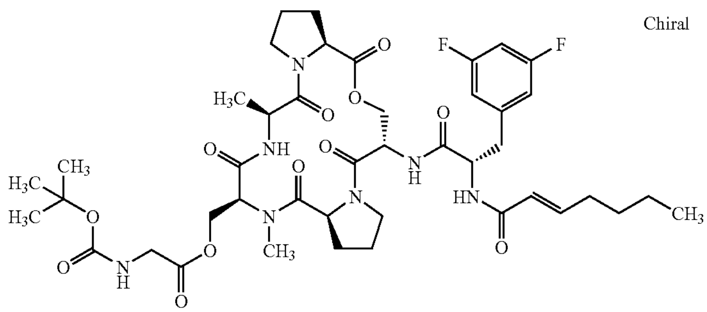 | Chiral | 903.97 | 4.69 | 903 | MHZ2P |
| 121 | 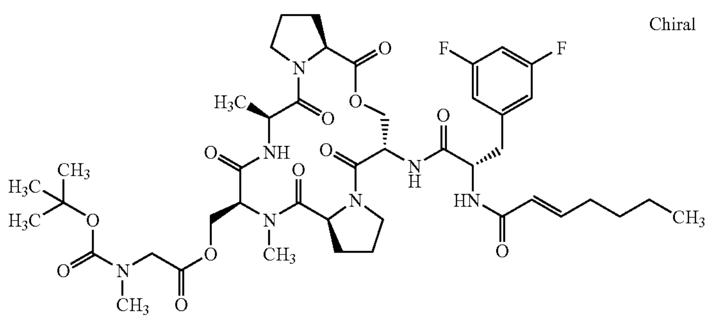 | Chiral | 918.00 | 4.83 | 917 | MHZ2Q |
| 122 | 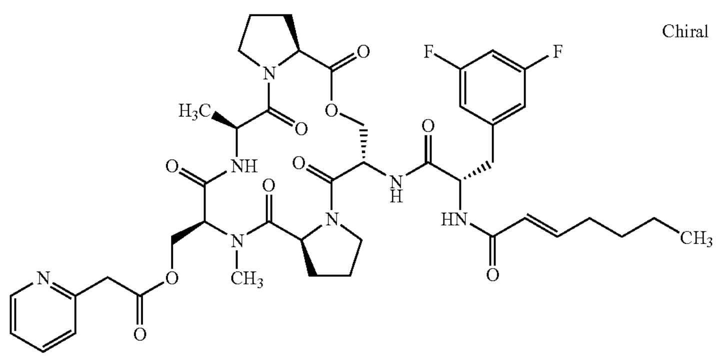 | Chiral | 865.93 | 4.22 | 865 | MHZ2P |
| 123 | 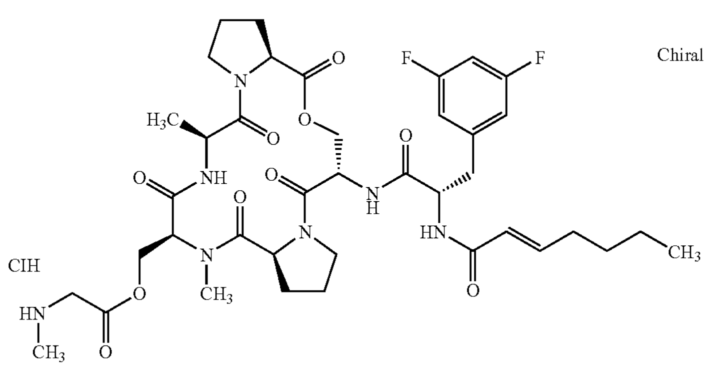 | Chiral | 854.34 | 3.19 | 817 | MHZ2P |

-continued

| Example | Structure | MW | HPLC or LCMS Rt [min] | MS ESI [M + H]+ | HPL or LCMS method |
|---|---|---|---|---|---|
| 124 | 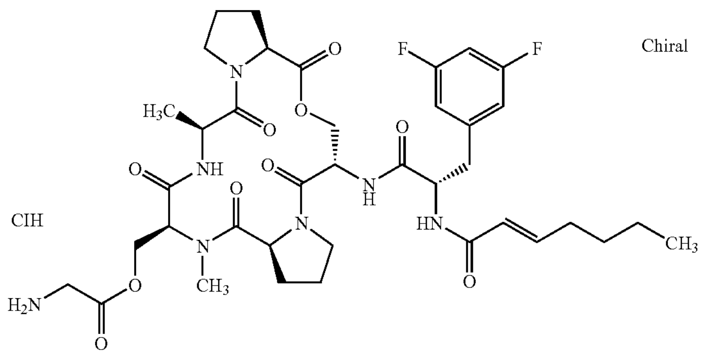 | 840.32 | 3.17 | 804 | MHZ2P |
| 125 | 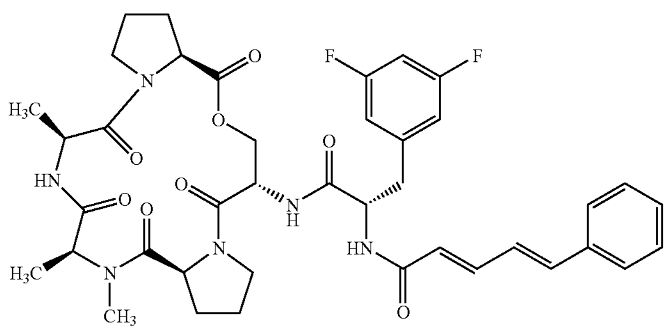 | 776.83 | 4.78 | 777 | A |
| 126 | 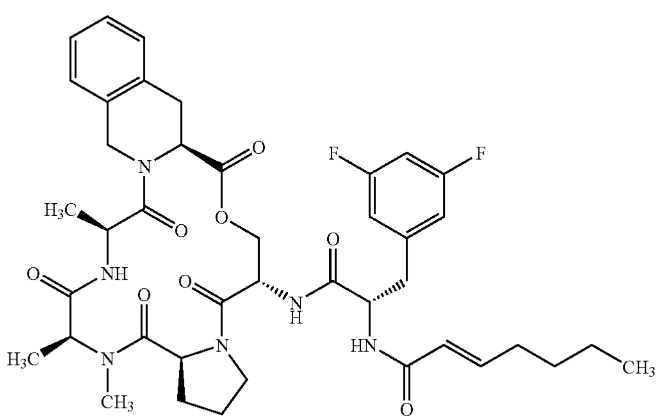 | 792.88 | 5.10 | 793 | A |

-continued

| Example | Structure | MW | HPLC or LCMS Rt [min] | MS ESI [M + H]⁺ | HPL or LCMS method |
|---|---|---|---|---|---|
| 127 | 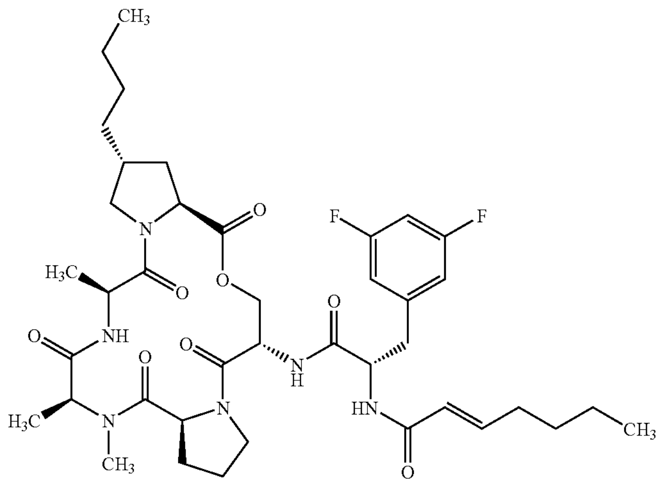 | 786.91 | 5.33 | 787 | A |
| 128 | 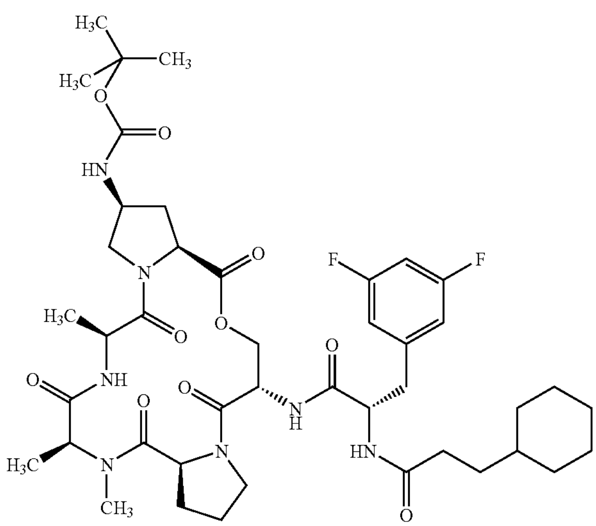 | 873.99 | 5.11 | 874 | A |
| 129 | 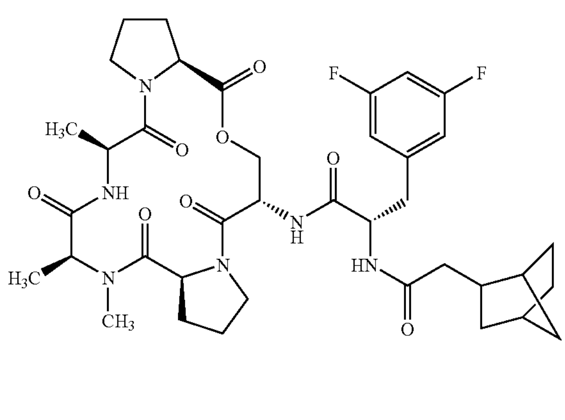 | 756.84 | 4.82 | 757 | A |

-continued

| Example | Structure | MW | HPLC or LCMS Rt [min] | MS ESI [M + H]+ | HPL or LCMS method |
|---|---|---|---|---|---|
| 130 | 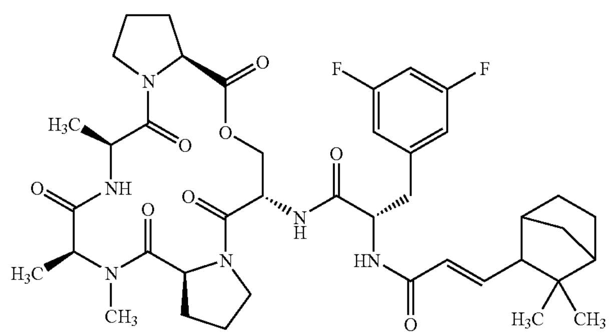 | 796.91 | 5.21 | 797 | A |
| 131 | 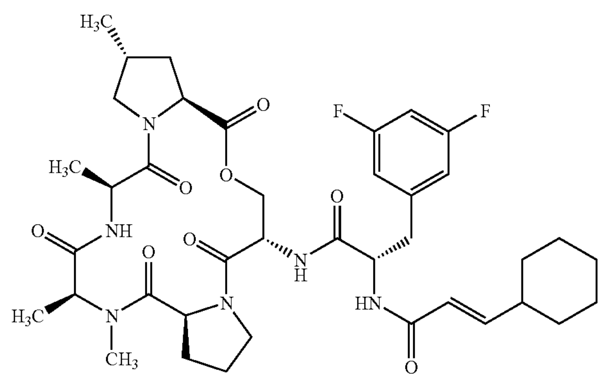 | 770.87 | 5.11 | 771 | A |
| 132 | 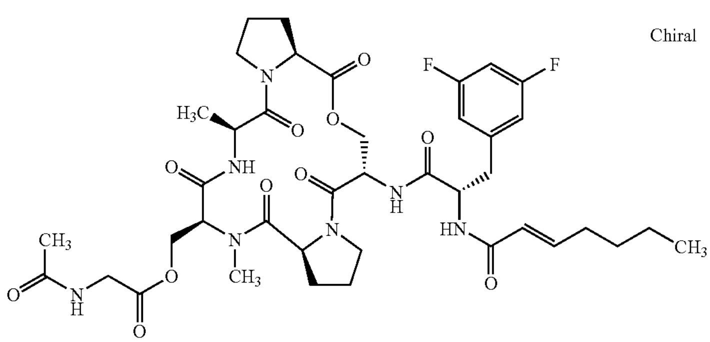 | 845.89 | | | |

| Example | Structure | MW | HPLC or LCMS Rt [min] | MS ESI [M + H]+ | HPL or LCMS method |
|---|---|---|---|---|---|
| 133 | Chiral | 708.85 | 4.21 | 708 | SMKL-ZQ-1 |
| 134 | Chiral | 734.89 | 4.47 | 734 | SMKL-ZQ-1 |
| 135 | 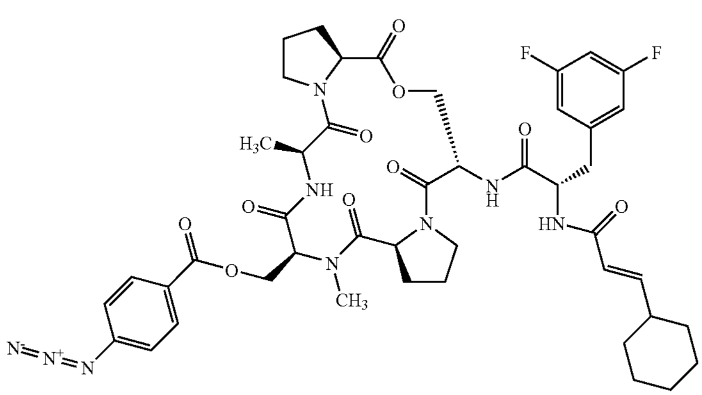 | 917.96 | 4.38 | 917 | SMKL-ZQ-1 |

-continued

| Example | Structure | MW | HPLC or LCMS Rt [min] | MS ESI [M + H]+ | HPL or LCMS method |
|---|---|---|---|---|---|
| 136 | 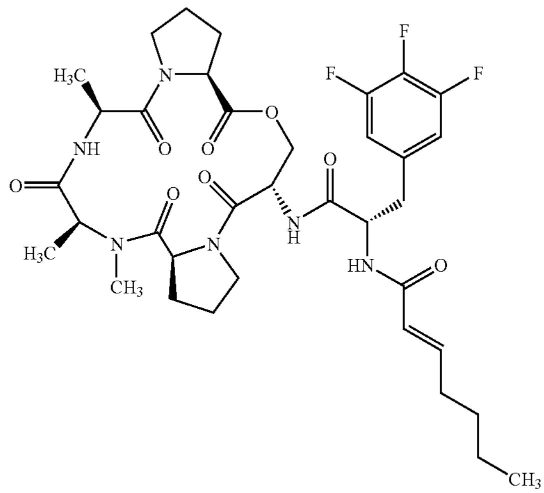 | 748.80 | 3.44 and 3.53 | 748 | SMKL-ZQ-1 |
| 137 | 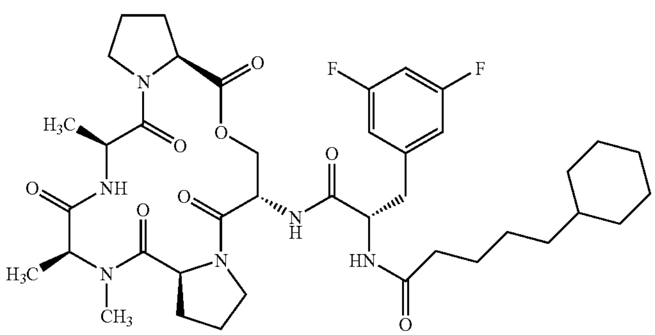 | 786.91 | 5.40 | 787 | A |
| 138 | 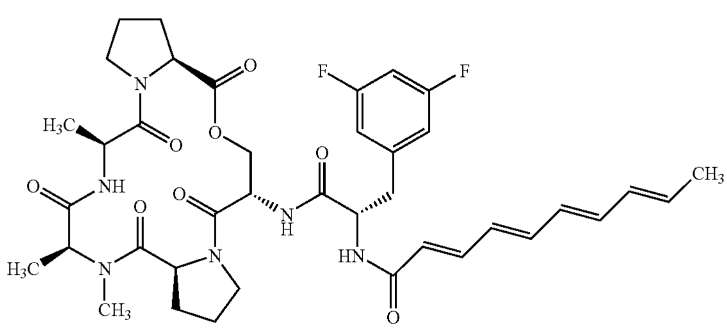 | 766.84 | 4.98 | 767 | A |

-continued
| Example | Structure | MW | HPLC or LCMS Rt [min] | MS ESI [M + H]+ | HPL or LCMS method |
|---|---|---|---|---|---|
| 139 | 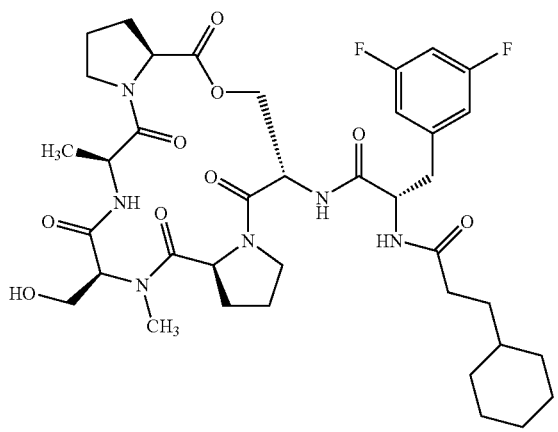 | 774.86 | 3.85 | 774 | SMKL-ZQ-1 |
| 140 | 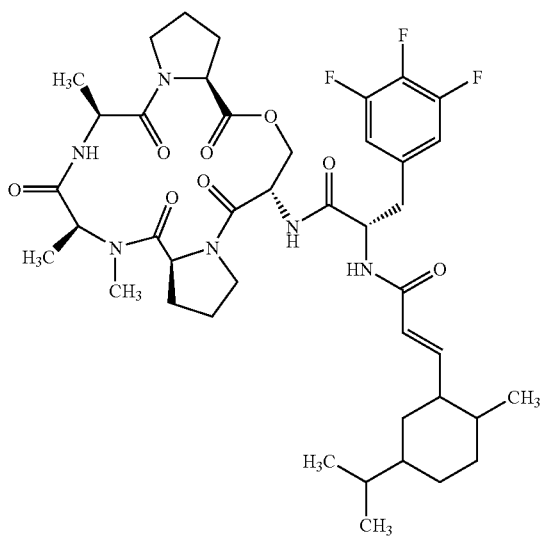 | 830.94 | 5.60 | 830 | MHZ2Q |

-continued

| Example | Structure | MW | HPLC or LCMS Rt [min] | MS ESI [M + H]+ | HPL or LCMS method |
|---|---|---|---|---|---|
| 141 | Chiral | 930.01 | 5.00 | 929 | MHZ2Q |
| 142 | Chiral | 866.35 | 3.56 | 829 | MHZ-2P |
| 143 | Chiral | 919.98 | 5.40 | 919 | MHZ-2P |

-continued

| Example | Structure | MW | HPLC or LCMS Rt [min] | MS ESI [M + H]+ | HPL or LCMS method |
|---|---|---|---|---|---|
| 144 | 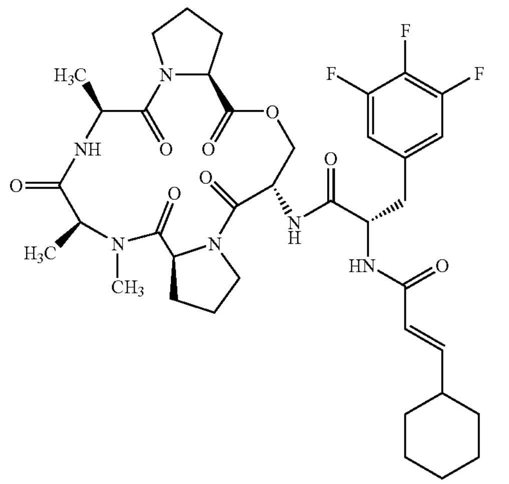 | 774.83 | 5.10 | 774 | A |
| 145 | 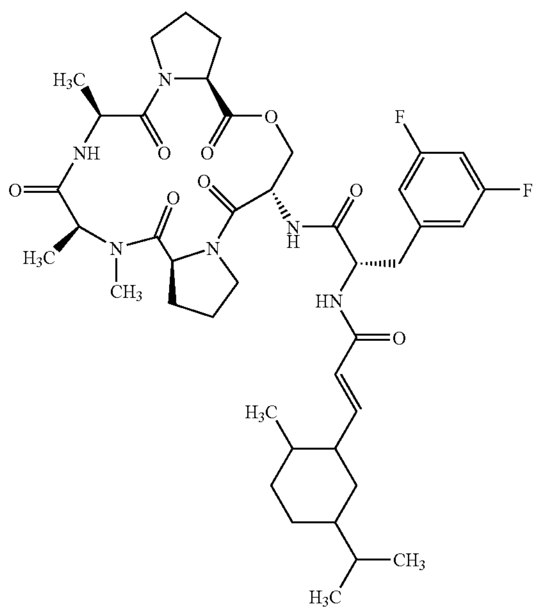 | 812.95 | 4.37 | 812 | SMKL-ZQ-1 |
| 146 | 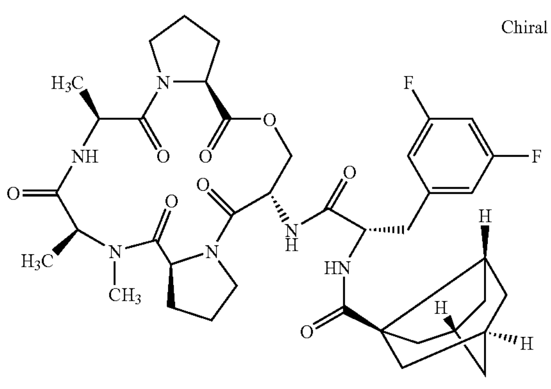 | 768.85 | 4.60 | 768 | MHZ-2Q-01 |

-continued
| Example | Structure | MW | HPLC or LCMS Rt [min] | MS ESI [M + H]+ | HPL or LCMS method |
|---|---|---|---|---|---|
| 147 | 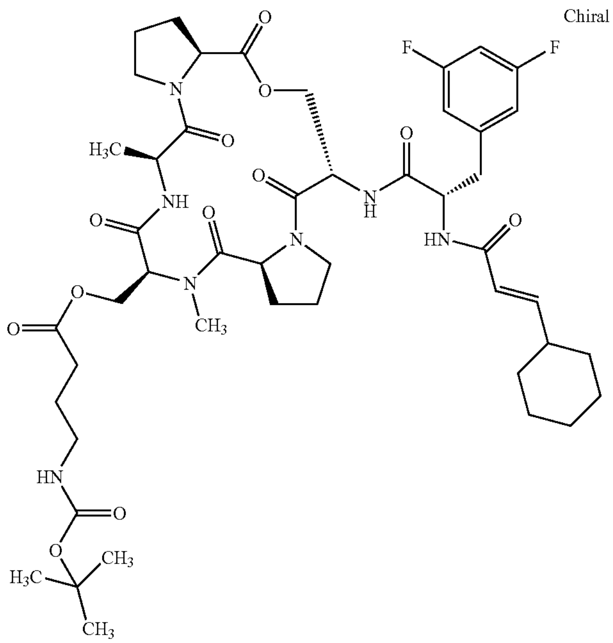 | 958.06 | 5.10 | 957 | MHZ-2Q-01 |
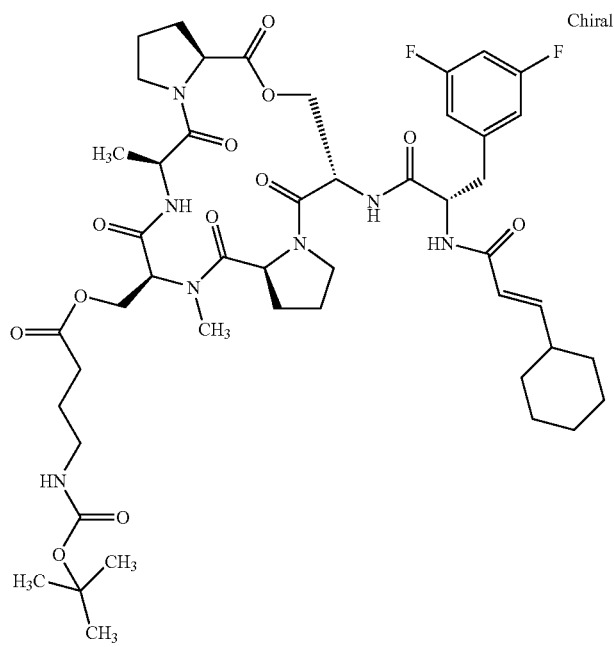
| 148 | | 770.87 | 5.00 | 770 | MHZ-2P-01 |
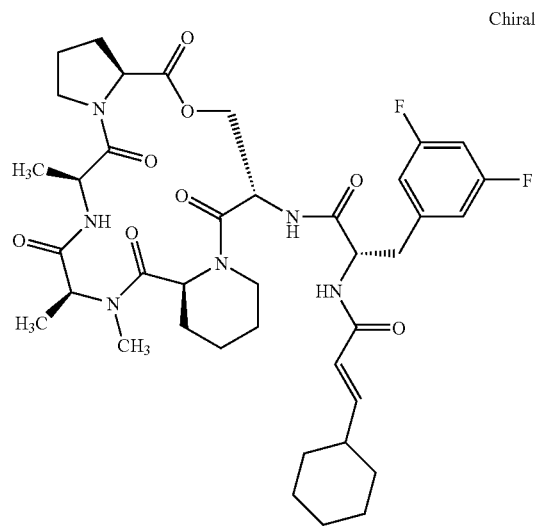

| Example | Structure | | MW | HPLC or LCMS Rt [min] | MS ESI [M + H]+ | HPL or LCMS method |
|---|---|---|---|---|---|---|
| 149 | 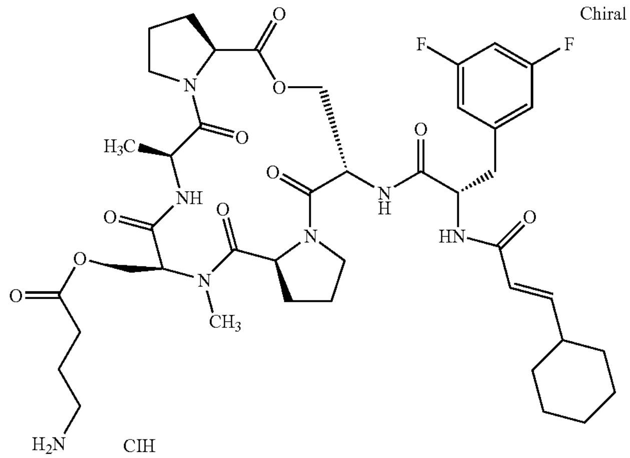 | Chiral | 894.41 | 3.50 | 857 | MHZ-2Q-01 |
| 150 | 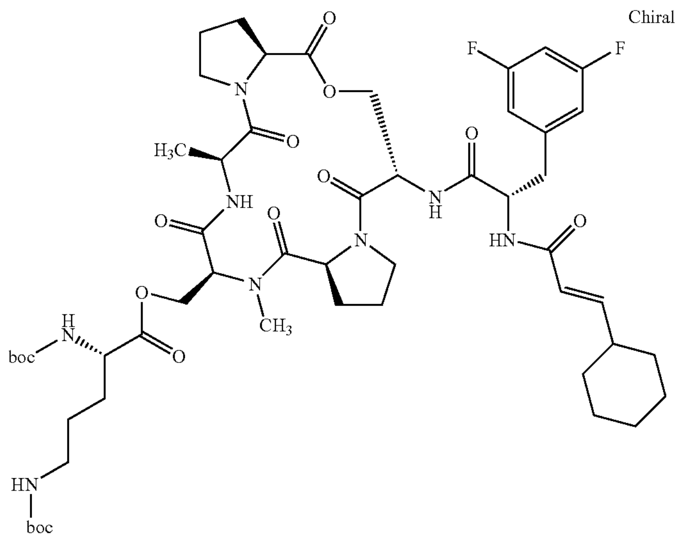 | Chiral | 1087.22 | 5.40 | 1086 | MHZ-2P-01 |
| 151 | 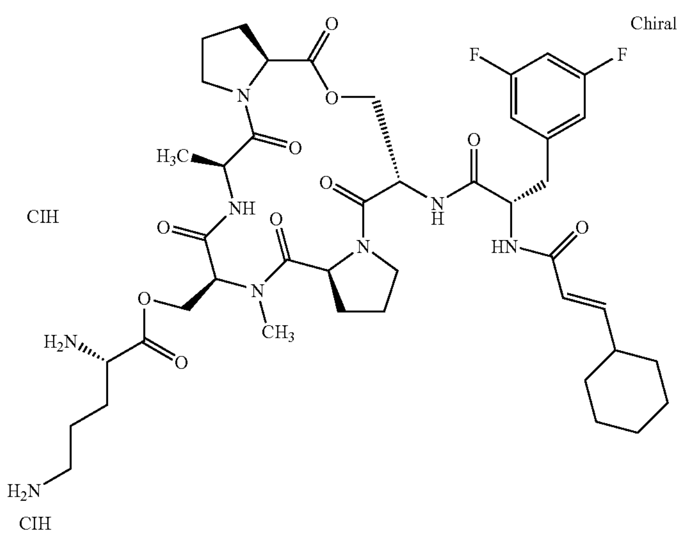 | Chiral | 959.91 | 3.26 | 886 | MHZ-2P-01 |

-continued

| Example | Structure | MW | HPLC or LCMS Rt [min] | MS ESI [M + H]+ | HPL or LCMS method |
|---|---|---|---|---|---|
| 152 | 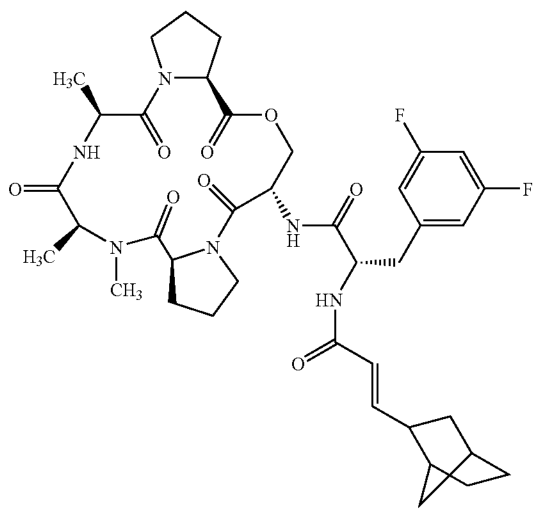 | 768.85 | 3.47 | 768 | SMKL-ZQ-01 |
| 153 | 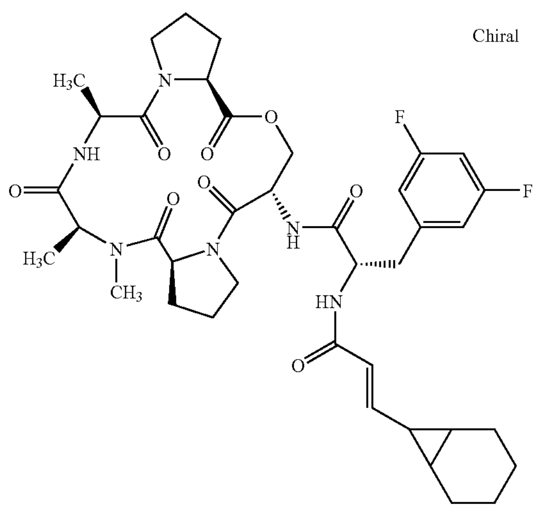 | 768.85 | 3.38 | 768 | SMKL-ZQ-01 |
| 154 | 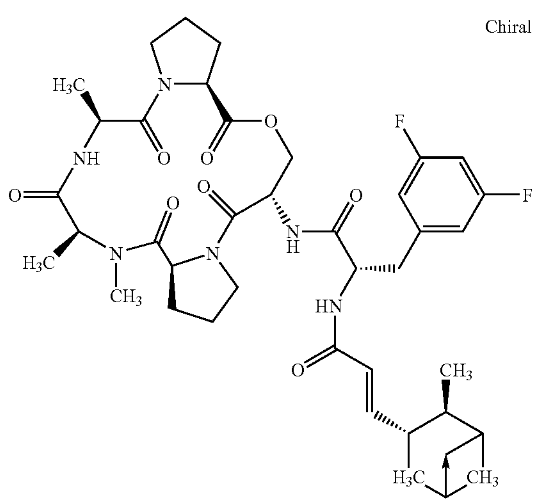 | 810.93 | 3.83 | 810 | SMKL-ZQ-01 |

-continued
| Example | Structure | | MW | HPLC or LCMS Rt [min] | MS ESI [M + H]+ | HPL or LCMS method |
|---|---|---|---|---|---|---|
| 155 | 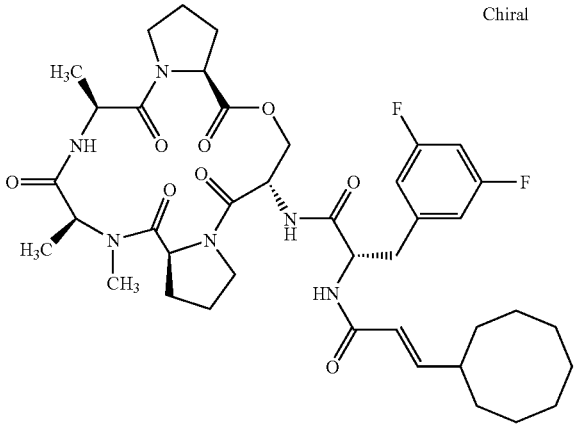 | Chiral | 784.90 | 3.39 | 784 | SMKL-ZQ-01 |
| 156 | 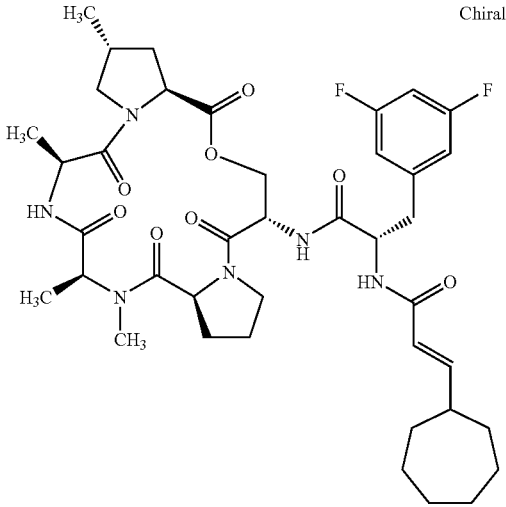 | Chiral | 784.90 | 3.41 | 784 | SMKL-ZQ-01 |
| 157 | 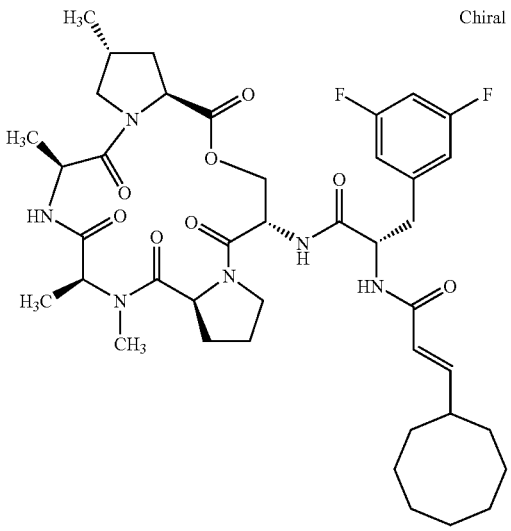 | Chiral | 798.92 | 3.53 | 798 | SMKL-ZQ-01 |

-continued
| Example | Structure | MW | HPLC or LCMS Rt [min] | MS ESI [M + H]+ | HPL or LCMS method |
|---|---|---|---|---|---|
| 158 | 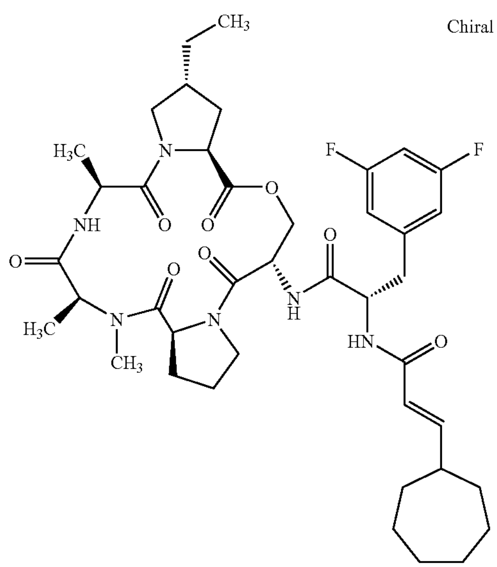 | 798.92 | 4.07 | 798 | SMKL-ZQ-01 |
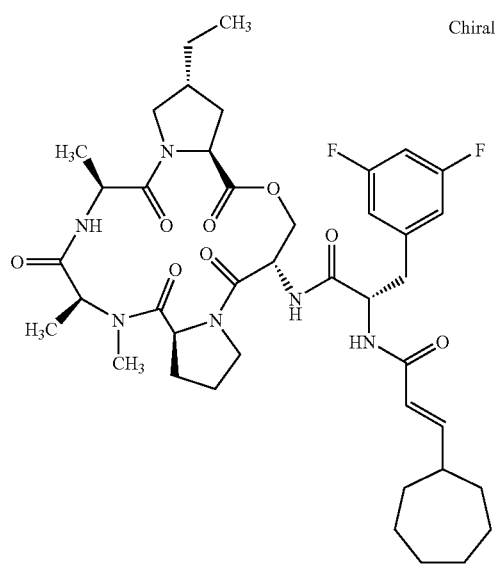
| 159 | | 798.88 | 3.09 | 798 | SMKL-ZQ-01 |
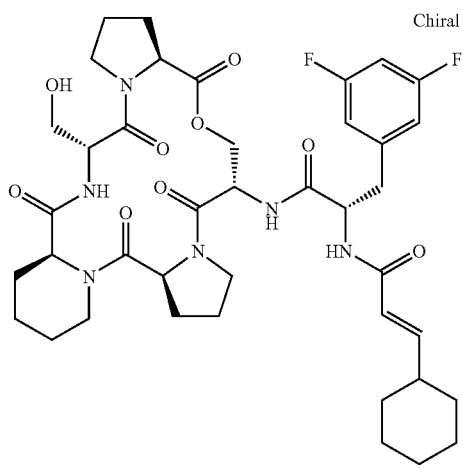

-continued
| Example | Structure | | MW | HPLC or LCMS Rt [min] | MS ESI [M + H]+ | HPL or LCMS method |
|---|---|---|---|---|---|---|
| 160 | 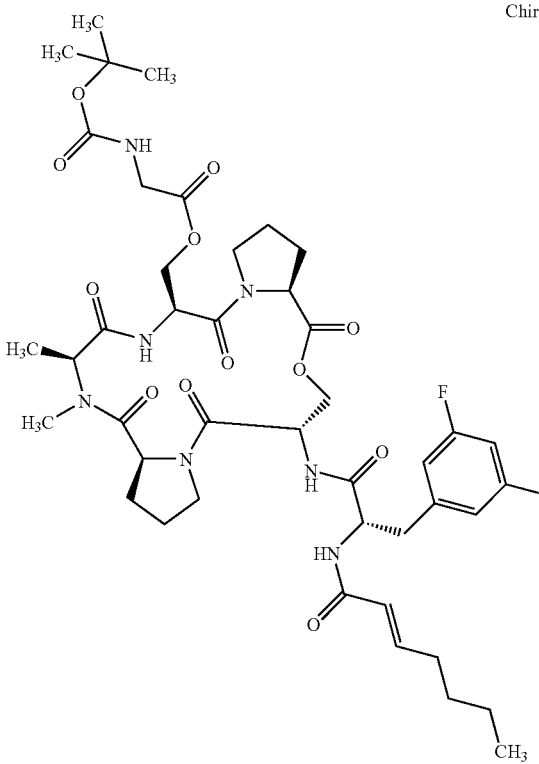 | Chiral | 903.97 | 3.62 | 903 | SMKL-ZQ-01 |
| 161 | 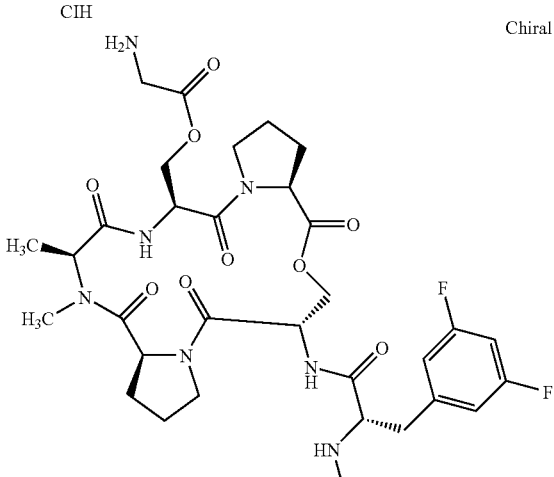 | ClH Chiral | 840.32 | 2.04 | 803 | SMKL-ZQ-01 |

What is claimed is:

1. An antibacterial compound of the general formula (I)

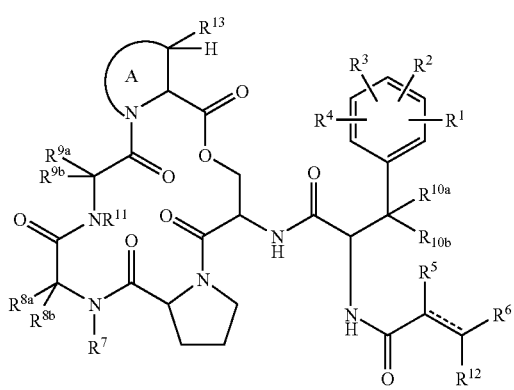

in which
R$^1$ denotes halogen,
R$^2$ is hydrogen or halogen,
R$^5$ denotes hydrogen, C$_1$-C$_4$-alkyl, fluorine or chlorine,
R$^6$ denotes hydrogen, halogen or alkyl,
R$^7$ denotes alkyl or (cycloalkyl)alkyl,
R$^{8a}$ denotes alkyl, alkylene, cycloalkyl or (cycloalkyl)alkyl,
where R$^{8a}$ optionally can be substituted by 1, 2 or 3 substituents, which independently of one another are selected from the group consisting of hydroxyl, alkoxy, a radical —OR$^{8a-1}$, carboxyl, alkoxycarbonyl, amino, alkylamino, dialkylamino, aminocarbonyl, alkylaminocarbonyl, dialkylaminocarbonyl, aminosulfonyl, alkylaminosulfonyl, dialkylaminosulfonyl, arylaminosulfonyl, heterocyclylaminosulfonyl, heteroarylaminosulfonyl, aminocarbonylamino, hydroxycarbonylamino, alkoxycarbonylamino, aminocarbonyloxy, in which R$^{8a-1}$ is a carbonyl-bonded amino acid radical,
or R$^7$ and R$^{8a}$, together with the carbon atom to which R$^{8a}$ is bonded and the nitrogen atom to which R$^7$ is bonded, form a heterocyclyl ring, which optionally can be substituted by 1, 2 or 3 substituents, which independently of one another are selected from the group consisting of halogen, alkyl, trifluoromethyl, trifluoromethoxy, nitro, azido, amino, alkylamino, dialkylamino, hydroxyl, alkoxy, alkanoyloxy,
R$^{8a}$ denotes hydrogen or alkyl,
R$^{9a}$ denotes hydrogen, alkyl, hydroxyalkyl, carboxylalkyl or aminoalkyl,
R$^{9b}$ denotes hydrogen or alkyl,
R$^{10a}$ denotes hydrogen, alkyl or fluorine,
R$^{10b}$ denotes hydrogen or fluorine,
R$^{11}$ denotes hydrogen or alkyl,
R$^{12}$ denotes alkyl, alkenyl, cycloalkyl, cycloalkenyl, (cycloalkyl)alkyl, (cycloalkenyl)alkyl, (cycloalkyl)alkenyl (cycloalkenyl)alkenyl,
where R$^{12}$ optionally can be substituted by 1, 2 or 3 substituents, which independently of one another are selected from the group consisting of halogen, hydroxyl, alkoxy, fluoroalkoxy, aryloxy, alkanoyloxy, alkoxycarbonyl, aminocarbonyl, alkylaminocarbonyl, dialkylaminocarbonyl, aminosulfonyl, alkylaminosulfonyl, dialkylaminosulfonyl, arylaminosulfonyl, heteroarylaminosulfonyl, heterocyclylaminosulfonyl, aminocarbonylamino, alkoxycarbonylamino, or
R$^6$ and R$^{12}$, together with the carbon atom to which they are bonded, form a cycloalkyl, which optionally can be substituted by 1 or 2 substituents, which independently of one another are selected from the group consisting of halogen, hydroxyl, alkoxy,
R$^{13}$ denotes hydrogen or alkyl,
A represents a heterocycle which optionally can be substituted by 1, 2 or 3 substituents, which independently of one another are selected from the group consisting of halogen, alkyl, trifluoromethyl, trifluoromethoxy, nitro, amino, alkylamino, dialkylamino, hydroxyl, alkoxy, alkanoyloxy, carboxyl, alkoxycarbonyl, azido, alkoxycarbonylamino,

----- represents a single or double bond,
or a pharmaceutically tolerable salt thereof.

2. An antibacterial compound of the general formula (I) as claimed in claim 1, in which
R$^1$ denotes halogen,
R$^2$ is hydrogen or halogen;
R$^5$ denotes hydrogen, methyl or fluorine,
R$^6$ denotes hydrogen or C$_1$-C$_4$-alkyl,
R$^7$ denotes alkyl,
R$^{8a}$ denotes alkyl, alkylene, cycloalkyl or (cycloalkyl)alkyl,
where R$^{8a}$ optionally can be substituted by 1 or 2 substituents, which independently of one another are selected from the group consisting of hydroxyl, alkoxy, a radical —OR$^{8a-1}$, alkoxycarbonyl, amino, alkylamino, dialkylamino, aminocarbonyl, alkylaminocarbonyl, dialkylaminocarbonyl, alkoxycarbonylamino,
in which R$^{8a}$ is a carbonyl-bonded amino acid radical,
or R$^7$ and R$^{8a}$, together with the carbon atom to which R$^{8a}$ is bonded and the nitrogen atom to which R$^7$ is bonded, form a heterocyclyl ring, which optionally can be substituted by 1 or 2 substituents, which independently of one another are selected from the group consisting of halogen, alkyl, amino, alkylamino, dialkylamino, hydroxyl, alkoxy, alkanoyloxy,
R$^{8b}$ denotes hydrogen,
R$^{9a}$ denotes hydrogen, methyl or hydroxymethyl,
R$^{9b}$ denotes hydrogen,
R$^{10a}$ denotes hydrogen,
R$^{10b}$ denotes hydrogen,
R$^{11}$ denotes hydrogen,
R$^{12}$ denotes alkyl, alkenyl, (cycloalkyl)alkyl, (cycloalkenyl)alkyl, (cycloalkyl)alkenyl (cycloalkenyl)alkenyl,
where R$^{12}$ optionally can be substituted by 1 or 2 substituents, which independently of one another are selected from the group consisting of halogen, hydroxyl, alkoxy,
or
R$^6$ and R$^{12}$, together with the carbon atom to which they are bonded, form a cycloalkyl, which optionally can be substituted by 1 or 2 substituents, which independently of one another are selected from the group consisting of halogen, hydroxyl, alkoxy, $R^{13}$ denotes hydrogen, A represents a heterocycle which optionally can be substituted by 1 or 2 substituents, which independently of one another are selected from the group consisting of fluorine, alkyl, trifluoromethyl, alkoxycarbonylamino,

----- represents a single or double bond, or a pharmaceutically tolerable salt thereof.

3. An antibacterial compound of the general formula (I) as claimed in claim 1, in which $R^1$ denotes fluorine, $R^2$ denotes hydrogen or fluorine, $R^5$ denotes hydrogen or fluorine, $R^6$ denotes hydrogen, $R^7$ denotes methyl, $R^{8a}$ denotes $C_1$-$C_4$-alkyl, where $R^{8a}$ optionally can be substituted by 1 substituent selected from the group consisting of hydroxyl and a radical —$OR^{8a-1}$, in which $R^{8a-1}$ is an aminomethylcarbonyl radical, or $R^7$ and $R^{8a}$, together with the carbon atom to which $R^{8a}$ is bonded and the nitrogen atom to which $R^7$ is bonded, form a 5- to 6-membered nitrogen heterocyclyl ring, which can contain up to 2 nitrogen atoms and which optionally can be substituted by 1 substituent selected from the group consisting of alkyl, amino, alkylamino, dialkylamino, hydroxyl, $R^{8b}$ denotes hydrogen, $R^{9a}$ denotes hydrogen, alkyl or hydroxymethyl, $R^{9b}$ denotes hydrogen, $R^{10a}$ denotes hydrogen, $R^{10b}$ denotes hydrogen, $R^{11}$ denotes hydrogen, $R^{12}$ denotes alkyl, alkenyl, cycloalkyl, cycloalkenyl, (cycloalkyl)alkyl, (cycloalkenyl)alkyl, (cycloalkyl)alkenyl (cycloalkenyl)alkenyl, where $R^{12}$ optionally can be monosubstituted by hydroxyl, or $R^6$ and $R^{12}$, together with the carbon atom to which they are bonded, form a 5- to 6-membered cycloalkyl, which optionally can be monosubstituted by hydroxyl, $R^{13}$ denotes hydrogen, A represents a 5-membered heterocycle which contains 1 nitrogen atom and which optionally can be monosubstituted by a substituent selected from the group consisting of fluorine, alkyl,

----- represents a single or double bond, or a pharmaceutically tolerable salt thereof.

4. An antibacterial compound as claimed in claim 1, which has the general formula (II):

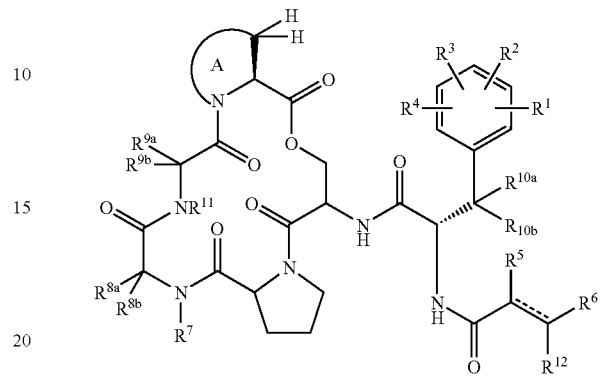

in which
A,

----- and $R^1$, $R^2$ and $R^5$ to $R^{12}$ are as defined in claim 1.

5. An antibacterial compound of the general formula (I) as claimed in claim 1, in which $R^5$ denotes hydrogen.

6. An antibacterial compound of the general formula (I) as claimed in claim 1, in which $R^6$ denotes hydrogen.

7. An antibacterial compound of the general formula (I) as claimed in claim 1, in which $R^7$ denotes methyl.

8. An antibacterial compound of the general formula (I) as claimed in claim 1, in which $R^{8a}$ denotes methyl hydroxymethyl or —$OR^{8a-1}$, in which $R^{8a-1}$ denotes a carbonylbonded amino acid radical and $R^{8b}$ denotes hydrogen.

9. An antibacterial compound of the general formula (I) as claimed in claim 1, in which in which $R^{9a}$ denotes alkyl, and $R^{9b}$ denotes hydrogen.

10. An antibacterial compound of the general formula (I) as claimed in claim 1, in which $R^{10a}$ and $R^{10b}$ denote hydrogen.

11. An antibacterial compound of the general formula (I) as claimed in claim 1, in which $R^{11}$ denotes hydrogen.

12. An antibacterial compound of the general formula (I) as claimed in claim 1, in which $R^{12}$ is selected from the following group:

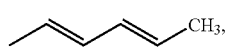 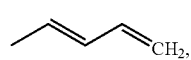

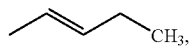 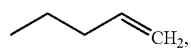

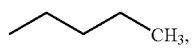 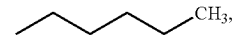

-continued

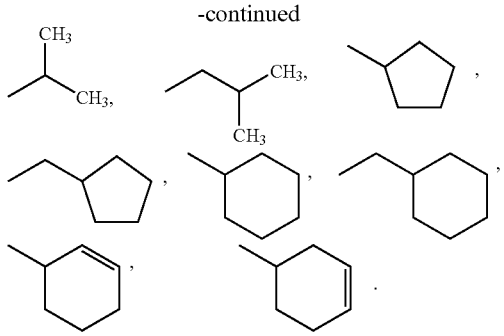

13. An antibacterial compound of the general formula (I) as claimed in claim 1, in which $R^{13}$ denotes hydrogen.

14. An antibacterial compound of the general formula (I) as claimed in claim 1, in which A is a 5-membered heterocycle which contains 1 nitrogen atom and which optionally can be monosubstituted by a substituent selected from the group consisting of fluorine and alkyl.

15. A process for the preparation of the compounds of the general formula (I) as claimed in claim 1, in which compounds of the general formula (V)

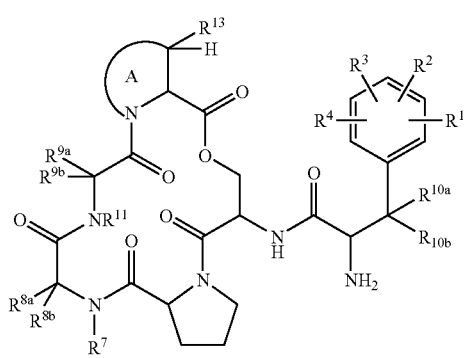

(V)

in which $R^1$, $R^2$, $R^7$ to $R^{11}$, $R^{13}$ and A have the meaning indicated in claim 1, are reacted with compounds of the general formula (XXV)

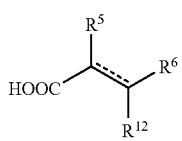

(XXV)

in which $R^5$, $R^6$, $R^{12}$ and

----- have the meaning indicated in claim 1, where these optionally can be present in activated form.

16. A medicament comprising an antibacterial compound of the general formula (I) as claimed in claim 1 and excipients.

17. A compound of the general formula (I)

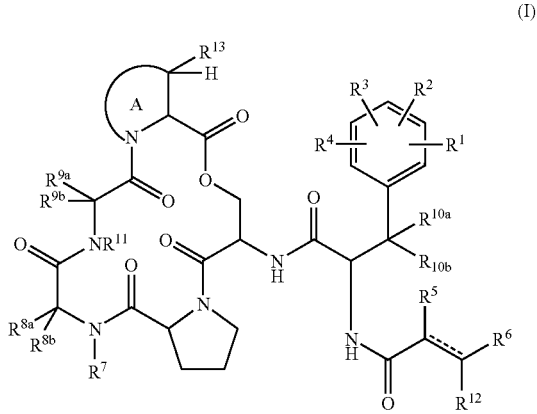

(I)

in which $R^1$ denotes halogen, alkyl, trifluoromethyl, trifluoromethoxy, nitro, amino, alkylamino, dialkylamino or alkylcarbonylamino, $R^2$ denotes hydrogen, halogen, alkyl, nitro, amino, alkylamino, dialkylamino, or alkylcarbonylamino, $R^3$ denotes hydrogen, halogen, alkyl, nitro, amino, alkylamino, dialkylamino, or alkylcarbonylamino, $R^4$ denotes hydrogen, halogen, alkyl, nitro, amino, alkylamino, dialkylamino, or alkylcarbonylamino, $R^5$ denotes hydrogen, $C_1$-$C_4$-alkyl, fluorine or chlorine, $R^6$ denotes hydrogen, halogen or alkyl, $R^7$ and $R^{8a}$, together with the carbon atom to which $R^{8a}$ is bonded and the nitrogen atom to which $R^7$ is bonded, form a heterocyclyl ring, which optionally can be substituted by 1 or 2 substituents, which independently of one another are selected from the group consisting of halogen, alkyl and amino, $R^{8b}$ denotes hydrogen or alkyl, $R^{9a}$ denotes hydrogen, alkyl, hydroxyalkyl, carboxylalkyl or aminoalkyl, $R^{9b}$ denotes hydrogen or alkyl, $R^{10a}$ denotes hydrogen, alkyl or fluorine, $R^{10b}$ denotes hydrogen or fluorine, $R^{11}$ denotes hydrogen or alkyl, $R^{12}$ denotes alkyl, alkenyl, cycloalkyl, cycloalkenyl, (cycloalkyl)alkyl, (cycloalkenyl)alkyl, (cycloalkyl)alkenyl (cycloalkenyl)alkenyl, where $R^{12}$ optionally can be substituted by 1, 2 or 3 substituents, which independently of one another are selected from the group consisting of halogen, hydroxyl, alkoxy, fluoroalkoxy, aryloxy, alkanoyloxy, alkoxycarbonyl, aminocarbonyl, alkylaminocarbonyl, dialkylaminocarbonyl, aminosulfonyl, alkylaminosulfonyl, dialkylaminosulfonyl, arylaminosulfonyl, heteroarylaminosulfonyl, heterocyclylaminosulfonyl, aminocarbonylamino, alkoxycarbonylamino, or $R^6$ and $R^{12}$, together with the carbon atom to which they are bonded, form a cycloalkyl, which optionally can be substituted by 1 or 2 substituents, which independently of one another are selected from the group consisting of halogen, hydroxyl, alkoxy, $R^{13}$ denotes hydrogen or alkyl, A represents a heterocycle which optionally can be substituted by 1, 2 or 3 substituents, which independently of one another are selected from the group consisting of halogen, alkyl, tnfluoromethyl, trifluoromethoxy, nitro, amino, alkylamino, dialkylamino, hydroxyl, alkoxy, alkanoyloxy, carboxyl, alkoxycarbonyl, azido, alkoxycarbonylamino,

----- repesents a single or double bond,
or a pharmaceutically tolerable salt thereof.

18. A compound of the general formula (I)

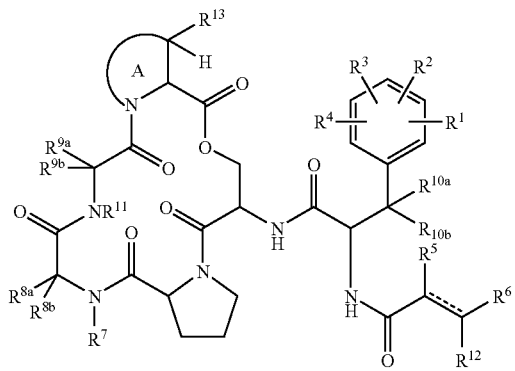

(I)

in which
R$^1$ denotes halogen, alkyl, trifluoromethyl, trifluoromethoxy, nitro, amino, alkylamino, dialkylamino or alkylcarbonylamino,
R$^2$ denotes hydrogen, halogen, alkyl, nitro, amino, alkylamino, dialkylamino, or alkylcarbonylamino,
R$^3$ denotes hydrogen, halogen, alkyl, nitro, amino, alkylamino, dialkylamino, or alkylcarbonylamino,
R$^4$ denotes hydrogen, halogen, alkyl, nitro, amino, alkylamino, dialkylamino, or alkylcarbonylamino,
R$^5$ denotes hydrogen, C$_1$-C$_4$-alkyl, fluorine or chlorine,
R$^6$ denotes hydrogen, halogen or alkyl,
R$^7$ denotes alkyl or (cycloalkyl)alkyl,
R$^{8a}$ denotes alkyl, alkylene, cycloalkyl or (cycloalkyl)alkyl,
where R$^{8a}$ optionally can be substituted by 1, 2 or 3 substituents, which independently of one another are selected from the group consisting of hydroxyl, alkoxy, a radical —OR$^{8a-1}$, carboxyl, alkoxycarbonyl, amino, alkylamino, dialkylamino, aminocarbonyl, alkylaminocarbonyl, dialkylaminocarbonyl, aminosulfonyl, alkylaminosulfonyl, dialkylaminosulfonyl, arylaminosulfonyl, heterocyclylaminosulfonyl, heteroarylaminosulfonyl, aminocarbonylamino, hydroxycarbonylamino, alkoxycarbonylamino, aminocarbonyloxy, in which R$^{8a-1}$ is a carbonyl-bonded amino acid radical,
or R$^7$ and R$^{8a}$, together with the carbon atom to which R$^{8a}$ is bonded and the nitrogen atom to which R$^7$ is bonded, form a heterocyclyl ring, which optionally can be substituted by 1, 2 or 3 substituents, which independently of one another are selected from the group consisting of halogen, alkyl, trifluoromethyl, trifluoromethoxy, nitro, azido, amino, alkylamino, dialkylamino, hydroxyl, alkoxy, alkanoyloxy,
R$^{8b}$ denotes hydrogen or alkyl,
R$^{9a}$ denotes hydrogen, alkyl, hydroxyalkyl, carboxylalkyl or aminoalkyl,
R$^{9b}$ denotes hydrogen or alkyl,
R$^{10a}$ denotes hydrogen, alkyl or fluorine,
R$^{10b}$ denotes hydrogen or fluorine,
R$^{11}$ denotes hydrogen or alkyl,
R$^{12}$ denotes C$_3$-C$_8$-alkyl,
R$^{13}$ denotes hydrogen or alkyl,
A represents a heterocycle which optionally can be substituted by 1, 2 or 3 substituents, which independently of one another are selected from the group consisting of halogen, alkyl, trifluoromethyl, trifluoromethoxy, nitro, amino, alkylamino, dialkylamino, hydroxyl, alkoxy, alkanoyloxy, carboxyl, alkoxycarbonyl, azido, alkoxycarbonylamino,

----- represents a single or double bond,
or a pharmaceutically tolerable salt thereof.

* * * * *